(12) United States Patent
Itagaki et al.

(10) Patent No.: US 10,005,864 B2
(45) Date of Patent: Jun. 26, 2018

(54) METALLOCENE COMPOUND, CATALYST FOR OLEFIN POLYMER, METHOD FOR PRODUCING OLEFIN POLYMER, AND OLEFIN POLYMER

(71) Applicant: JAPAN POLYETHYLENE CORPORATION, Tokyo (JP)

(72) Inventors: Koji Itagaki, Mie (JP); Tsutomu Sakuragi, Mie (JP); Takayoshi Takahashi, Kanagawa (JP)

(73) Assignee: JAPAN POLYETHYLENE CORPORATION, Tokyo (JP)

( * ) Notice: Subject to any disclaimer, the term of this patent is extended or adjusted under 35 U.S.C. 154(b) by 0 days. days.

(21) Appl. No.: 15/590,633

(22) Filed: May 9, 2017

(65) Prior Publication Data
US 2017/0320981 A1 Nov. 9, 2017

Related U.S. Application Data

(62) Division of application No. 14/770,479, filed as application No. PCT/JP2014/054676 on Feb. 26, 2014, now Pat. No. 9,783,625.

(30) Foreign Application Priority Data

Feb. 27, 2013 (JP) ................................. 2013-036535

(51) Int. Cl.
| | | |
|---|---|---|
| C08F 4/6592 | (2006.01) | |
| C08F 110/02 | (2006.01) | |
| C08F 210/16 | (2006.01) | |
| C07F 17/00 | (2006.01) | |
| C08F 10/00 | (2006.01) | |
| C08F 4/659 | (2006.01) | |

(52) U.S. Cl.
CPC ............ C08F 210/16 (2013.01); C07F 17/00 (2013.01); C08F 4/65908 (2013.01); C08F 4/65912 (2013.01); C08F 4/65927 (2013.01); C08F 10/00 (2013.01)

(58) Field of Classification Search
CPC .............. C08F 4/65927; C08F 4/65908; C08F 4/65912; C08F 110/02; C08F 210/16
See application file for complete search history.

(56) References Cited

U.S. PATENT DOCUMENTS

| | | | |
|---|---|---|---|
| 5,698,645 | A | 12/1997 | Weller |
| 6,350,830 | B1 | 2/2002 | Gores et al. |
| 8,461,365 | B2 | 6/2013 | Nakano et al. |
| 2001/0053833 | A1 | 12/2001 | Nakano et al. |
| 2003/0149199 | A1 | 8/2003 | Schottek et al. |
| 2004/0127731 | A1 | 7/2004 | Ushioda et al. |
| 2004/0260107 | A1 | 12/2004 | Oberhoff et al. |
| 2005/0154139 | A1 | 7/2005 | Ishihara |
| 2006/0020096 | A1 | 1/2006 | Schottek et al. |
| 2010/0267907 | A1 | 10/2010 | Dimeska et al. |
| 2011/0230622 | A1 | 9/2011 | Nakano et al. |
| 2011/0230630 | A1 | 9/2011 | Sell et al. |
| 2012/0329964 | A1 | 12/2012 | Dimeska et al. |
| 2014/0303332 | A1 | 10/2014 | Yang |

FOREIGN PATENT DOCUMENTS

| | | |
|---|---|---|
| CN | 1120551 | 4/1996 |
| CN | 102245620 | 11/2011 |
| EP | 1052263 | 11/2000 |
| EP | 2341087 | 7/2011 |
| JP | 4-337308 | 11/1992 |
| JP | 6-287257 | 10/1994 |
| JP | 11-240909 | 9/1999 |
| JP | 2001-011089 | 1/2001 |
| JP | 2002-504569 | 2/2002 |
| JP | 2002-194016 | 7/2002 |
| JP | 2003-206325 | 7/2003 |
| JP | 2004-352707 | 12/2004 |
| JP | 2007-505947 | 3/2007 |
| JP | 2008-101034 | 5/2008 |
| JP | 4288658 | 4/2009 |
| JP | 4416507 | 12/2009 |
| JP | 2010/163423 | 7/2010 |
| JP | 2011-500800 | 1/2011 |
| JP | 2011-144157 | 7/2011 |
| JP | 4901043 | 1/2012 |
| JP | 2012-121882 | 6/2012 |
| JP | 2012-513463 | 6/2012 |
| JP | 2013-001737 | 1/2013 |
| JP | 2015-42617 | 3/2015 |
| WO | 2004/106351 | 12/2004 |
| WO | 2011/080152 | 7/2011 |

OTHER PUBLICATIONS

Decision of Rejection from Chinese Patent Application No. 201480011052.7 dated Nov. 27, 2017.
Karresnberg et al., "Terminal and Penultimate Reactivity Ratios in Single-Site Ethene/Propene Copolymerizations: Comparison of Kakugo and Direct Peak Methods", Macromol. Chem. Phys., 2005, pp. 206, 1675-1683.
Tynys et al., "Ethylene-Propylene Copolymerisations: Effect of Metallocene Structure on Termination Reactions and Polymer Microstructure", Macromol. Chem. Phys., 2005, pp. 206, 1043-1056.
Spaleck et al., "The Influence of Aromatic Substituents on the Polymerization Behavior of Bridged Zirconocene Catalysts", Organometallics, 1994, pp. 13, 954-963.
Quijada et al., "The influence of the comonomer in the copolymerization of ethylene with a-olefins using C2H4[Ind]2ZrC12/methylaluminoxane as catalyst system", Macromol. Chem. Phys., 1996, pp. 197, 3091-3098.

(Continued)

Primary Examiner — Caixia Lu
(74) Attorney, Agent, or Firm — Greenblum & Bernstein, P.L.C.

(57) ABSTRACT

The invention provides a specific metallocene compound and an olefin polymerization catalyst for use for a catalyst for producing an olefin polymer having a sufficiently high molecular weight while maintaining excellent copolymerizability at a polymerization temperature and under polymerization conditions industrially advantageous in polymerization of an olefin such as ethylene or the like, and provides a method for producing an olefin polymer using the catalyst.

8 Claims, No Drawings

(56) References Cited

OTHER PUBLICATIONS

International Search Report issued with respect to application No. PCT/JP2014/054676, dated Jun. 3, 2014.
International Preliminary Report on Patentability issued with respect to application No. PCT/JP2014/054676, dated Sep. 1, 2015.
European Search Report issued with respect to application No. 14757800.9, dated Oct. 21, 2015.
Extended European Search Report issued with respect to Application No. 16000898.3, dated Aug. 31, 2016.
Chinese Office Action issued with respect to Application No. 201480011052.7, dated Dec. 1, 2016.
Yong-Woo et al., "Synthesis and characterization of ethylene-propylene random copolymers with isotactic propylene sequence", Polymer, 2001, pp. 9611-9615, vol. 42.
International Search Report for application No. PCT/JP2013/079093, dated Jan. 21, 2014.
International Preliminary Report on Patentability for application No. PCT/JP2013/079093, dated May 5, 2015.
Chinese office Action issued with respect to application No. 201380057170.7, dated Mar. 24, 2016.
Chinese office Action issued with respect to application No. 201380057170.7, dated Sep. 20, 2016.
Chinese office Action issued with respect to application No. 201480011052.7, dated May 15, 2017.

METALLOCENE COMPOUND, CATALYST FOR OLEFIN POLYMER, METHOD FOR PRODUCING OLEFIN POLYMER, AND OLEFIN POLYMER

CROSS-REFERENCE TO RELATED APPLICATIONS

The present application is a divisional application of pending U.S. application Ser. No. 14/770,479, filed on Aug. 26, 2015, which is a National Stage of International Patent Application No. PCT/JP2014/054676 filed on Feb. 26, 2014, which claims priority to Japanese Application No. 2013-036535 filed on Feb. 27, 2013. The disclosures of U.S. application Ser. No. 14/770,479 and International Patent Application No. PCT/JP201.4/054676 are incorporated by reference herein in their entireties.

TECHNICAL FIELD

The present invention relates to a novel metallocene compound and a method for producing an olefin polymer, and more precisely, to an olefin polymerization catalyst excellent in copolymerizability in olefin copolymerization and capable of producing an olefin polymer having a high-molecular weight and to a method for producing an olefin polymer using the catalyst.

BACKGROUND ART

As an olefin-based copolymer typically including an ethylene/α-olefin copolymer or a propylene/α-olefin copolymer, there have been produced a broad range of polymers having different physical properties that are excellent in mechanical properties and cover from hard to soft ones; and regarding their use applications, the polymers are widely used covering from industrial materials for films, sheets, fibers, nonwoven fabrics, various containers, molded articles, modifiers and others down to life materials.

In general, it is known that copolymers produced through copolymerization with a comonomer such as 1-butene, 1-hexene or the like are excellent in the performance of flexibility, low-temperature impact resistance, environmental stress cracking resistance, transparency or the like, as compared with an ethylene homopolymer and a propylene homopolymer. For further improving these capabilities, it is necessary to increase the comonomer content in the copolymer while the high-molecular weight of the copolymer is kept as such. In addition, it is known that, when a complex catalyst, as typified by a metallocene catalyst, is used, then the comonomer introduced into the copolymer can be uniformly distributed therein and the above-mentioned capabilities of the copolymer can be thereby further improved.

Consequently, in producing ethylene and propylene copolymers having these capabilities, it is desired to provide a complex catalyst excellent in copolymerizability and capable of producing a high-molecular-weight olefin copolymer in a temperature range of from 50 to 300° C. that is efficient in an industrial process and capable of producing a copolymer having a high comonomer content even at a low comonomer concentration from the viewpoint of the process load. However, there is a report pointing out a problem that, in olefin copolymerization using a complex catalyst, as typified by a metallocene catalyst, the molecular weight of the polymer to be obtained decreases with the elevation of the polymerization temperature or with the increase in the comonomer content in the resultant copolymer (for example, see NPL 1).

Accordingly, for producing the olefin polymers having these capabilities, there is desired a metallocene catalyst excellent in copolymerizability in a temperature range of from 50 to 300° C. efficient in an industrial process and capable of producing an olefin copolymer having a high molecular weight.

As a metallocene having excellent copolymerizability and capable of producing an olefin copolymer having a high molecular weight, there is known a bridged bisindenyl complex having a phenyl group at the 4-position of the indenyl ring. In particular, it is reported that substituent introduction of a methyl group into the 2-position of the indenyl ring is effective for improving the molecular weight (see NPL 2, 3), and therefore, searching for a 2-positioned substituent in a bridged bisindenyl complex having a phenyl group at the 4-position thereof is kept continued for producing a polymer having a higher molecular weight.

NPL 4 reports that, in ethylene polymerization under a high-pressure condition, a complex having an iPr group can produce a polyethylene having a higher molecular weight than a complex having an Me group as the 2-position substituent thereof. PTL 1 and 2 report a complex having an α-branched alkyl substituent at the 2-position, PTL 3 reports a complex having a hetero-aromatic ring substituent at the 2-position, and PTL 4 to 7 report a complex in which the 2-positioned substituent differs between the two bisindenyl rings, all saying that the respective complexes are effective for producing high-molecular-weight olefin polymers and olefin copolymers. However, as a result of the present inventors' investigations, it has become clarified that when these catalysts are used for polymerization at a high temperature preferred from the production efficiency, then the molecular weight of the resultant polymers is insufficient.

In addition, when the structure of the 2-positioned substituent becomes more complicated, and in case where such complexes are produced on a large scale that is industrially necessary in organic synthesis, there occurs a problem in that the production cost for the complexes increases owing to the necessity of complicated synthesis routes and multi-stage synthesis routes. Consequently, it is desired to develop a novel complex capable of exhibiting more excellent performance than already-existing catalysts, and at the same time, having a simple complex structure as compared already-existing ones and capable of being synthesized easily.

Given the situation, there has been desired a metallocene compound which is easy to synthesize and which can produce a high-molecular weight olefin copolymer at a polymerization temperature and under polymerization conditions that are advantageous industrially while maintaining excellent copolymerizability, as well as a metallocene catalyst and a production method for an olefin polymer using the compound.

CITATION LIST

Patent Literature

PTL 1: JP-T 2011-500800
PTL 2: JP-T 2012-513463
PTL 3: JP-A 2002-194016
PTL 4: Japanese Patent 4901043
PTL 5: Japanese Patent 4416507
PTL 6: Japanese Patent 4288658
PTL 7: JP-A 2004-352707

Non-Patent Literature

NPL 1: Macromol. Chem. Phys., 1996, Vol. 197, pp. 3091-3097
PTL 2: Organometallics, 1994, Vol. 13, pp. 954-963
PTL 3: Macromol. Chem. Phys., 2005, Vol. 206, pp. 1675-1683
PTL 4: Macromol. Chem. Phys., 2005, Vol. 206, pp. 1043-1056

SUMMARY OF INVENTION

Technical Problem

In consideration of the problems with the background art, the subject matter of the present invention is to provide a metallocene compound for use as a catalyst for producing an olefin polymer, especially an ethylenic copolymer having a sufficiently high molecular weight, at a polymerization temperature and under polymerization conditions industrially advantageous in polymerization of an olefin such as ethylene or the like while maintaining excellent copolymerizability and the olefin polymerization catalyst, as well as a production method for an olefin polymer using the catalyst.

Solution to Problem

For solving the above-mentioned problems, the present inventors have made experimental investigations with many-sided observations for obtaining an olefin-based copolymer having a sufficiently high molecular weight under industrially advantageous conditions and maintaining excellent copolymerizability according to an improved technical method for a metallocene catalyst as a polymerization catalyst for an olefin-based copolymer, and in the process thereof, the inventors have found that, when an olefin polymerization catalyst that contains a metallocene compound having a specific structure is used, then an olefin polymer having a sufficiently high molecular weight can be produced in polymerization of an olefin such as ethylene or the like, at a polymerization temperature and under polymerization conditions industrially advantageous while exhibiting excellent copolymerizability, and have completed the present invention.

Specifically, the present inventors have found that, as a technical method for solving the above-mentioned problems, a novel metallocene compound having a specific substituent at a specific position, or that is, a metallocene compound having a hydrogen atom as the substituent at the 2-position of the indenyl ring thereof and having a bridged bisindenyl skeleton with the two indenyl rings linked via one carbon atom having a substituent can solve the above-mentioned problems.

Accordingly, the olefin polymerization catalyst component containing the metallocene compound that constitutes the basic constitution of the present invention uses the novel, specific transition metal compound, and the catalyst is characterized by the chemical, stereospecific, and electronic environmental structure of the ligand in the catalyst structure of the metallocene catalyst, and with that, the novel compound is effective for producing an olefin-based copolymer having a sufficiently high molecular weight under industrially advantageous conditions.

Specifically, the present invention includes the following constitutions (1) to (13).

(1) A metallocene compound represented by the following general formula [I]:

[Chem. 1]

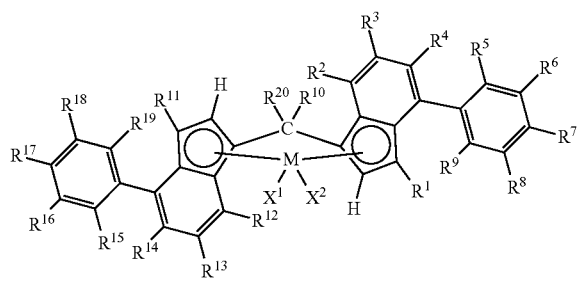

[In the formula [I], M represents Ti, Zr or Hf;

$X^1$ and $X^2$ are the same or different, each representing a hydrogen atom, an alkyl group having from 1 to 10 carbon atoms, an alkoxy group having from 1 to 10 carbon atoms, an aryl group having from 6 to 20 carbon atoms, an aryloxy group having from 6 to 10 carbon atoms, an alkenyl group having from 2 to 10 carbon atoms, an arylalkyl group having from 7 to 40 carbon atoms, an alkylaryl group having from 7 to 40 carbon atoms, an arylalkenyl group having from 8 to 40 carbon atoms, an alkyl group having from 1 to 20 carbon atoms and substituted with a silyl group having a hydrocarbon group having from 1 to 6 carbon atoms, a substituted amino group having from 1 to 10 carbon atoms, a group OH or a halogen atom;

$R^1$ to $R^9$ and $R^{11}$ to $R^{19}$ are the same or different, each representing a hydrogen atom, a halogen atom, an alkyl group having from 1 to 10 carbon atoms, a halogenoalkyl group having from 1 to 10 carbon atoms, an aryl group having from 6 to 20 carbon atoms, an alkoxy group having from 1 to 10 carbon atoms, a silyl group having a hydrocarbon group having from 1 to 6 carbon atoms, an alkyl group having from 1 to 20 carbon atoms and substituted with a silyl group having a hydrocarbon group having from 1 to 6 carbon atoms, a group —$NR^{21}_2$, a group —$SR^{21}$, a group —$OSiR^{21}_3$ or a group —$PR^{21}_2$ (where $R^{21}$'s are the same or different, each representing a halogen atom, an alkyl group having from 1 to 10 carbon atom or an aryl group having from 6 to 20 carbon atoms), the neighboring groups of $R^1$ to $R^9$ and $R^{11}$ to $R^{19}$ may form one or more aromatic rings or aliphatic rings along with the atom bonding them, or $R^4$ and $R^5$, or $R^4$ and $R^9$, or $R^{14}$ and $R^{15}$, or $R^{14}$ and $R^{19}$ may form one aromatic ring or aliphatic ring along with the atom bonding them;

$R^{10}$ and $R^{20}$ are the same or different, each representing a hydrogen atom, a halogen atom, an alkyl group having from 1 to 10 carbon atoms, a fluoroalkyl group having from 1 to 10 carbon atoms, an alkoxy group having from 1 to 10 carbon atoms, an aryl group having from 6 to 20 carbon atoms, a fluoroaryl group having from 6 to 10 carbon atoms, an aryloxy group having from 6 to 10 carbon atoms, an alkenyl group having from 2 to 10 carbon atoms, an arylalkyl group having from 7 to 40 carbon atoms, an alkylaryl group having from 7 to 40 carbon atoms, or an arylalkenyl group having from 8 to 40 carbon atoms, provided that $R^{10}$ and $R^{20}$ are not hydrogen atoms at the same time, and $R^{10}$ and $R^{20}$ may form one or more rings along with the atom bonding them.]

(2) The metallocene compound according to the (1) above, wherein $R^5$ to $R^9$ and $R^{15}$ to $R^{19}$ are the same or different, each representing a hydrogen atom, a halogen atom, an alkyl group having from 1 to 10 carbon atoms, a halogenoalkyl group having from 1 to 10 carbon atoms, an aryl group having from 6 to 10 carbon atoms, a group —$NR^{21}_2$, a group —$SR^{21}$, a group —$OSiR^{21}_3$ or a group —$PR^{21}_2$ (where $R^{21}$'s are the same or different, each representing a halogen atom, an alkyl group having from 1 to 10 carbon atom or an aryl group having from 6 to 10 carbon atoms), and all of $R^5$ to $R^9$ and $R^{15}$ to $R^{19}$ are not hydrogen atoms at the same time.

(3) The metallocene compound according to the (1) or (2) above, wherein $R^{10}$ and $R^{20}$ are the same or different, each representing a halogen atom, an alkyl group having from 1 to 10 carbon atoms, a fluoroalkyl group having from 1 to 10 carbon atoms, an aryl group having from 7 to 10 carbon atoms, a fluoroaryl group having from 6 to 10 carbon atoms, an alkenyl group having from 2 to 10 carbon atoms, an arylalkyl group having from 7 to 40 carbon atoms, an alkylaryl group having from 7 to 40 carbon atoms or an arylalkenyl group having from 8 to 40 carbon atoms, provided that the total of the carbon atoms that $R^{10}$ and $R^{20}$ contain is 2 or more, and $R^{10}$ and $R^{20}$ may form one or more ring along with the atom bonding them.

(4) The metallocene compound according to any one of the (1) to (3) above, wherein $R^{10}$ and $R^{20}$ may form one or more ring along with the atom bonding them.

(5) The metallocene compound according to the (4) above, wherein the ring formed by $R^{10}$ and $R^{20}$ is a 4-membered ring or a 5-membered ring.

(6) The metallocene compound according to any one of the (1) to (5) above, wherein M is Hf.

(7) An olefin polymerization catalyst comprising the following components (A) and (B), and optionally comprising the following component (C):
Component (A): The metallocene compound according to any one of the (1) to (6) above.
Component (B): A compound or an ion-exchanging layered silicate, which reacts with the component (A) to form an ion pair.
Component (C): An organoaluminium compound.

(8) The olefin polymerization catalyst according to the (7) above, wherein the component (B) is a boron compound.

(9) A method for producing an olefin polymer, which comprises carrying out an olefin polymerization or copolymerization using the olefin polymerization catalyst according to the (7) or (8) above.

(10) The method for producing an olefin polymer according to the (9) above, wherein the olefin to be used includes ethylene.

(11) The method for producing an olefin polymer according to the (9) or (10) above, wherein the polymerization temperature is 120° C. or more.

(12) An olefin polymer obtained according to the production method according to any one of the (9) to (11) above.

(13) The olefin polymer according to the (12) above, which is for use selected from a group consisting of films, sheets, fibers, nonwoven fabrics, containers, molded articles, modifiers, automobile parts, wires and cables.

The subsidiary inventions (embodiment inventions) relative to the basic invention (above-mentioned invention (1)) of the present invention, as mentioned above, are inventions where the substituent at each position of the metallocene compound in the olefin polymerization catalyst component is specified (above-mentioned (2) to (5)), or where the center metal is embodied (above-mentioned (6)), or where a polymerization catalyst is formed that comprises the metallocene compound as the main catalyst component and is characterized by the cocatalyst component (above-mentioned (7) and (8)), or where a method for producing a (co)polymer of an olefin, especially ethylene using the polymerization catalyst is embodied (above-mentioned (9) to (11)), or where the olefin polymer obtained by the method is embodied (above-mentioned (12) and (13)).

Using the metallocene compound of the present invention as an olefin polymerization catalyst component makes it possible to produce an olefin-based copolymer having a sufficiently high molecular weight while exhibiting excellent copolymerizability under industrially-advantageous conditions, as verified by the comparison between Examples and Comparative Examples given hereinunder. The metallocene compound represented by the general formula [I] of the present invention is basically characterized by having a stereospecific and electron-environmentally specific structure that has a hydrogen atom as the substituent at the 2-position of the indenyl ring and has, at the 4-position thereof, a phenyl group skeleton optionally having a substituent, in which the two indenyl rings are linked via one carbon atom having a substituent. It is presumed that the characteristic features of the compound would provide the specificity of the present invention.

The reason why the olefin polymerization catalyst of the present invention exhibits the above-mentioned functions and effects of the present invention will be discussed more concretely hereunder. It is considered that, in the compound, the bridging group that links the indenyl rings is a carbon atom having a small atomic radius and therefore the space around the center metal has expanded and, as a result, the compound could be readily reactive with a bulky comonomer therefore exhibiting excellent copolymerizability. In addition, it is considered that the structure where a hydrogen atom is arranged at the 2-position of the indenyl ring can stereospecifically prevent polymer release reaction that is a reason of lowering the molecular weight of a growing polymer chain including many bulky comonomers, and therefore the structure of the type can increase the molecular weight of the polymer to be produced.

As verified by the comparison between Examples and Comparative Examples to be given hereinunder, a structure having a methyl group at the 2-position of the indenyl ring and having a silicon atom arranged in the bridging group could not provide a position environment capable of sufficiently preventing polymer release reaction.

As opposed to the result, it is considered that the structure having a hydrogen atom at the 2-position of the indenyl ring and having a carbon atom as the bridging group, which has been found out in the present invention, can provide a suitable stereospecific environment capable of satisfying both the above-mentioned excellent copolymerization performance and the polymer release reaction retardation.

The present invention provides a significant difference from the already-existing inventions described in the patent literature and the non-patent literature shown in the citation list given hereinabove in point of the constituent features (specific matters of the invention) and the advantageous effects of the invention, and in particular, differing from already-existing knowledge in the art, the result of the present invention that the compound having a hydrogen atom at the 2-position of the indenyl ring can give a high-molecular-weight olefin polymer than any other compound having a substituent at the 2-position could not be anticipated at all from such already-existing literature.

In the above, the creation process of the present invention and the basic constitutions and characteristics of the invention have been described in the round, and the overall constitution of the present invention will be summarized in a panoramic view hereinunder. The present invention includes the invention unit group of (1) to (13).

The metallocene compound represented by the general formula [I] constitutes the basic invention (1); and the inventions of (2) and the others are those each comprising a subsidiary requirement added to the basic invention, or embodiments of the basic invention. The invention of the polymerization catalyst of (7) and (8), the invention of the production method of (9) to (11) and the invention of the polymer of (12) and (13) each define the additional requirement for solution to the technical problems by the present invention. All the invention units are collectively referred to as the invention group.

Advantageous Effects of Invention

Using the metallocene compound of the present invention as a polymerization catalyst makes it possible to provide an olefin polymer having a high molecular weight while exhibiting excellent copolymerizability at a polymerization temperature and under polymerization conditions that are industrially advantageous, as compared with using already-existing metallocene compounds, and therefore the metallocene compound, the olefin polymerization catalyst, and the olefin polymer production method using the olefin polymerization catalyst of the present invention are extremely useful from the industrial viewpoint.

DESCRIPTION OF EMBODIMENTS

In the following, the metallocene compound, the olefin polymerization catalyst and the olefin polymer production method using the catalyst of the present invention are described concretely and in detail in each item.
1. Metallocene Compound The metallocene compound of the present invention is a metallocene compound having a specific substituent represented by the general formula [I]. In view of the chemical structure thereof, the metallocene compound includes structural isomers. For use for an olefin polymerization catalyst, the racemic form of the compound is preferred to the meso form thereof.

[Chem. 2]

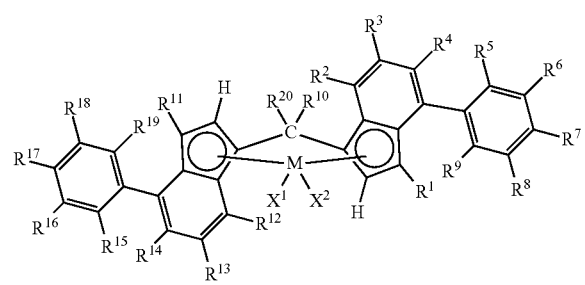

[I]

[In the formula [I], M represents Ti, Zr or Hf;

$X^1$ and $X^2$ are the same or different, each representing a hydrogen atom, an alkyl group having from 1 to 10 carbon atoms, an alkoxy group having from 1 to 10 carbon atoms, an aryl group having from 6 to 20 carbon atoms, an aryloxy group having from 6 to 10 carbon atoms, an alkenyl group having from 2 to 10 carbon atoms, an arylalkyl group having from 7 to 40 carbon atoms, an alkylaryl group having from 7 to 40 carbon atoms, an arylalkenyl group having from 8 to 40 carbon atoms, an alkyl group having from 1 to 20 carbon atoms and substituted with a silyl group having a hydrocarbon group having from 1 to 6 carbon atoms, a substituted amino group having from 1 to 10 carbon atoms, a group OH or a halogen atom;

$R^1$ to $R^9$ and $R^{11}$ to $R^{19}$ are the same or different, each representing a hydrogen atom, a halogen atom, an alkyl group having from 1 to 10 carbon atoms, a halogenoalkyl group having from 1 to 10 carbon atoms, an aryl group having from 6 to 20 carbon atoms, an alkoxy group having from 1 to 10 carbon atoms, a silyl group having a hydrocarbon group having from 1 to 6 carbon atoms, an alkyl group having from 1 to 20 carbon atoms and substituted with a silyl group having a hydrocarbon group having from 1 to 6 carbon atoms, a group $—NR^{21}{}_2$, a group $—SR^{21}$, a group $—OSiR^{21}{}_3$ or a group $—PR^{21}{}_2$ (where $R^{21}$'s are the same or different, each representing a halogen atom, an alkyl group having from 1 to 10 carbon atom or an aryl group having from 6 to 20 carbon atoms), the neighboring groups of $R^1$ to $R^9$ and $R^{11}$ to $R^{19}$ may form one or more aromatic rings or aliphatic rings along with the atom bonding them, or $R^4$ and $R^5$, or $R^4$ and $R^9$, or $R^{14}$ and $R^{15}$, or $R^{14}$ and $R^{19}$ may form one aromatic ring or aliphatic ring along with the atom bonding them;

$R^{10}$ and $R^{20}$ are the same or different, each representing a hydrogen atom, a halogen atom, an alkyl group having from 1 to 10 carbon atoms, a fluoroalkyl group having from 1 to 10 carbon atoms, an alkoxy group having from 1 to 10 carbon atoms, an aryl group having from 6 to 20 carbon atoms, a fluoroaryl group having from 6 to 10 carbon atoms, an aryloxy group having from 6 to 10 carbon atoms, an alkenyl group having from 2 to 10 carbon atoms, an arylalkyl group having from 7 to 40 carbon atoms, an alkylaryl group having from 7 to 40 carbon atoms, or an arylalkenyl group having from 8 to 40 carbon atoms, provided that $R^{10}$ and $R^{20}$ are not hydrogen atoms at the same time, and $R^{10}$ and $R^{20}$ may form one or more rings along with the atom bonding them.]

In the general formula [I], M is a titanium atom, a zirconium atom or a hafnium atom, and is preferably zirconium or hafnium, more preferably hafnium.

$X^1$ and $X^2$ each represent a hydrogen atom, an alkyl group having from 1 to 10 carbon atoms, an alkoxy group having from 1 to 10 carbon atoms, an aryl group having from 6 to 20 carbon atoms, an aryloxy group having from 6 to 10 carbon atoms, an alkenyl group having from 2 to 10 carbon atoms, an arylalkyl group having from 7 to 40 carbon atoms, an alkylaryl group having from 7 to 40 carbon atoms, an arylalkenyl group having from 8 to 40 carbon atoms, an alkyl group having from 1 to 20 carbon atoms and substituted with a silyl group having a hydrocarbon group having from 1 to 6 carbon atoms, a substituted amino group having from 1 to 10 carbon atoms, a group OH or a halogen atom. Concretely, there are mentioned a chlorine atom, a bromine atom, an iodine atom, a fluorine atom, a methyl group, an ethyl group, a propyl group, an n-butyl group, an i-butyl group, a phenyl group, a benzyl group, a dimethylamino group, a diethylamino group, a trimethylsilylmethyl group, etc.

Concretely, especially preferred are a chlorine atom, a methyl group, an i-butyl group, a phenyl group, a benzyl group and a trimethylsilylmethyl group. Most preferred are a chlorine atom, a methyl group, an i-butyl group, a benzyl group and a trimethylsilylmethyl group.

Specific examples of the alkyl group having from 1 to 10 carbon atoms in the general formula [I] include methyl, ethyl, n-propyl, i-propyl, n-butyl, i-butyl, s-butyl, t-butyl, n-pentyl, n-hexyl, cyclopropyl, cyclopentyl, cyclohexyl, n-heptyl, n-octyl, n-decyl, etc.

The halogen atom of the halogenoalkyl group having from 1 to 10 carbon atoms includes a fluorine atom, a chlorine atom, a bromine atom, an iodine atom, etc., and the halogenoalkyl group having from 1 to 10 carbon atom is an alkyl group having from 1 to 10 carbon atom in which the hydrogen atom on the skeleton is substituted with a halogen.

Specific examples of the group include fluoromethyl, difluoromethyl, trifluoromethyl, chloromethyl, dichloromethyl, trichloromethyl, bromomethyl, dibromomethyl, tribromomethyl, iodomethyl, 2,2,2-trifluoroethyl, 2,2,1,1-tetrafluoroethyl, pentafluoroethyl, pentachloroethyl, pentafluoropropyl, nonafluorobutyl, 5-chloropentyl, 5,5,5-trichloropentyl, 5-fluoropentyl, 5,5,5-trifluoropentyl, 6-chlorohexyl, 6,6,6-trichlorohexyl, 6-fluorohexyl, 6,6,6-trifluorohexyl, etc.

The aryl group having from 6 to 20 carbon atoms concretely includes phenyl, 1-naphthyl, 2-naphthyl, acenaphthyl, phenanthryl, anthryl, etc.

The fluoroalkyl group having from 1 to 10 carbon atoms is an alkyl group having from 1 to 10 carbon atoms in which the hydrogen atom on the skeleton is substituted with a fluorine atom.

Specific examples of the group include fluoromethyl, difluoromethyl, trifluoromethyl, 2,2,2-trifluoroethyl, 2,2,1,1-tetrafluoroethyl pentafluoroethyl, pentafluoropropyl, 5-fluoropentyl, 5,5,5-trifluoropentyl, 6-fluorohexyl, 6,6,6-trifluorohexyl, etc.

Specific examples of the alkoxy group having from 1 to 10 carbon atoms include methoxy, ethoxy, n-propoxy, i-propoxy, n-butoxy, i-butoxy, s-butoxy, t-butoxy, n-pentoxy, n-hexoxy, cyclopropoxy, cyclopentoxy, cyclohexoxy, n-octoxy, n-decoxy, etc.

The fluoroaryl group having from 6 to 10 carbon atoms is an aryl group having from 6 to 10 carbon atoms in which the hydrogen atom on the skeleton is substituted with a fluorine atom. Specific examples of the group include pentafluorophenyl, 2-fluorophenyl, 3-fluorophenyl, 4-fluorophenyl, di(trifluoromethyl)phenyl, pentafluoroethylphenyl, nonafluoro-t-butylphenyl, 1-perfluoronaphthyl, 2-perfluoronaphthyl, etc.

The aryloxy group having from 6 to 10 carbon atoms may be substituted with a hydrocarbon group having from 1 to 4 carbon atoms, and specific examples of the group include phenoxy, trimethylphenoxy, dimethylphenoxy, ethyiphenoxy, t-butylphenoxy, 1-naphthoxy, 2-naphthoxy, etc.

The alkenyl group having from 2 to 10 carbon atoms concretely includes vinyl, 1-propenyl, 2-propenyl, 3-butenyl, 5-hexenyl, 7-octenyl, etc.

The arylalkyl group having from 7 to 40 carbon atoms concretely includes benzyl, phenylethyl, (methylphenyl)methyl, (tert-butylphenyl)methyl, etc.

The alkylaryl group having from 7 to 40 carbon atoms concretely includes tolyl, dimethylphenyl, ethylphenyl, trimethylphenyl, t-butylphenyl, etc.

The arylalkenyl group having from 8 to 40 carbon atoms concretely includes vinylphenyl, (2-propenyl)phenyl, etc.

The alkyl group having from 1 to 20 carbon atoms and substituted with a silyl group having a hydrocarbon group having from 1 to 6 carbon atoms concretely includes a trimethylsilylmethyl group, a triethylsilylmethyl group, a triphenylsilylmethyl group, etc.

The substituted amino group having from 1 to 10 carbon atoms concretely includes a dimethylamino group, a diethylamino group, a diisopropylamino group, etc.

The silyl group having a hydrocarbon group having from 1 to 6 carbon atoms concretely includes a trimethylsilyl group, a triethylsilyl group, a tert-butyl(dimethyl)silyl group, a triphenylsilyl group, etc.

A preferred group $R^{21}$ is an alkyl group having from 1 to 10 carbon atoms or an aryl group having from 6 to 10 carbon atoms; and a preferred group $—NR^{21}_2$ concretely includes a dimethyl amino group, a diethylamino group, a diisopropylamino group, etc.

The group $—SR^{21}$ concretely includes a methylsulfanyl group, an ethylsulfanyl group, an isopropylsulfanyl group, a phenylsulfanyl group, etc.

The group $—OSiR^{21}_3$ concretely includes a trimethylsiloxy group, a triethylsiloxy group, a triisopropylsiloxy group, a triphenylsiloxy group, a tert-butyl(dimethyl)siloxy group, etc.

The group $—PR^{21}_2$ concretely includes a dimethylphosphino group, a diethylphosphino group, a diisopropylphosphino group, a dibutylphosphino group, a diphenylphosphino group, etc.

Preferably, $R^1$, $R^2$, $R^3$, $R^4$, $R^{11}$, $R^{12}$, $R^{13}$ and $R^{14}$ are hydrogen atoms.

Preferably, $R^5$, $R^6$, $R^7$, $R^8$, $R^9$, $R^{15}$, $R^{16}$, $R^{17}$, $R^{18}$ and $R^{19}$ are each independently a hydrogen atom, an alkyl group having from 1 to 10 carbon atoms, a halogenoalkyl group having from 1 to 10 carbon atoms, an aryl group having from 6 to 10 carbon atoms, a silyl group having a hydrocarbon group having from 1 to 6 carbon atoms, or an alkyl group having from 1 to 20 carbon atoms and substituted with a silyl group having a hydrocarbon group having from 1 to 6 carbon atoms, more preferably a hydrogen atom, an alkyl group having from 1 to 10 carbon atoms, a halogenoalkyl group having from 1 to 10 carbon atoms, or an aryl group having from 6 to 10 carbon atoms. Preferably, $R^5$ to $R^9$ and $R^{15}$ to $R^{19}$ are not hydrogen atoms at the same time.

Preferably, $R^{10}$ and $R^{20}$ each are a halogen atom, an alkyl group having from 1 to 10 carbon atoms, a fluoroalkyl group having from 1 to 10 carbon atoms, an aryl group having from 7 to 10 carbon atoms, a fluoroaryl group having from 6 to 10 carbon atoms, an alkenyl group having from 2 to 10 carbon atoms, an arylalkyl group having from 7 to 40 carbon atoms, an alkylaryl group having from 7 to 40 carbon atoms, or an arylalkenyl group having from 8 to 40 carbon atoms, more preferably an alkyl group having from 1 to 10 carbon atoms, an aryl group having from 7 to 10 carbon atoms or an alkenyl group having from 2 to 10 carbon atoms, and in addition, the total of the carbon atoms that $R^{10}$ and $R^{20}$ have is 2 or more. Also preferably, $R^{10}$ and $R^{20}$ form one or more rings along with the atom bonding them, more preferably form a 4- to 5-membered ring.

Specific Examples of Metallocene Compound:

Specific examples of the metallocene compound of the present invention are shown below. These are typical exemplifications.

Isopropylidene-Bridged Metallocene Compounds
Isopropylidenebis(4-phenyl-1-indenyl)dimethylhafnium
Isopropylidenebis(4-(3-methylphenyl)-1-indenyl)dimethylhafnium
Isopropylidenebis(4-(3-isopropylphenyl)-1-indenyl)dimethylhafnium
Isopropylidenebis(4-(3-tert-butylphenyl)-1-indenyl)dimethylhafnium Isopropylidenebis(4-(4-methylphenyl)-1-indenyl)dimethylhafnium
Isopropylidenebis(4-(4-isopropylphenyl)-1-indenyl)dimethylhafnium
Isopropylidenebis(4-(4-tert-butylphenyl)-1-indenyl)dimethylhafnium
Isopropylidenebis(4-(4-trifluoromethylphenyl)-1-indenyl)dimethylhafnium
Isopropylidenebis(4-(4-methoxyphenyl)-1-indenyl)dimethylhafnium
Isopropylidenebis(4-(4-isopropoxyphenyl)-1-indenyl)dimethylhafnium
Isopropylidenebis(4-(4-trimethylsilylphenyl)-1-indenyl)dimethylhafnium
Isopropylidenebis(4-(4-fluorophenyl)-1-indenyl)dimethylhafnium
Isopropylidenebis(4-(4-chlorophenyl)-1-indenyl)dimethylhafnium
Isopropylidenebis(4-(4-bromophenyl)-1-indenyl)dimethylhafnium
Isopropylidenebis(4-(2-methylphenyl)-1-indenyedimethylhafnium
Isopropylidenebis(4-(2-ethylphenyl)-1-indenyl)dimethylhafnium
Isopropylidenebis(4-(3,5-dimethylphenyl)-1-indenyedimethylhafnium
Isopropylidenebis(4-(3,5-diisopropylphenyl)-1-indenyl)dimethylhafnium
Isopropylidenebis(4-(3,5-di-tert-butylphenyl)-1-indenyl)dimethylhafnium
Isopropylidenebis(4-(3,5-dimethoxyphenyl)-1-indenyl)dimethylhafnium
Isopropylidenebis(4-(3,5-ditrimethylsilylphenyl)-1-indenyl)dimethylhafnium
Isopropylidenebis(4-(3 ditrifluromethylphenyl)-1-indenyl)dimethylhafnium
Isopropyldenebis(4-(2,3-dimethylphenyl)-1-indenyl)dimethylhafnium
Isopropylidenebis(4-(2,5-dimethylphenyl)-1-indenyl)dimethylhafnium
Isopropylidenebis(4-(2,6-dimethylphenyl)-1-indenyl)dimethylhafnium
Isopropylidenebis(4-(2,3,5,6-tetramethylphenyl)-1-indenyl)dimethylhafnium
Isopropyldenebis(4-(2,3,4,5,6-pentamethylphenyl)-1-indenyl)dimethylhafnium
Isopropylidenebis(4-(4-tert-butyl-2-methyl-phenyl)-1-indenyl)dimethylhafnium
Isopropylidenebis(4-biphenyl-1-indenyl)dimethylhafnium
Isopropylidenebis(4-(2,6-dimethylbiphenylyl)-1-indenyl)dimethylhafnium
Isopropylidenebis(4-(2',6'-dimethylbiphenylyl)-1-indenyl)dimethylhafnium
isopropylidenebis(4-(1-naphthyl)-1-indenyl)dimethylhafnium
Isopropylidenebis(4-(2-naphthyl)-1-indenyl)dimethylhafnium
Isopropylidenebis(4-phenanthryl-1-indenyl)dimethylhafnium
Cyclobutylidene-Bridged Metallocene Compounds
Cyclobutylidenebis(4-phenyl-1-indenyl)dimethylhafnium
Cyclobutylidenebis(4-(3-methylphenyl)-1-indenyl)dimethylhafnium
Cyclobutylidenebis(4-(3-isopropylphenyl)-1-indenyl)dimethylhafnium
Cyclobutylidenebis(4-(3-tert-butylphenyl)-1-indenyl)dimethylhafnium
Cyclobutylidenebis(4-(4-methylphenyl)-1-indenyl)dimethylhafnium
Cyclobutylidenebis(4-(4-isopropylphenyl)-1-indenyl)dimethylhafnium
Cyclobutylidenebis(4-(4-tert-butylphenyl)-1-indenyl)dimethylhafnium
Cyclobutylidenebis(4-(4-trifluoromethylphenyl)-1-indenyl)dimethylhafnium
Cyclobutylidenebis(4-(4-methoxyphenyl)-1-indenyl)dimethylhafnium
Cyclobutylidenebis(4-(4-isopropoxyphenyl)-1-indenyl)dimethylhafnium
Cyclobutylidenebis(4-(4-trimethylsilylphenyl)-1-indenyl)dimethylhafnium
Cyclobutylidenebis(4-(4-fluorophenyl)-1-indenyl)dimethylhafnium
Cyclobutylidenebis(4-(4-chlorophenyl)-1-indenyl)dimethylhafnium
Cyclobutylidenebis(4-(4-bromophenyl)-1-indenyl)dimethylhafnium
Cyclobutylidenebis(4-(2-methylphenyl)-1-indenyl)dimethylhafnium
Cyclobutylidenebis(4-(2-ethylphenyl)-1-indenyl)dimethylhafnium
Cyclobutylidenebis(4-(3,5-dimethylphenyl)-1-indenyedimethylhafnium
Cyclobutylidenebis(4-(3,5-diisopropylphenyl)-1-indenyedimethylhafnium
Cyclobutylidenebis(4-(3,5-di-tert-butylphenyl)-1-indenyl)dimethylhafnium
Cyclobutylidenebis(4-(3,5-dimethoxyphenyl)-1-indenyl)dimethylhafnium
Cyclobutylidenebis(4-(3,5-ditrimethylsilylphenyl)-1-indenyl)dimethylhafnium
Cyclobutylidenebis(4-(3,5-ditrifluoromethylphenyl)-1-indenyl)dimethylhafnium
Cyclobutylidenebis(4-(2,3-dimethylphenyl)-1-indenyl)dimethylhafnium
Cyclobutylidenebis(4-(2,5-dimethylphenyl)-1-indenyl)dimethylhafnium
Cyclobutylidenebis(4-(2,6-dimethylphenyl)-1-indenyl)dimethylhafnium
Cyclobutylidenebis(4-(2,3,5,6-tetramethylphenyl)-1-indenyl)dimethylhafnium
Cyclobutylidenebis(4-(2,3,4,5,6-pentamethylphenyl)-1-indenyl)dimethylhafnium
Cyclobutylidenebis(4-(4-tert-butyl-2-methyl-phenyl)-1-indenyl)dimethylhafnium
Cyclobutylidenebis(4-biphenyl-1-indenyl)dimethylhafnium
Cyclobutylidenebis(4-(2,6-dimethylbiphenylyl)-1-indenyl)dimethylhafnium
Cyclobutylidenebis(4-(2',6'-dimethylbiphenylyl)-1-indenyl)dimethylhafnium
Cyclobutylidenebis(4-(1-naphthyl)-1-indenyl)dimethylhafnium
Cyclobutylidenebis(4-(2-naphthyl)-1-indenyl)dimethylhafnium
Cyclobutylidenebis(4-phenanthryl-1-indenyl)dimethylhafnium
Cyclopentylidene-Bridged Metallocene Compounds
Cyclopentylidenebis(4-phenyl-1-indenyl)dimethylhafnium
Cyclopentylidenebis(4-(3-methylphenyl)-1-indenyl)dimethylhafnium
Cyclopentylidenebis(4-(3-isopropylphenyl)-1-indenyl)dimethylhafnium
Cyclopentylidenebis(4-(3-tert-butylphenyl)-1-indenyedimethylhafnium Cyclopentylidenebis(4-(4-methylphenyl)-1-indenyl)dimethylhafnium
Cyclopentylidenebis(4-(4-isopropylphenyl)-1-indenyl)dimethylhafnium
Cyclopentylidenebis(4-(4-tert-butylphenyl)-1-indenyl)dimethylhafnium
Cyclopentylidenebis(4-(4-trifluoromethylphenyl)-1-indenyl)dimethylhafnium
Cyclopentylidenebis(4-(4-methoxyphenyl)-1-indenyl)dimethylhafnium
Cyclopentylidenebis(4-(4-isopropoxyphenyl)-1-indenyl)dimethylhafnium
Cyclopentylidenebis(4-(4-trimethylsilylphenyl)-1-indenyl)dimethylhafnium
Cyclopentylidenebis(4-(4-fluorophenyl)-1-indenyl)dimethylhafnium
Cyclopentylidenebis(4-(4-chlorophenyl)-1-indenyl)dimethylhafnium
Cyclopentylidenebis(4-(4-bromophenyl)-1-indenyl)dimethylhafnium
Cyclopentylidenebis(4-(2-methylphenyl)-1-indenyl)dimethylhafnium
Cyclopentylidenebis(4-(2-ethylphenyl)-1-indenyl)dimethylhafnium
Cyclopentylidenebis(4-(3,5-dimethylphenyl)-1-indenyl)dimethylhafnium
Cyclopentylidenebis(4-(3,5-diisopropylphenyl)-1-indenyl)dimethylhafnium
Cyclopentylidenebis(4-(3,5-di-tert-butylphenyl)-1-indenyl)dimethylhafnium
Cyclopentylidenebis(4-(3,5-dimethoxyphenyl)-1-indenyl)dimethylhafnium
Cyclopentylidenebis(4-(3,5-ditrimethoxysilylphenyl)-1-indenyl)dimethylhafnium
Cyclopentylidenebis(4-(3,5-ditrifluoromethylphenyl)-1-indenyl)dimethylhafnium
Cyclopentylidenebis(4-(2,3-dimethylphenyl)-1-indenyl)dimethylhafnium
Cyclopentylidenebis(4-(2,5-dimethylphenyl)-1-indenyl)dimethylhafnium
Cyclopentylidenebis(4-(2,6-dimethylphenyl)-1-indenyl)dimethylhafnium
Cyclopentylidenebis(4-(2,3,5,6-tetramethylphenyl)-1-indenyl)dimethylhafnium
Cyclopentylidenebis(4-(2,3,4,5,6-pentamethylphenyl)-1-indenyl)dimethylhafnium
Cyclopentylidenebis(4-(4-tert-butyl-2-methylphenyl)-1-indenyl)dimethylhafnium
Cyclopentylidenebis(4-biphenylyl-1-indenyl)dimethylhafnium
Cyclopentylidenebis(4-(2,6-dimethylbiphenylyl)-1-indenyl)dimethylhafnium
Cyclopentylidenebis(4-(2',6'-dimethylbiphenylyl)-1-indenyl)dimethylhafnium
Cyclopentylidenebis(4-(1-naphthyl)-1-indenyl)dimethylhafnium
Cyclopentylidenebis(4-(2-naphthyl)-1-indenyl)dimethylhafnium
Cyclopentylidenebis(4-phenanthryl-1-indenyl)dimethylhafnium
Cyclohexylidene-Bridged Metallocene Compounds
Cyclohexylidenebis(4-phenyl-1-indenyl)dimethylhafnium
Cyclohexylidenebis(4-(3-methylphenyl)-1-indenyl)dimethylhafnium
Cyclohexylidenebis(4-(3-isopropylphenyl)-1-indenyl)dimethylhafnium
Cyclohexylidenebis(4-(3-tert-butylphenyl)-1-indenyl)dimethylhafnium
Cyclohexylidenebis(4-(4-methylphenyl)-1-indenyl)dimethylhafnium
Cyclohexylidenebis(4-(4-isopropylphenyl)-1-indenyl)dimethylhafnium
Cyclohexylidenebis(4-(4-tert-butylphenyl)-1-indenyl)dimethylhafnium
Cyclohexylidenebis(4-(4-trimethylphenyl)-1-indenyl)dimethylhafnium
Cyclohexylidenebis(4-(2-methylphenyl)-1-indenyl)dimethylhafnium
Cyclohexylidenebis(4-(2-ethylphenyl)-1-indenyedimethylhafnium
Cyclohexylidenebis(4-(3,5-dimethylphenyl)-1-indenyl)dimethylhafnium
Cyclohexylidenebis(4-(3,5-di-tert-butylphenyl)-1-indenyl)dimethylhafnium
Cyclohexylidenebis(4-(3,5-di-trimethylsilylphenyl)-1-indenyedimethylhafnium
Cyclohexylidenebis(4-(2,3-dimethylphenyl)-1-indenyl)dimethylhafnium
Cyclohexylidenebis(4-(2,5-dimethylphenyl)-1-indenyl)dimethylhafnium
Cyclohexylidenebis(4-(2,6-dimethylphenyl)-1-indenyl)dimethylhafnium
Cyclohexylidenebis(4-(4-terg-butyl-2-methylphenyl)-1-indenyl)dimethylhafnium
Cyclohexylidenebis(4-biphenylyl-1-indenyl)dimethylhafnium
Diethylmethylene-Bridged Metallocene Compounds
Diethylmethylenebis(4-phenyl-1-indenyl)dimethylhafnium
Diethylmethylenebis(4-(3-methylphenyl)-1-indenyl)dimethylhafnium
Diethylmethylenebis(4-(3-isopropylphenyl)-1-indenyl)dimethylhafnium
Diethylmethylenebis(4-(3-tert-butylphenyl)-1-indenyl)dimethylhafnium
Diethylmethylenebis(4-(4-methylphenyl)-1-indenyl)dimethylhafnium
Diethylmethylenebis(4-(4-isopropylphenyl)-1-indenyl)dimethylhafnium
Diethylmethylenebis(4-(4-tert-butylphenyl)-1-indenyl)dimethylhafnium
Diethylmethylenebis(4-(4-trimethylsilylphenyl)-1-indenyl)dimethylhafnium
Diethylmethylenebis(4-(2-methylphenyl)-1-indenyl)dimethylhafnium
Diethylmethylenebis(4-(2-ethylphenyl)-1-indenyl)dimethylhafnium
Diethylmethylenebis(4-(3,5-dimethylphenyl)-1-indenyedimethylhafnium
Diethylmethylenebis(4-(3,5-di-tert-butylphenyl)-1-indenyl)dimethylhafnium
Diethylmethylenebis(4-(3,5-ditrimethylsilylphenyl)-1-indenyl)dimethylhafnium
Diethylmethylenebis(4-(2,3-dimethylphenyl)-1-indenyedimethylhafnium
Diethylmethylenebis(4-(2,5-dimethylphenyl)-1-indenyl)dimethylhafnium
Diethylmethylenebis(4-(2,6-dimethylphenyl)-1-indenyl)dimethylhafnium
Diethylmethylenebis(4-(4-tert-butyl-2-methylphenyl)-1-indenyl)dimethylhafnium
Diethylmethylenebis(4-biphenylyl-1-indenyl)dimethylhafnium
Di-n-propylmethylene-Bridged Metallocene Compounds Di-n-propylmethylenebis(4-phenyl-1-indenyl)dimethylhafnium
Di-n-propylmethylenebis(4-(3-methylphenyl)-1-indenyl)dimethylhafnium
Di-n-propylmethylenebis(4-(3-isopropylphenyl)-1-indenyl)dimethylhafnium
Di-n-propylmethylenebis(4-(3-tert-butylphenyl)-1-indenyl)dimethylhafnium
Di-n-propylmethylenebis(4-(4-methylphenyl)-1-indenyl)dimethylhafnium
Di-n-propylmethylenebis(4-(4-isopropylphenyl-1-indenyl)dimethylhafnium
Di-n-propylmethylenebis(4-(4-tert-butylphenyl)-1-indenyl)dimethylhafnium
Di-n-propylmethylenebis(4-(4-trimethylsilylphenyl)-1-indenyl)dimethylhafnium
Di-n-propylmethylenebis(4-(2-methylphenyl)-1-indenyl)dimethylhafnium
Di-n-propylmethylenebis(4-(2-ethylphenyl)-1-indenyl)dimethylhafnium
Di-n-propylmethylenebis(4-(3,5-dimethylphenyl)-1-indenyl)dimethylhafnium
Di-n-propylmethylenebis(4-(3,5-di-tert-butylphenyl)-1-indenyl)dimethylhafnium
Di-n-propylmethylenebis(4-(3,5-ditrimethylsilylphenyl)-1-indenyl)dimethylhafnium
Di-n-propylmethylenebis(4-(2,3-dimethylphenyl)-1-indenyl)dimethylhafnium
Di-n-propylmethylenebis(4-(2,5-dimethylphenyl)-1-indenyl)dimethylhafnium
Di-n-propylmethylenebis(4-(2,6-dimethylphenyl)-1-indenyl)dimethylhafnium
Di-n-propylmethylenebis(4-(4-tert-butyl-2-methylphenyl)-1-indenyl)dimethylhafnium
Di-n-propylmethylenebis(4-biphenylyl-1-indenyl)dimethylhafnium
Di-iso-butylmethylene-Bridged Metallocene Compounds
Di-iso-butylmethylenebis(4-phenyl-1-indenyl)dimethylhafnium
Di-iso-butylmethylenebis(4-(3-methylphenyl)-1-indenyl)dimethylhafnium
Di-iso-butylmethylenebis(4-(3-isopropylphenyl)-1-indenyl)dimethylhafnium
Di-iso-butylmethylenebis(4-(3-tert-butylphenyl)-1-indenyl)dimethylhafnium
Di-iso-butylmethylenebis(4-(4-methylphenyl)-1-indenyl)dimethylhafnium
Di-iso-butylmethylenebis(4-(4-isopropylphenyl)-1-indenyl)dimethylhafnium
Di-iso-butylmethylenebis(4-(4-tert-butylphenyl)-1-indenyl)dimethylhafnium
Di-iso-butylmethylenebis(4-(4-trimethylsilylphenyl)-1-indenyedimethylhafnium
Di-iso-butylmethylenebis(4-(2-methylphenyl)-1-indenyl)dimethylhafnium
Di-iso-butylmethylenebis(4-(2-ethylphenyl)-1-indenyl)dimethylhafnium
Di-iso-butylmethylenebis(4-(3,5-dimethylphenyl)-1-indenyl)dimethylhafnium
Di-iso-butylmethylenebis(4-(3,5-di-tert-butylphenyl)-1-indenyl)dimethylhafnium
Di-iso-butylmethylenebis(4-(3,5-ditrimethylsilylphenyl)-1-indenyl)dimethylhafnium
Di-iso-butylmethylenebis(4-(2,3-dimethylphenyl)-1-indenyl)dimethylhafnium
Di-iso-butylmethylenebis(4-(2,5-dimethylphenyl)-1-indenyl)dimethylhafnium
Di-iso-butylmethylenebis(4-(2,6-dimethylphenyl)-1-indenyl)dimethylhafnium
Di-iso-butylmethylenebis(4-(4-tert-butyl-2-methylphenyl)-1-indenyl)dimethylhafnium
Di-iso-butylmethylenebis(4-biphenylyl-1-indenyl)dimethylhafnium
Dibenzylmethylene-Bridged Metallocene Compounds
Dibenzylmethylenebis(4-phenyl-1-indenyl)dimethylhafnium
Dibenzylmethylenebis(4-(3-methylphenyl)-1-indenyl)dimethylhafnium
Dibenzylmethylenebis(4-(3-isopropylphenyl)-1-indenyl)dimethylhafnium
Dibenzylmethylenebis(4-(3-tert-butylphenyl)-1-indenyl)dimethylhafnium
Dibenzylmethylenebis(4-(4-methylphenyl)-1-indenyl)dimethylhafnium
Dibenzylmethylenebis(4-(4-isopropylphenyl)-1-indenyl)dimethylhafnium
Dibenzylmethylenebis(4-(4-tert-butylphenyl)-1-indenyl)dimethylhafnium
Dibenzylmethylenebis(4-(4-trimethylsilylphenyl)-1-indenyl)dimethylhafnium
Dibenzylmethylenebis(4-(2-methylphenyl)-1-indenyl)dimethylhafnium
Dibenzylmethylenebis(4-(2-ethylphenyl)-1-indenyl)dimethylhafnium
Dibenzylmethylenebis(4-(3,5-dimethylphenyl)-1-indenyl)dimethylhafnium
Dibenzylmethylenebis(4-(3,5-di-tert-butylphenyl)-1-indenyl)dimethylhafnium
Dibenzylmethylenebis(4-(3,5-ditrimethylsilylphenyl)-1-indenyl)dimethylhafnium
Dibenzylmethylenebis(4-(2,3-dimethylphenyl)-1-indenyl)dimethylhafnium
Dibenzylmethylenebis(4-(2,5-dimethylphenyl)-1-indenyl)dimethylhafnium
Dibenzylmethylenebis(4-(2,6-dimethylphenyl)-1-indenyl)dimethylhafnium
Dibenzylmethylenebis(4-(4-tert-butyl-2-methylphenyl)-1-indenyl)dimethylhafnium
Dibenzylmethylenebis(4-biphenylyl-1-indenyl)dimethylhafnium
Methyl(ethyl)methylene-Bridged Metallocene Compounds
Methyl(ethyl)methylenebis(4-phenyl-1-indenyl)dimethyl hafnium
Methyl(ethyl)methylenebis(4-(3-methylphenyl)-1-indenyedimethylhafnium
Methyl(ethyl)methylenebis(4-(3-isopropylphenyl)-1-indenyl)dimethylhafnium
Methyl(ethyl)methylenebis(4-(3-tert-butylphenyl)-1-indenyl)dimethylhafnium
Methyl(ethyl)methylenebis(4-(4-methylphenyl)-1-indenyl) dimethyl hafnium
Methyl(ethyl)methylenebis(4-(4-isopropylphenyl)-1-indenyl)dimethylhafnium
Methyl(ethyl)methylenebis(4-(4-tert-butylphenyl)-1-indenyl)dimethylhafnium
Methyl(ethyl)methylenebis(4-(4-trimethylsilylphenyl)-1-indenyl)dimethylhafnium
Methyl(ethyl)methylenebis(4-(2-methylphenyl)-1-indenyl) dimethylhafnium
Methyl(ethyl)methylenebis(4-(2-ethylphenyl)-1-indenyl)dimethylhafnium
Methyl(ethyl)methylenebis(4-(3,5-dimethylphenyl)-1-indenyl)dimethylhafnium Methyl(ethyl)methylenebis(4-(3,5-di-tert-butylphenyl)-1-indenyl)dimethylhafnium
Methyl(ethyl)methylenebis(4-(3,5-ditrimethylsilylphenyl)-1-indenyedimethylhafnium
Methyl(ethyl)methylenebis(4-(2,3-dimethylphenyl)-1-indenyl)dimethylhafnium
Methyl(ethyl)methylenebis(4-(2,5-dimethylphenyl)-1-indenyl)dimethylhafnium
Methyl(ethyl)methylenebis(4-(2,6-dimethylphenyl)-1-indenyl)dimethylhafnium
Methyl(ethyl)methylenebis(4-(4-tert-butyl-2-methylphenyl)-1-indenyl)dimethylhafnium
Methyl(ethyl)methylenebis(4-biphenylyl-1-indenyl)dimethylhafnium
Methyl(n-propyl)methylene-Bridged Metallocene Compounds
Methyl(n-propyl)methylenebis(4-phenyl-1-indenyl)dimethylhafnium
Methyl(n-propyl)methylenebis(4-(3-methylphenyl)-1-indenyl)dimethylhafnium
Methyl(n-propyl)methylenebis(4-(3-isopropylphenyl)-1-indenyl)dimethylhafnium
Methyl(n-propyl)methylenebis(4-(3-tert-butylphenyl)-1-indenyl)dimethylhafnium
Methyl(n-propyl)methylenebis(4-(4-methylphenyl)-1-indenyl)dimethylhafnium
Methyl(n-propyl)methylenebis(4-(4-isopropylphenyl)-1-indenyl)dimethylhafnium
Methyl(n-propyl)methylenebis(4-(4-tert-butylphenyl)-1-indenyl)dimethylhafnium
Methyl(n-propyl)methylenebis(4-(4-trimethylsilylphenyl)-1-indenyl)dimethylhafnium
Methyl(n-propyl)methylenebis(4-(2-methylphenyl)-1-indenyl)dimethylhafnium
Methyl(n-propyl)methylenebis(4-(2-ethylphenyl)-1-indenyl)dimethylhafnium
Methyl(n-propyl)methylenebis(4-(3,5-dimethylphenyl)-1-indenyl)dimethylhafnium
Methyl(n-propyl)methylenebis(4-(3,5-di-tert-butylphenyl)-1-indenyl)dimethylhafnium
Methyl(n-propyl)methylenebis(4-(3,5-ditrimethylsilylphenyl)-1-indenyedimethylhafnium
Methyl(n-propyl)methylenebis(4-(2,3-dimethylphenyl)-1-indenyl)dimethylhafnium
Methyl(n-propyl)methylenebis(4-(2,5-dimethylphenyl)-1-indenyl)dimethylhafnium
Methyl(n-propyl)methylenebis(4-(2,6-dimethylphenyl)-1-indenyl)dimethylhafnium
Methyl(n-propyl)methylenebis(4-(4-tert-butyl-2-methylphenyl)-1-indenyl)dimethylhafnium
Methyl(n-propyl)methylenebis(4-biphenylyl-1-indenyl)dimethylhafnium
Methyl(iso-butyl)methylene-Bridged Metallocene Compound
Methyl(iso-butyl)methylenebis(4-phenyl-1-indenyl)dimethylhafnium
Methyl(iso-butyl)methylenebis(4-(3-methylphenyl)-1-indenyl)dimethylhafnium
Methyl(iso-butyl)methylenebis(4-(3-isopropylphenyl)-1-indenyl)dimethylhafnium
Methyl(iso-butyl)methylenebis(4-(3-tert-butylphenyl)-1-indenyl)dimethylhafnium
Methyl(iso-butyl)methylenebis(4-(4-methylphenyl)-1-indenyl)dimethylhafnium
Methyl(iso-butyl)methylenebis(4-(4-isopropylphenyl)-1-indenyl)dimethylhafnium
Methyl(iso-butyl)methylenebis(4-(4-tert-butylphenyl)-1-indenyl)dimethylhafnium
Methyl(iso-butyl)methylenebis(4-(4-trimethylsilylphenyl)-1-indenyl)dimethylhafnium
Methyl(iso-butyl)methylenebis(4-(2-methylphenyl)-1-indenyl)dimethylhafnium
Methyl(iso-butyl)methylenebis(4-(2-ethylphenyl)-1-indenyl)dimethylhafnium
Methyl(iso-butyl)methylenebis(4-(3,5-dimethylphenyl)-1-indenyedimethylhafnium
Methyl(iso-butyl)methylenebis(4-(3,5-di-tert-butylphenyl)-1-indenyl)dimethylhafnium
Methyl(iso-butyl)methylenebis(4-(3,5-ditrimethylsilylphenyl)-1-indenyl)dimethylhafnium
Methyl(iso-butyl)methylenebis(4-(2,3-dimethylphenyl)-1-indenyl)dimethylhafnium
Methyl(iso-butyl)methylenebis(4-(2,5-dimethylphenyl)-1-indenyl)dimethylhafnium
Methyl(iso-butyl)methylenebis(4-(2,6-dimethylphenyl)-1-indenyedimethylhafnium
Methyl(iso-butyl)methylenebis(4-(4-tert-butyl-2-methylphenyl)-1-indenyl)dimethylhafnium
Methyl(iso-butyl)methylenebis(4-biphenylyl-1-indenyl)dimethylhafnium
Methyl(benzyl)methylene-Bridged Metallocene Compounds
Methyl(benzyl)methylenebis(4-phenyl-1-indenyl)dimethylhafnium
Methyl(benzyl)methylenebis(4-(3-methylphenyl)-1-indenyl)dimethylhafnium
Methyl(benzyl)methylenebis(4-(3-isopropylphenyl)-1-indenyl)dimethylhafnium
Methyl(benzyl)methylenebis(4-(3-tert-butylphenyl)-1-indenyedimethylhafnium
Methyl(benzyl)methylenebis(4-(4-methylphenyl)-1-indenyedimethylhafnium
Methyl(benzyl)methylenebis(4-(4-isopropylphenyl)-1-indenyl)dimethylhafnium
Methyl(benzyl)methylenebis(4-(4-tert-butylphenyl)-1-indenyl)dimethylhafnium
Methyl(benzyl)methylenebis(4-(4-trimethylsilylphenyl)-1-indenyl)dimethylhafnium
Methyl(benzyl)methylenebis(4-(2-methylphenyl)-1-indenyl)dimethylhafnium
Methyl(benzyl)methylenebis(4-(2-ethylphenyl)-1-indenyl)dimethylhafnium
Methyl(benzyl)methylenebis(4-(3,5-dimethylphenyl)-1-indenyl)dimethylhafnium
Methyl(benzyl)methylenebis(4-(3,5-di-tert-butylphenyl)-1-indenyl)dimethylhafnium
Methyl(benzyl)methylenebis(4-(3,5-ditrimethylsilylphenyl)-1-indenyl)dimethylhafnium
Methyl(benzyl)methylenebis(4-(2,3-dimethylphenyl)-1-indenyl)dimethylhafnium
Methyl(benzyl)methylenebis(4-(2,5-dimethylphenyl)-1-indenyl)dimethylhafnium
Methyl(benzyl)methylenebis(4-(2,6-dimethylphenyl)-1-indenyl)dimethylhafnium
Methyl(benzyl)methylenebis(4-(4-tert-butyl-2-methylphenyl)-1-indenyl)dimethylhafnium
Methyl(benzyl)methylenebis(4-biphenylyl-1-indenyl)dimethylhafnium
Di(4-methylphenyl)methylene-Bridged Metallocene Compounds
Di(4-methylphenyl)methylenebis(4-phenyl-1-indenyl)dimethylhafnium Di(4-methylphenyl)methylenebis(4-(3-methylphenyl)-1-indenyl)dimethylhafnium
Di(4-methylphenyl)methylenebis(4-(3-isopropylphenyl)-1-indenyl)dimethylhafnium
Di(4-methylphenyl)methylenebis(4-(3-tert-butylphenyl)-1-indenyl)dimethylhafnium
Di(4-methylphenyl)methylenebis(4-(4-methylphenyl)-1-indenyl)dimethylhafnium
Di(4-methylphenyl)methylenebis(4-(4-isopropylphenyl)-1-indenyl)dimethylhafnium
Di(4-methylphenyl)methylenebis(4-(4-tert-butylphenyl)-1-indenyl)dimethylhafnium
Di(4-methylphenyl)methylenebis(4-(4-trimethylsilylphenyl)-1-indenyl)dimethylhafnium
Di(4-methylphenyl)methylenebis(4-(2-methylphenyl)-1-indenyl)dimethylhafnium
Di(4-methylphenyl)methylenebis(4-(2-ethylphenyl)-1-indenyl)dimethylhafnium
Di(4-methylphenyl)methylenebis(4-(3,5-dimethylphenyl)-1-indenyl)dimethylhafnium
Di(4-methylphenyl)methylenebis(4-(3,5-di-tert-butylphenyl)-1-indenyl)dimethylhafnium
Di(4-methylphenyl)methylenebis(4-(3,5-ditrimethylsilylphenyl)-1-indenyl)dimethylhafnium
Di(4-methylphenyl)methylenebis(4-(2,3-dimethylphenyl)-1-indenyl)dimethylhafnium
Di(4-methylphenyl)methylenebis(4-(2,5-dimethylphenyl)-1-indenyl)dimethylhafnium
Di(4-methylphenyl)methylenebis(4-(2,6-dimethylphenyl)-1-indenyedimethylhafnium
Di(4-methylphenyl)methylenebis(4-(4-tert-butyl-2-methylphenyl)-1-indenyl)dimethylhafnium
Di(4-methylphenyl)methylenebis(4-biphenylyl-1-indenyl)dimethylhafnium In addition to the above, there are further exemplified compounds derived from the above-exemplified compounds, in which M is titanium or zirconium in place of hafnium; and compounds in which either one or both of $X^1$ and $X^2$ is/are a chlorine atom, a bromine atom, an iodine atom, a phenyl group, a benzyl group, a dimethylamino group, a diethylamino group, a trimethylsilyl group or the like in place of the methyl group in the above-exemplified compounds.

Synthesis Method for Metallocene Compounds

The metallocene compound of the present may be synthesized in any method depending on the substituents and the bonding modes therein. One typical example of a synthesis route is shown below.

[Chem. 3]

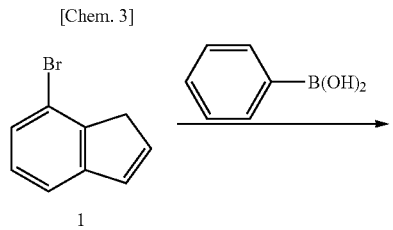

1

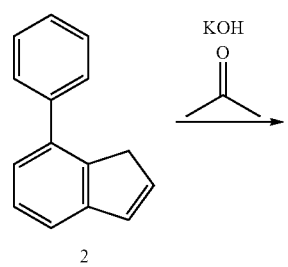

2

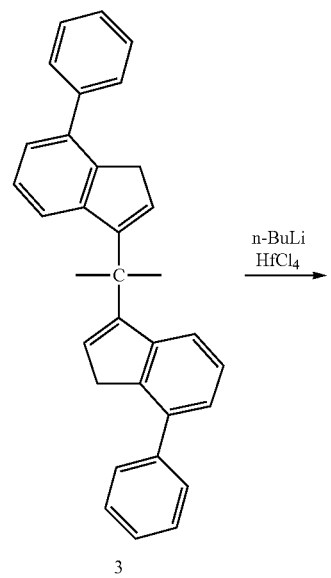

3

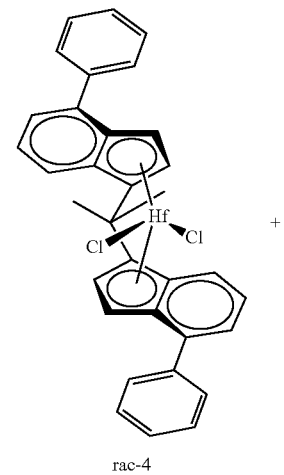

rac-4

-continued

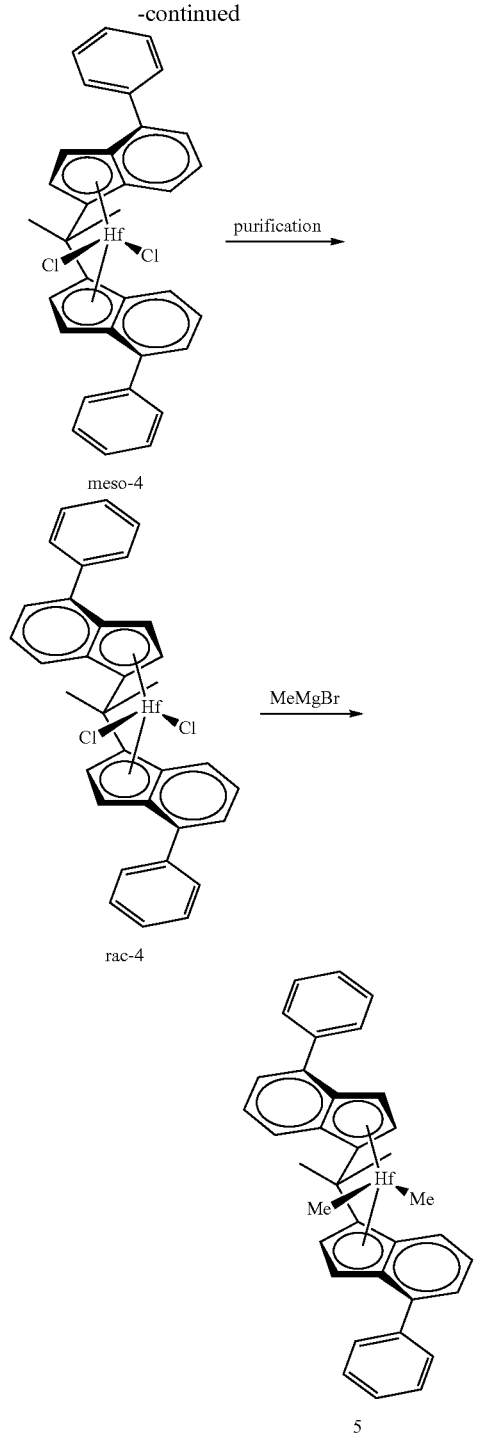

meso-4 rac-4

5

In the above-mentioned synthesis route, the compound 1 is coupled with phenylboronic acid in the presence of a palladium catalyst to give the compound 2. The compound 2 may be bridged to give the compound 3 according to a method described in a publication (Japanese Patent 3835846) or the like. The compound 2 may be anionized with potassium hydroxide and then reacted with acetone to give the compound 3. The compound 3 may be dianionized with 2 equivalents of n-butyllithium or the like, and then reacted with hafnium tetrachloride to give the metallocene compound 4. In general, the metallocene compound 4 is obtained as a mixture of a racemic form and a meso form thereof, and the racemic form excellent in catalytic potency is concentration through purification. In addition, according to a method described in a publication (WO2000/017213), the meso form may be isomerized into the racemic form to increase the yield of the racemic form. The dimethyl form 5 may be obtained by processing the metallocene compound 4 with 2 equivalents or more of MeMgBr or the like.

A substituted metallocene compound may be synthesized, using a correspondingly-substituted material. Using a correspondingly-substituted boronic acid, for example, 4-isopropylphenylboronic acid, 3,5-dimethylphenylboronic acid or the like in place of phenylboronic acid introduces the substituent ($R^5$ to $R^9$, $R^{15}$ to $R^{19}$) into the 4-positioned phenyl group of the indenyl ring.

A metallocene compound having a different substituent on the bridging group may be synthesized, using a correspondingly-substituted material. Using a corresponding ketone compound, for example, cyclobutanone, 4-heptenone or the like in place of acetone introduces the substituent ($R^{10}$, $R^{20}$) into the bridging group.

2. Olefin Polymerization Catalyst (1) Components of Olefin Polymerization Catalyst The metallocene compound of the present invention forms an olefin polymerization catalyst component, and the catalyst component may be used in an olefin polymerization catalyst. For example, preferably used here is an olefin polymerization catalyst to be mentioned hereinunder, which contains the metallocene compound as a component (A) therein.

The olefin polymerization catalyst of the present invention contains the following (A) and (B) and optionally contains the following component (C).

Component (A): Metallocene compound represented by the general formula [I].

Component (B): Compound or ion-exchanging layered silicate reacting with the component (A) to form an ion pair.

Component (C): Organoaluminium compound.

(2) Description of Components (2-1) Component (A)

Regarding the metallocene compound represented by the general formula [I] for the component (A), two or more same or different types of the compounds represented by the general formula [I] may be used here.

(2-2) Component (B)

The component (B) is a compound or an ion-exchanging layered silicate that reacts with the component (A) to form an ion pair. The compound that reacts with the component (A) to form an ion pair includes an organoaluminiumoxy compound, a boron compound, a zinc compound, etc. Preferred is an organoaluminiumoxy compound or a boron compound, and more preferred is a boron compound. One or more of these components (B) may be used here either singly or as combined.

(2-2-1) Organoaluminiumoxy Compound

The organoaluminiumoxy compound, one type of the component (B) has an Al—O—Al bond in the molecule, in which the number of the bonds is generally from 1 to 100, preferably from 1 to 50. The organoaluminiumoxy compound of the type is obtained generally by reacting an organoaluminium compound with water or an aromatic carboxylic acid.

The reaction of an organoaluminium with water is carried out generally in an inert hydrocarbon (solvent). The inert hydrocarbon includes an aliphatic hydrocarbon, an alicyclic hydrocarbon and an aromatic hydrocarbon, such as pentane, hexane, heptane, cyclohexane, methylcyclohexane, benzene, toluene, xylene, etc. Preferred is use of an aliphatic hydrocarbon or an aromatic hydrocarbon.

As the organoaluminium compound for use for preparing the organoaluminiumoxy compound, usable is any compound represented by the following general formula [II]. Preferred is use of a trialkylaluminium.

(In the formula [II], $R^a$ represents a hydrocarbon group such as an alkyl group, an alkenyl group, an aryl group, an aralkyl group or the like having from 1 to 18 carbon atoms, preferably from 1 to 12 carbon atoms; $X^a$ represents a hydrogen atom or a halogen atom; t indicates an integer of $1 \leq t \leq 3$.)

The alkyl group in the trialkylaluminum may be any of a methyl group, an ethyl group, a propyl group, an isopropyl group, a butyl group, an isobutyl group, a pentyl group, a hexyl group, an octyl group, a decyl group, a dodecyl group or the like, but is preferably a methyl group or an isobutyl group, more preferably a methyl group.

Two or more of the above-mentioned organoaluminum compounds may be used here as combined.

The reaction ratio of water to the organoaluminum compound (molar ratio of water/Al) is preferably from 0.25/1 to 1.2/1, more preferably from 0.5/1 to 1/1, and the reaction temperature generally falls within a range of from −70 to 100° C., preferably from −20 to 20° C. The reaction time is selected generally from a range of from 5 minutes to 24 hours, preferably from 10 minutes to 5 hours. As water for the reaction, not only simple water but also crystal water contained in copper sulfate hydrate, aluminium sulfate hydrate or the like as well as a component capable of forming water in a reaction system can also be used.

Of the above-mentioned organoaluminiumoxy compounds, those obtained by reacting an alkylaluminium and water are generally referred to aluminoxanes, and in particular, methylaluminoxane (including those substantially comprising methylaluminoxane (MAO)) is preferred as the organoaluminiumoxy compound here.

Needless to say, two or more of the above-mentioned organoaluminiumoxy compounds may be used here as combined, and a solution or dispersion prepared by dissolving or dispersing the organoaluminiumoxy compound in the above-mentioned inert hydrocarbon solvent may also be used here.

As the organoaluminiumoxy compound, exemplified here are those represented by the following general formula [III].

[Chem. 4]

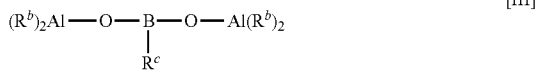

(In the formula [III], $R^b$ represents a hydrocarbon group such as an alkyl group, an alkenyl group, an aryl group, an aralkyl group or the like having from 1 to 18 carbon atoms, preferably from 1 to 12 carbon atoms; $R^c$ represents a hydrocarbon group having from 1 to 10 carbon atoms. Plural $R^b$'s in the formula [III] may be the same as or different from each other.)

The compound represented by the general formula [III] may be obtained by reacting one type of a trialkylaluminum or two or more types of trialkylaluminums and an alkylboronic acid represented by a general formula, $R^cB(OH)_2$ in a ratio (by mol) of from 10/1 to 1/1. In the general formula, $R^c$ represents a hydrocarbon group having from 1 to 10 carbon atoms, preferably from 1 to 6 carbon atoms.

(2-2-2) Boron Compound

The boron compound, one type of the component (B) includes a borane compound, borate compound, etc.

Concrete examples of the borane compound include triphenylborane, tri(o-tolyl)borane, tri(p-tolyl)borane, tri(m-tolyl)borane, tri(o-fluorophenyl)borane, tris(p-fluorophenyl)borane, tris(m-fluorophenyl)borane, tris(2,5-difluorophenyl)borane, tris(3,5-difluorophenyl)borane, tris(4-trifluoromethylphenyl)borane, tris(3,5-ditrifluoromethylphenyl)borane, tris(2,6-ditrifluoromethylphenyl)borane, tris(pentafluorophenyl)borane, tris(perfluoronaphthyl)borane, tris(perfluorobiphenylyl)borane, tris(perfluoroanthryl)borane, tris(perfluorobinaphthyl)borane, etc.

Of those, preferred are tris(3,5-ditrifluoromethylphenyl)borane, tris(2,6-ditrifluoromethylphenyl)borane, tris(pentafluorophenyl)borane, tris(perfluoronaphthyl)borane, tris(perfluorobiphenylyl)borane, tris(perfluoroanthryl)borane and tris(perfluorobinaphthyl)borane; and more preferred are tris(2,6-ditrifluoromethylphenyl)borane, tris(pentafluorophenyl)borane, tris(perfluoronaphthyl)borane and tris(perfluorobiphenylyl)borane.

The borate compound is described concretely. The first example of the compound is a compound represented by the following general formula [IV].

In the formula [IV], $L^1$ represents a neutral Lewis base; H represents a hydrogen atom; $[L^1\text{-}H]$ represents a Broensted acid such as ammonium, anilinium, phosphonium, etc. Examples of include trialkyl-substituted ammoniums such as trimethylammonium, triethylammonium, tripropylammonium, tributylammonium, tri(n-butyl)ammonium, etc.; and dialkylammoniums such as di(n-propyl)ammonium, dicyclohexylammonium, etc.

Examples of anilinium include N,N-dialkylaniliniums such as N,N-dimethylanilinium, N,N-diethylanilinium, N,N-2,4,6-pentamethylanilinium, etc.

Examples of phosphonium include triarylphosphoniums and trialkylphosphoniums such as triphenylphosphonium, tributylphosphonium, tri(methylphenyl)phosphonium, tri(dimethylphenyl)phosphonium, etc.

In the formula [IV], $R^d$ and $R^e$ represent same or different aromatic or substituted aromatic hydrocarbon groups each having from 6 to 20 carbon atoms, preferably from 6 to 16 carbon atoms, and these may be bridged via a bridging group. The substituent in the substituted aromatic hydrocarbon group is preferably an alkyl group typed by a methyl group, an ethyl group, a propyl group, an isopropyl group or the like, or a halogen such as fluorine, chlorine, bromine, iodine, etc.

$X^b$ and $X^c$ each independently represent a hydride group, a halogen atom, a hydrocarbon group having from 1 to 20 carbon atoms, or a substituted hydrocarbon group having from 1 to 20 carbon atoms in which at least one hydrogen atom is substituted with a halogen atom.

Specific examples of the compound represented by the general formula [IV] include tributylammonium tetra(pentafluorophenyl)borate, tributylammonium tetra(2,6-ditrifluoromethylphenyl)borate, tributylammonium tetra(3,5-ditrifluoromethylphenyl)borate, tributylammonium tetra(2,6-difluorophenyl)borate, tributylammonium tetra (perfluoronaphthyl)borate, dimethylanilinium tetra (pentafluorophenyl)borate, dimethylanilinium tetra(2,6-ditrifluoromethylphenyl)borate, dimethylanilinium tetra(3, 5-ditrifluoromethylphenyl)borate, dimethylanilinium tetra(2,6-difluorophenyl)borate, dimethylanilinium tetra(perfluoronaphthyl)borate, triphenylphosphonium tetra(pentafluorophenyl)borate, triphenylphosphonium tetra(2,6-ditrifluoromethylphenyl)borate, triphenylphosphonium tetra(3,5-ditrifluoromethylphenyl)borate, triphenylphosphonium tetra(2,6-difluorophenyl)borate, triphenylphosphonium tetra(perfluoronaphthyl)borate, trimethylammonium tetra(2,6-ditrifluoromethylphenyl)borate, triethylammonium tetra(pentafluorophenyl)borate, triethylammonium tetra(2,6-ditrifluoromethylphenyl)borate, triethylammonium tetra(perfluoronaphthyl)borate, tripropylammonium tetra(pentafluorophenyl)borate, tripropylammonium tetra(2,6-ditrifluoromethylphenyl)borate, tripropylammonium tetra(perfluoronaphthyl)borate, di(1-propyl)ammonium tetra(pentafluorophenyl)borate, dicyclohexylammonium tetraphenylborate, etc.

Of those, preferred are tributylammonium tetra(pentafluorophenyl)borate, tributylammonium tetra(2,6-ditrifluoromethylphenyl)borate, tributylammonium tetra(3,5-ditrifluoromethylphenyl)borate, tributylammonium tetra(perfluoronaphthyl)borate, dimethylanilinium tetra(pentafluorophenyl)borate, dimethylanilinium tetra(2,6-ditrifluoromethylphenyl)borate, dimethylanilinium tetra(3,5-ditrifluoromethylphenyl)borate, and dimethylanilinium tetra(perfluoronaphthyl)borate.

Of those, most preferred are tributylammonium tetra(pentafluorophenyl)borate, tributylammonium tetra(2,6-ditrifluoromethylphenyl)borate, tributylammonium tetra(3,5-ditrifluoromethylphenyl)borate, dimethylanilinium tetra(pentafluorophenyl)borate, dimethylanilinium tetra(2,6-ditrifluoromethylphenyl)borate, and dimethylanilinium tetra(3,5-ditrifluoromethylphenyl)borate.

The second example of the borate compound is represented by the following general formula [V].

$[L^2]^+[BR^dR^eX^bX^c]^-$       [V]

In the formula [V], $L^2$ includes a carbocation, a methyl cation, an ethyl cation, a propyl cation, an isopropyl cation, a butyl cation, an isobutyl cation, a tert-butyl cation, a pentyl cation, a tropinium cation, a benzyl cation, a trityl cation, a sodium cation, a proton, etc. $R^d$, $R^e$, $X^b$ and $X^c$ have the same definitions as in the above-mentioned general formula [IV].

Specific examples of the compound represented by the general formula [V] include trityl tetraphenylborate, trityl tetra(o-tolyl)borate, trityl tetra(p-tolyl)borate, trityl tetra(m-tolyl)borate, trityl tetra(o-fluorophenyl)borate, trityl tetra(p-fluorophenyl)borate, trityl tetra(m-fluorophenyl)borate, trityl tetra(3,5-difluorophenyl)borate, trityl tetra(pentafluorophenyl)borate, trityl tetra(2,6-ditrifluoromethylphenyl)borate, trityl tetra(3,5-ditrifluoromethylphenyl)borate, trityl tetra(perfluoronaphthyl)borate, tropinium tetraphenylborate, tropinium tetra(o-tolyl)borate, tropinium tetra(p-tolyl)borate, tropinium tetra(m-tolyl)borate, tropinium tetra(o-fluorophenyl)borate, tropinium tetra(p-fluorophenyl)borate, tropinium tetra(m-fluorophenyl)borate, tropinium tetra(3,5-difluorophenyl)borate, tropinium tetra(pentafluorophenyl)borate, tropinium tetra(2,6-ditrifluoromethylphenyl)borate, tropinium tetra(3,5-ditrifluoromethylphenyl)borate, tropinium tetra(perfluoronaphthyl)borate, sodium tetraphenylborate, sodium tetra(o-tolyl)borate, sodium tetra(p-tolyl)borate, sodium tetra(m-tolyl)borate, sodium tetra(o-fluorophenyl)borate, sodium tetra(p-fluorophenyl)borate, sodium tetra(m-fluorophenyl)borate, sodium tetra(3,5-difluorophenyl)borate, sodium tetra(pentafluorophenyl)borate, sodium tetra(2,6-ditrifluoromethylphenyl)borate, sodium tetra(3,5-ditrifluoromethylphenyl)borate, sodium tetra(perfluoronaphthyl)borate, hydrogen tetraphenylborate 2 diethyl ether, hydrogen tetra(3,5-difluoromethylphenyl)borate 2 diethyl ether, hydrogen tetra(pentafluorophenyl)borate 2 diethyl ether, hydrogen tetra(2,6-ditrifluoromethylphenyl)borate 2 diethyl ether, hydrogen tetra(3,5-ditrifluoromethylphenyl)borate 2 diethyl ether, hydrogen tetra(perfluoronaphthyl)borate 2 diethyl ether, etc.

Of those, preferred are trityl tetra(pentafluorophenyl)borate, trityl tetra(2,6-ditrifluoromethylphenyl)borate, trityl tetra(3,5-ditrifluoromethylphenyl)borate, trityl tetra(perfluoronaphthyl)borate, tropinium tetra(pentafluorophenyl)borate, tropinium tetra(2,6-ditrifluoromethylphenyl)borate, tropinium tetra(3,5-ditrifluoromethylphenyeborate, tropinium tetra(perfluoronaphthyl)borate, sodium tetra(pentafluorophenyl)borate, sodium tetra(2,6-ditrifluoromethylphenyl)borate, sodium tetra(3,5-ditrifluoromethylphenyl)borate, sodium tetra(perfluoronaphthyl)borate, hydrogen tetra(pentafluorophenyl)borate 2 diethyl ether, hydrogen tetra(2,6-ditrifluoromethylphenyl)borate 2 diethyl ether, hydrogen tetra(3,5-ditrifluoromethylphenyl)borate 2 diethyl ether, and hydrogen tetra(perfluoronaphthyl)borate 2 diethyl ether.

Of those, more preferred are trityl tetra(pentafluorophenyl)borate, trityl tetra(2,6-ditrifluoromethylphenyl)borate, tropinium tetra(pentafluorophenyl)borate, tropinium tetra(2,6-ditrifluoromethylphenyl)borate, sodium tetra(pentafluorophenyl)borate, sodium tetra(2,6-ditrifluoromethylphenyl)borate, hydrogen tetra(pentafluorophenyl)borate 2 diethyl ether, hydrogen tetra(2,6-ditrifluoromethylphenyl)borate 2 diethyl ether, and hydrogen tetra(3,5-ditrifluoromethylphenyl)borate 2 diethyl ether.

As the component (B) in the olefin polymerization catalyst, also usable is a mixture of the above-mentioned organoaluminiumoxy compound and the above-mentioned borane compound or borate compound. Two or more different types of the borane compounds or the borate compounds may be used as combined.

(2-2-3) Ion-Exchanging Layered Silicate

The ion-exchanging layered silicate (hereinafter this may be simply abbreviated as "silicate") is a silicate compound having a crystal structure in which the constituent planes are layered in parallel to each other by the bonding force of an ionic bond or the like and in which the contained ion is exchangeable. Various types of such silicates are known and are concretely described in "Clay Mineralogy" by Haruo Shirozu, Asakura Publishing (1995).

In the present invention, those belonging to the smectite family are preferably used as the component (B), and concretely mentioned are montmorillonite, sauuconite, beidellite, nontronite, saponite, hectorite, stevensite, etc.

Most silicates are, as natural products, mostly produced as the main component of clay minerals, and therefore often contain any other impurities (quartz, cristobalite, etc.) than ion-exchanging layered silicates, and the smectite family silicates for use in the present invention may contain such impurities.

Granulation of Ion-Exchanging Layered Silicate:

For use herein, the silicate may be either in a dry state or in the form of a liquid slurry. The shape of the ion-exchanging layered silicate is not specifically defined. The silicate may be in the form thereof just produced in nature or in the form thereof just artificially synthesized. If desired, the form of the ion-exchanging layered silicate for use herein may be modified through operation of grinding, granulation, classification or the like. Of those, especially preferred are granulated silicates as capable of providing good polymer particulate performance.

The form modification of the ion-exchanging layered silicate through granulation, grinding, classification or the like may be carried out before acid treatment, or the form of the silicate may be modified after acid treatment.

Not specifically defined, the granulation method employable here includes, for example, a stirring granulation method, a spraying granulation method, a rolling granulation method, a briquetting granulation method, a compacting granulation method, an extrusion granulation method, a fluidized-bed granulation method, an emulsion granulation method, a submerged granulation method, a compression molding granulation method, etc. Preferred are a stirring granulation method, a spraying granulation method, a rolling granulation method, and a fluidized-bed granulation method; and more preferred are a stirring granulation method, and a spraying granulation method.

In spraying granulation, water or an organic solvent such as methanol, ethanol, chloroform, methylene chloride, pentane, hexane, heptane, toluene, xylene or the like may be used as the dispersion medium for the starting slurry. Preferably, water is used as the dispersion medium. The concentration of the component (B) in the starting slurry liquid in spraying granulation that gives spherical particles is from 0.1 to 30% by weight, preferably from 0.5 to 20% by weight, more preferably from 1 to 10% by weight. The temperature of the inlet port for the hot air in spraying granulation that gives spherical particles may vary depending on the dispersion medium used. In a case where water is used, the temperature may be from 80 to 260° C., preferably from 100 to 220° C.

In granulation, for obtaining a carrier having a high particle strength and for improving the olefin polymerization activity, the silicate is optionally fine-grained. The silicate may be fine-grained in any method. Regarding the fine-graining method, the silicate may be fine-grained either in dry or in wet condition. Preferred is a wet-grinding method using water as the dispersion medium and utilizing the swellability of the silicate. For example, there are mentioned a forcedly stirring method using Polytron or the like, and a method using a Dyno mill, a pearl mill or the like. The mean particle size before granulation may be from 0.01 to 3 μm, preferably from 0.05 to 1 μm.

If desired, an organic substance, an inorganic solvent, an inorganic salt or various types of binders may be used in granulation. The usable binder includes, for example, magnesium chloride, aluminium sulfate, aluminium chloride, magnesium sulfate, alcohols, glycol, etc.

The spherical particles obtained as above preferably have a compressive fragmentation strength of 0.2 MPa or more for preventing fragmentation or powdering in the polymerization step. The particle size of the granulated ion-exchanging layered silicate may be from 0.1 to 1000 μm, preferably from 1 to 500 μm. The grinding method is not also specifically defined, for which employable is any of dry grinding or wet grinding.

Acid Treatment:

The silicate for use in the present invention is subjected to acid treatment before use, and may be subjected to any combined treatment with any other chemical treatment. The other chemical treatment includes alkali treatment, salt treatment, organic treatment, etc.

The acid treatment of the silicate may change the acid strength of the solid. The acid treatment is effective for ion exchange and for removal of surface impurities, and is additionally effective for eluting a part of cations such as Al, Fe, Mg, Li and the like in the crystal structure.

The acid for use for the acid treatment includes hydrochloric acid, nitric acid, sulfuric acid, phosphoric acid, acetic acid, oxalic acid, benzoic acid, stearic acid, propionic acid, acrylic acid, maleic acid, fumaric acid, phthalic acid, etc. Two or more of these may be used at a time. Above all, preferred are inorganic acids. Preferred are sulfuric acid, hydrochloric acid and nitric acid; and more preferred is sulfuric acid.

A method of combined treatment of acid treatment and salt treatment is preferred, including a method of salt treatment followed by acid treatment, a method of acid treatment followed by salt treatment, a method of simultaneous salt treatment and acid treatment, a method of salt treatment followed by simultaneous salt treatment and acid treatment.

Regarding the acid treatment condition, in general, the acid concentration may be from 0.1 to 30% by weight, the treatment temperature may fall a temperature range of from room temperature to the boiling point of the solvent used, and the treatment time may be from 5 minutes to 24 hours. Preferably, the treatment is carried out under the condition under which at least a part of the compound to be treated could be eluted. In general, the acid is used in the form of an aqueous solution thereof. For example, in a case of using sulfuric acid, the treatment temperature is preferably from 80° C. to 100° C., and the treatment time is preferably from 0.5 hours to less than 5 hours.

The treatment simultaneously combined with salt treatment to form an ionic complex, a molecular complex, an organic derivative or the like may change the surface area and the interlayer distance. For example, by utilizing the ion exchangeability, the interlayer exchanging ion may be substituted with any other bulky ion to give a layered substance where the interlayer distance is enlarged.

Before, during or after the acid treatment, the silicate may be ground or particulated for shape control. In addition, the treatment may be combined with any other chemical treatment such as alkali treatment, organic compound treatment, organic metal treatment, etc.

The salt for use for ion exchange is a compound that contains a cation containing at least one atom selected from a group consisting of Group 1 to Group 14 atoms of the Long Periodic Table (hereinafter simply referred to as "Periodic Table"), and is preferably a compound that comprises a cation containing at least one atom selected from a group consisting of Group 1 to Group 14 atoms of the Periodic Table and an anion derived from at least one atom or atomic group selected from a group consisting of a halogen atom, an inorganic acid and an organic acid, more preferably a compound that comprises a cation containing at least one atom selected from a group consisting of Group 2 to Group 14 atoms of the Periodic Table, and at least one anion selected from a group consisting of Cl, Br, I, F, $PO_4$, $SO_4$, $NO_3$, $CO_3$, $C_2O_4$, $ClO_3$, $OOCCH_3$, $CH_3COCHCOCH_3$, $OCl_2$, $O(NO_3)_2$, $O(ClO_4)_2$, $O(SO_4)$, OH, $O_2Cl_2$, $OCl_3$, OOCH, $OOCCH_2CH_3$, $C_2H_4O_4$ and $C_6H_5O_7$. Two or more of these salts may be used at a time, as combined.

Thus obtained, in the silicate, the pore volume having a radius of 20 angstroms or more, as measured according to a mercury intrusion method, is preferably 0.1 cc/g or more, more preferably from 0.3 to 5 cc/g. The silicate of the type contains adsorbed water and interlayer water when processed in an aqueous solution. Adsorbed water as referred to herein means water adsorbed to the surface or the broken crystal surface of the silicate; and interlayer water means water existing between the layers of the crystal.

Preferably, the silicate is used here after the above-mentioned adsorbed water and interlayer water have been removed. The dewatering method is not specifically defined, for which usable is a method of dewatering with heating, dewatering with heating in vapor circulation, dewatering with heating under reduced pressure, azeotropic dewatering with organic solvent, etc. The heating temperature may fall within a temperature range within which the adsorbed water and the interlayer water could not remain, and is generally 100° C. or higher, preferably 150° C. or higher. However, a high temperature condition to cause structural disorder is not preferred. The heating time may be 0.5 hours or more, preferably 1 hour or more. In the case, the weight loss of the silicate after dewatering drying is preferably 3% by weight or less, as the value in the case of suction at a temperature of 200° C. and under a pressure of 1 mmHg, for 2 hours. In the present invention, when the silicate of which the weight loss is controlled to be 3% by weight or less is used and when the component (A) and the component (C) are kept in contact with each other, it is desirable that the components are treated so that the same weight loss condition could be kept as such.

Composition of Silicate after Acid Treatment:

In the acid-treated silicate that is the component (B) in the present invention, it is desirable that the atomic ratio of Al/Si is from 0.01 to 0.29, more preferably from 0.03 to 0.25, even more preferably from 0.05 to 0.23, from the viewpoint of the activity of the polymerization catalyst and of the molecular weight of the olefin polymer to be produced.

The atomic ratio of Al/Si is the index of the acid treatment intensity in the clay part. Regarding the method of controlling the atomic ratio of Al/Si, the ratio may be controlled by tailoring the type of the acid for the acid treatment, the acid concentration, the acid treatment time and the temperature.

Aluminium and silicon in the silicate may be determined according to a method of preparing a calibration curve through chemical analysis based on JIS and quantifying the atoms through fluorescent X-ray analysis.

(2-3) Component (C)

The component (C) is an optional component, an organoaluminium compound that is optionally used in the present invention.

One example of the organoaluminium compound is represented by the following general formula [VI].

$$AlR_aX_{3-a} \qquad [VI]$$

In the general formula [VI], R represents a hydrocarbon group having from 1 to 20 carbon atoms; X represents a hydrogen atom, a halogen atom, an alkoxy group or a siloxy group; and a indicates a number of from more than 0 to 3.

Specific examples of the organoaluminium compound represented by the general formula [VI] include trialkylaluminiums such as trimethylaluminium, triethylaluminium, tripropylaluminium, triisobutylaluminium, trihexylaluminium, trioctylaluminium, etc.; halogen- or alkoxy-containing alkylaluminiums such as diethylaluminium monochloride, diethylaluminium monomethoxide, etc. Of those, preferred are trialkylaluminiums; and most preferred is trihexylaluminium or trioctylaluminium. Two or more such organoaluminium compounds may be used here as combined.

(3) Catalyst Preparation Method

In the preparation method for the olefin polymerization catalyst in the present invention, the method of bringing the component (A), the component (B) and the component (C) into contact with each other is not specifically defined. For example, the following methods may be exemplified.

(i) The component (A) and the component (B) are brought into contact.

(ii) The component (A) and the component (B) are brought into contact, and then the component (C) is added thereto.

(iii) The component (A) and the component (C) are brought into contact, and the component (B) is added thereto.

(iv) The component (B) and the component (C) are brought into contact, and the component (A) is added thereto.

(v) The components (A), (B) and (C) are brought into contact all at a time.

In addition, the other component may be mixed in one component to be a mixture, or the components may be separately brought into contact with each other in a different order. The contact operation may be carried out not only in catalyst preparation but also in prepolymerization with an olefin or polymerization of an olefin.

Portions of each component, as divided, may be brought into contact with another component, for example, the component (B) and the component (C) are brought into contact and the a mixture of the component (A) and the component (C) is added thereto.

Preferably, the operation of bringing the components (A), (B) and (C) into contact with each other is carried out in an inert gas such as nitrogen or the like and in an inert hydrocarbon solvent such as pentane, hexane, heptane, toluene, xylene or the like. The contact operation may be carried out at a temperature falling within a range of from −20° C. to the boiling point of the solvent, preferably at a temperature falling within a range of from room temperature to the boiling point of the solvent.

(3-1) Catalyst Preparation Method where a Boron Compound or an Organoaluminiumoxy Compound is Used as the Component (B)

In the polymerization catalyst of the invention, the preferred component (B) is a boron compound or an organoaluminiumoxy compound, and is more preferably a boron compound. In a case where the component (B) is an organoaluminiumoxy compound, the molar ration of the component (A) to the component (B) is from 1/0.1 to 1/100,000. In a case where the component (B) is a boron compound, the molar ratio of the component (A) to the component (B) is within a range of from 1/0.1 to 1/100. In a case where the catalyst contains the component (C), the molar ratio of the component (A) to the component (C) is preferably within a range of from 1/0.1 to 1/10,000.

(3-2) Catalyst Preparation Method where a Silicate is Used as the Component (B)

In the polymerization catalyst of the present invention where the component (B) is a silicate, the preferred amount of the component (A), the component (B) and the component (C) to be used is such that that the amount of the metallocene compound of the component (A) is from 0.001 to 10 mmol, more preferably from 0.001 to 1 mmol relative to 1 g of the component (B). The amount of the component (C) to be sued is from 0.1 to 100,000 as the molar ratio of Al/metallocene compound, preferably from 1 to 10,000. The use ratio indicates an ordinary proportion example, and therefore the above-mentioned use ratio range should not define the present invention so far as the catalyst meets the object of the present invention.

(3-3) Catalyst Preparation Method where a Particulate Carrier Except Silicate is Used as the Component (B)

In case where the component (B) is not a silicate, the component (A), the component (B) and/or the component (C) may be carried on a particulate carrier except silicate for use for polymerization. The particulate carrier to be used includes an inorganic carrier, a granular polymer carrier or a mixture thereof. As the inorganic carrier, usable are metals, metal oxides, metal chlorides, metal carbonates, carbonaceous substances or mixtures thereof.

Preferred metals for the inorganic carrier include, for example, iron, aluminium, nickel, etc.

As the metal oxides, there are mentioned simple oxides or composite oxides with an element of Group 1 to Group 14 of the Periodic Table, and for example, there are exemplified various types of natural or synthetic simple oxides or composite oxides such as $SiO_2$, $Al_2O_3$, $MgO$, $CaO$, $B_2O_3$, $TiO_2$, $ZrO_2$, $Fe_2O_3$, $Al_2O_3 \cdot MgO$, $Al_2O_3 \cdot CaO$, $Al_2O_3 \cdot SiO_2$, $Al_2O_3 \cdot MgO \cdot CaO$, $Al_2O_3 \cdot MgO \cdot SiO_2$, $Al_2O_3 \cdot CuO$, $Al_2O_3 \cdot Fe_2O_3$, $Al_2O_3 \cdot NiO$, $SiO_2 \cdot MgO$, etc.

Here, the above-mentioned formulae are not molecular formulae but are mere compositional expressions, and the structure and the component ratio of the composite oxide for use in the present invention are not specifically defined.

The metal oxides for use in the present invention may absorb a small amount of water with no problem, and may also contain minor impurities with no problem.

As the metal chlorides, for example, preferred are chlorides of alkali metals or alkaline earth metals, and concretely, $MgCl_2$, $CaCl_2$ and the like are especially preferred.

As the metal carbonates, preferred are carbonates of alkali metals or alkaline earth metals, and concretely, there are mentioned magnesium carbonate, calcium carbonate, barium carbonate, etc.

As the carbonaceous materials, for example, there are mentioned carbon black, activated carbon, etc.

Any of the above-mentioned inorganic carriers may be favorably used in the present invention, but especially preferred is use of metal oxides, silica, alumina, etc.

It is desirable that the inorganic carrier is, before use, fired in air or in an inert gas such as nitrogen, argon or the like, generally at 200 to 800° C., preferably at 400 to 600° C. to thereby control the amount of the surface hydroxyl group to be from 0.8 to 1.5 mmol/g.

The properties of the inorganic carrier are not specifically defined. Preferred is use of inorganic carries having a mean particle size of generally from 5 to 200 µm, preferably from 10 to 150 µm, a mean pore size of from 20 to 1000 angstroms, preferably from 50 to 500 angstroms, a specific surface area of from 150 to 1000 $m^2/g$, preferably from 200 to 700 $m^2/g$, a pore volume of from 0.3 to 2.5 $cm^3/g$, preferably from 0.5 to 2.0 $cm^3/g$, and an apparent specific gravity of from 0.20 to 0.50 $g/cm^3$, preferably from 0.25 to 0.45 $g/cm^3$.

Needless to say, the above-mentioned inorganic carrier may be used directly as it is, but as a pretreatment before use thereof, the carrier may be brought into contact with an organoaluminium compound such as trimethylaluminium, triethylaluminium, triisobutylaluminium, trihexylaluminium, tripropylaluminium, tributylaluminium, trioctylaluminium, tridecylaluminium, diisobutylaluminium hydride or the like, or with an organoaluminiumoxy compound containing an Al—O—Al bond.

The method for bringing the components into contact with each other in producing an olefin polymerization catalyst that comprises the component (A), a compound reacting with the component (A) to form an ion pair (component B) and a particulate carrier, is not specifically defined, for which, for example, employable is any of the following methods.

(I) The component (A) and the component (B) are brought into contact with each other, and then with a particulate carrier.

(II) The component (A) and a particulate carrier are brought into contact with each other, and then with the component (B).

(III) The component (B) and a particulate carrier are brought into contact with each other, and then with the component (A).

Of those contacting methods, preferred are (I) and (III), and most preferred is (I). For all those contacting methods, employable is a method of bringing the components into contact with each other generally in an inert atmosphere such as nitrogen, argon or the like and generally in the presence of a liquid inert hydrocarbon, for example, an aromatic hydrocarbon (generally having from 6 to 12 carbon atoms) such as benzene, toluene, xylene, ethylbenzene or the like, or an aliphatic or alicyclic hydrocarbon (generally having from 5 to 12 carbon atoms) such as heptane, hexane, decane, dodecane, cyclohexane or the like, with stirring or not with stirring.

The contact operation may be carried out generally at a temperature of from −100° C. to 200° C., preferably from −50° C. to 100° C., more preferably from 0° C. to 50° C., and for from 5 minutes to 50 hours, preferably from 30 minutes to 24 hours, more preferably from 30 minutes to 12 hours.

In the step of bringing the component (A), the component (B) and a particulate carrier into contact with each other, usable are both an aromatic hydrocarbon solvent in which some components are soluble or hardly soluble, and an aliphatic or alicyclic hydrocarbon solvent in which some components are insoluble or hardly soluble, as described above.

In a case where the contact reaction of the components is stepwise carried out, the solvent used in the previous step is not removed but may be directly used as the solvent in the contact reaction of the latter stage. After the former-stage contact reaction using a soluble solvent, a liquid inert hydrocarbon solvent in which some components are insoluble or hardly soluble (for example, aliphatic hydrocarbon, alicyclic hydrocarbon or aromatic hydrocarbon such as pentane, hexane, decane, dodecane, cyclohexane, benzene, toluene, xylene, etc.) may be added to collect the desired product as a solid matter, and then after a part or all of the soluble solvent is removed by drying or the like to take out the desired product as the solid matter, the latter-stage contact reaction with the desired product may be carried out using any of the above-mentioned inert hydrocarbon solvents. The present invention does not exclude any mode of carrying out the components-contacting reaction plural times.

In the present invention, the usage ratio of the component (A), the component (B) and the particulate carrier is not specifically defined, but preferably falls in the range mentioned below.

In a case where an organoaluminiumoxy compound is used as the component (B), the atomic ratio of aluminium in the organoaluminiumoxy compound to the transition metal (M) in the component (A) (Al/M) is generally from 1 to 100,000, preferably from 5 to 1000, more preferably from 50 to 400. In a case where a borane compound or a borate compound is used, the atomic ratio of boron to the transition metal (M) in the component (A) (B/M) is generally from 0.01 to 100, preferably from 0.1 to 50, more preferably from 0.2 to 10.

In a case where a mixture of an organoaluminiumoxy compound, a borane compound and a borate compound is sued as the ion pair-forming compound (component (B)), it is desirable that the usage ratio of the constituent components in the mixture to the transition metal (M) is selected in the manner as above.

The amount of the particulate carrier to be used is 1 g relative to from 0.0001 to 5 mmol, preferably from 0.001 to 0.5 mmol, more preferably from 0.01 to 0.1 mmol of the transition metal in the component (A).

The component (A), the component (B) and a particulate carrier are brought into contact with each other according to any of the above-mentioned contacting methods (I) to (III), and then the solvent is removed or the system is washed and formed into a slurry with an inert solvent to give an olefin polymerization catalyst as a solid catalyst. It is desirable that the solvent removal is carried out under normal pressure or under reduced pressure, at 0 to 200° C., preferably at 20 to 150° C. for 1 minute to 50 hours, preferably for 10 minutes to 10 hours.

The olefin polymerization catalyst may also be obtained according to the methods mentioned below.

(IV) The component (A) and a particulate carrier are brought into contact and the solvent is removed to give a solid catalyst component, and this is brought into contact with an organoaluminiumoxy compound, a borane compound, a borate compound or a mixture thereof under polymerization condition.

(V) An organoaluminiumoxy compound, a borane compound, a borate compound or a mixture thereof is brought into contact with a particulate carrier and the solvent is removed to give a solid catalyst component, and this is brought into contact with the component (A) under polymerization condition.

Also in these contacting methods (IV) and (V), the same conditions as mentioned above may apply to the component ratio, the contact condition and the solvent removal condition.

Before use of the catalyst that contains the component (A), the component (B) and optionally the component (C) as the catalyst for olefin polymerization (intended polymerization), if desired, the catalyst may be subjected to prepolymerization treatment of preliminary polymerizing a small amount of an olefin such as ethylene, propylene, 1-butene, 1-hexene, 1-octene, 4-methyl-1-pentene, 3-methyl-1-butene, vinylcycloalkane, styrene or the like. For the prepolymerization, any known method is employable.

3. Olefin Polymerization Method

In the present invention, employable is any and every polymerization mode that realizes efficient contact between the polymerization catalyst containing a metallocene compound represented by the above-mentioned general formula [I] and monomer for olefin polymerization or copolymerization.

Concretely, employable here are a slurry method and a solution method using an inert solvent, a bulk polymerization method and a high-pressure ion polymerization method substantially not using an inert solvent but using the olefin monomer as a solvent, or a vapor-phase polymerization method substantially not using a liquid solvent but keeping the monomer in a gaseous state. Preferred are solution polymerization and high-pressure ion polymerization.

The polymerization mode employable here may be continuous polymerization or batch polymerization, or preliminary polymerization may be added thereto. The combination of the polymerization modes is not specifically defined. Employable here is any of two-stage solution polymerization, two-stage bulk polymerization, bulk polymerization followed by vapor-phase polymerization, or two-stage vapor-phase polymerization. Any more polymerization stages are also employable for polymer production.

A component for water removal, that is, a so-called scavenger may be added to the polymerization system with no problem.

As the scavenger of the type, usable are an organoaluminium compounds such as trimethylaluminium, triethylaluminium, triisobutylaluminium, trihexylaluminium, trioctylaluminium, etc.; the above-mentioned organoaluminiumoxy compounds; modified organoaluminium compounds prepared by modifying the above-mentioned organoaluminium compounds with alcohols or phenols; Organozinc compounds such as diethylzinc, dibutylzinc, etc.; organomagnesium compounds such as diethylmagnesium, dibutylmagnesium, ethylbutylmagnesium, etc.; Grignard compounds such as ethylmagnesium chloride, butylmagnesium chloride, etc. Of those, preferred are triethylaluminium, triisobutylaluminium, trihexylaluminium, and trioctylaluminium; and more preferred are triisobutylaluminium, trihexylaluminium and trioctylaluminium.

The molecular weight of the polymer to be produced may be controlled by varying the polymerization conditions such as the polymerization temperature, the olefin monomer concentration, the molar ratio of the catalyst, etc. Adding hydrogen, the above-mentioned scavenger or the like as a chain transfer agent to the polymerization system effectively realizes molecular weight control of the polymer.

A multi-stage polymerization system comprising two or more stages that differ from each other in the polymerization conditions such as the hydrogen concentration, the monomer amount, the polymerization pressure, the polymerization temperature or the like is also applicable to the present invention with no problem.

(1) Polymerization Monomer

In the present invention, olefin indicates an unsaturated hydrocarbon, and "α-olefin" indicates those of such olefins where the double bond is at the α-position (between the end carbon and the next carbon). Concretely, the olefin monomer includes ethylene, propylene, 1-butene, 1-pentene, 1-hexene, 1-heptene, 1-octene, 1-decene, 1-dodecene, 1-hexadecene, 4-methyl-1-pentene, styrene, vinylcyclohexane, diene, triene, cyclic olefin, etc.

(2) Ethylene Homopolymerization Method and Copolymerization Method

In the present invention, more preferred polymerization using the above-mentioned olefin polymerization catalyst is ethylene homopolymerization or ethylene/α-olefin copolymerization. The preferred polymerization method is a solution polymerization method using an inert solvent, or a polymerization method not substantially using an inert solvent but using the olefin monomer as a solvent, for example, a high-pressure ion polymerization method.

The polymerization temperature is generally from 0 to 300° C. In a vapor-phase polymerization method, a bulk polymerization method or a slurry polymerization method, the preferred polymerization temperature is from 40 to 120° C., more preferably from 50 to 100° C., and the preferred polymerization pressure is from 0.1 to 10 MPa, more preferably from 1 to 5 MPa.

The preferred polymerization temperature in solution polymerization is from 0 to 170° C., more preferably from 50 to 170° C., even more preferably from 120 to 170° C., and the preferred polymerization pressure is from 0.1 to 10 MPa, more preferably from 1 to 5 MPa.

The preferred polymerization temperature in high-pressure ion polymerization is from 140 to 300° C., more preferably from 160 to 260° C., and the preferred polymerization pressure is from 40 to 150 MPa, more preferably from 50 to 100 MPa.

As obvious from Examples, the performance difference between the olefin polymerization catalyst of the present invention and already-existing catalysts is greater at a higher polymerization temperature especially in point of the molecular weight of the polymer to be produced. In particular, at a polymerization temperature of 120° C. or higher, the effect is remarkable, as obvious from Examples.

α-olefins that are comonomers include those having from 3 to 20 carbon atoms, preferably from 3 to 8 carbon atoms. Concretely, there are exemplified propylene, 1-butene, 1-hexene, 1-octene, 4-methyl-1-pentene, etc.

Two or more such α-olefins may be copolymerized with ethylene, as combined.

The copolymerization may be any of alternate copolymerization, random copolymerization or block copolymerization with no problem. In a case where ethylene is copolymerized with any other α-olefin, the amount of the other α-olefin may be selected within a range of at most 90 mol % of all monomers, but is preferably at most 50 mol %. Needless to say, it is possible to use a small amount of any other comonomer than ethylene and α-olefin, and in this case, the additional comonomer includes aromatic vinyl compounds such as styrene, 4-methylstyrene, 4-dimethylaminostyrene, etc.; dienes such as 1,4-butadiene, 1,5-hexadiene, 1,4-hexadiene, 1,7-octadiene, 4-vinyl-1-cyclohexene, 5-vinylnorbornene, 5-ethylidene-2-norbornene, norbornadiene, etc.; cyclic compounds such as norbornene, cyclopentene, etc.

4. Use of Olefin Polymer

The olefin copolymer produced through polymerization using the metallocene compound of the present invention has excellent mechanical properties, and are widely used covering from industrial-use materials and life materials, for example, as films, sheets, fibers, nonwoven fabrics, various containers, molded articles, modifiers, etc.

Further, the low-density olefin copolymer to be obtained according to the production method of the present invention has many branches and therefore has excellent radical-crosslinking characteristics, and is expected to be alternatives to crosslinked olefinic rubber (EPDM). In other words, using the EPDM application method of 1) crosslinking the rubber with an organic peroxide or sulfur serving as a crosslinking agent, and 2) combining the rubber with any other thermoplastic resin to give a dynamically-crosslinking thermoplastic elastomer, directly as it is, the present invention realizes production of a material having a crosslinked structure. The materials obtained according to these methods have long-lasting durability and are excellent in weather resistance and heat resistance, and therefore can be used for automobile parts, electric wires, cables, etc.

EXAMPLES

In the following, the present invention is described in more detail with reference to Examples and Comparative Examples to thereby verify the excellence of the present invention and the superiority in the constitution of the present invention, but the present invention is not restricted by these Examples.

Methods for determining the physical properties of the polymers obtained in Examples and Comparative Examples are as described below.

(1) Melt Flow Rate (MFR)

According to Table 1—Condition D in Appendix A in JIS K7210 (2004 edition), the found data at a test temperature of 190° C. and under a nominal load of 2.16 kg is expressed as MFR.

(2) Number-Average Molecular Weight (Mn) and Molecular Weight Distribution (Mw/Mn)

The formed ethylenic polymer was subjected to gel permeation chromatography (GPC) under the condition mentioned below, and the number-average molecular weight (Mn) and the weight-average molecular weight (Mw) were determined, and the molecular weight distribution (Mw/Mn) was thus calculated.

[Measurement Condition for Gel Permeation Chromatography]:
Apparatus: Waters' Alliance GPC2000 Model
Column: Shodex-HT806M
Solvent: 1,2-dichlorobenzene
Flow Rate: 1 ml/min
Temperature: 145° C.
Universal assessment was made using monodispersed polystyrene fractions.

Under the condition mentioned above, the sample was chromatographed to record the data at sampling intervals of 1 second. Based on the chromatogram data and according to the method described in "Size Exclusion Chromatography" by Sadao Mori (Kyoritsu Publishing), Chap. 4, pp. 51-60 (1991), the differential molecular weight distribution curve and the mean molecular weight (Mn, Mw) were calculated. However, for correcting the molecular weight dependence of dn/dc, the height H from the base line in the chromatogram was corrected according to the following equation.

$$H'=[1.032+189.2/M(PE)]\times H$$

For the molecular weight conversion from polystyrene to polyethylene, the following equation was used.

$$M(PE)=0.468\times M(PS)$$

(3) Density

According to Method A (collecting gas over water) of the test method described in JIS K7112 (2004 edition), the density was measured.

(4) Comonomer Content

The monomer composition of ethylene/1-hexene copolymer was analyzed through NMR according to the description in a publication (Anal. Chem., 2004, 5734-5747).

[NMR Measurement Condition]

As the solvent, used was a mixture solvent of 1,2-dichlorobenzene/heavy bromobenzene (4/1). The sample concentration was 150 mg/2.4 mL. The sample was introduced into an NMR sample tube, then fully purged with nitrogen, and dissolved in a heat block at 130° C. to give a uniform solution. Using Bruker Avance III Cryo-NMR with a 10 mmϕ cryoprobe, the sample was analyzed at 130° C.

The measurement condition was as follows. $^1$H-NMR: solvent presaturation method, 18° pulse, number of integration frequencies 256, $^{13}$C-NMR: proton complete decoupling condition, 90° pulse, number of integration frequencies 512.

(5) Melting Point ($T_m$)

Using Seiko Electronics' EXSTAR6000, DSC differential scanning calorimeter, the sample (about 5 mg) was melted at 180° C. for 5 minutes, then cooled to −20° C. at a rate of 10° C./min, kept at −20° C. for 5 minutes, and thereafter heated up to 180° C. at a rate of 10° C./min to provide a melting curve of the sample. The peak top temperature of the main endothermic peak in the final heating stage to provide the melting curve was referred to as the melting point $T_m$ of the sample.

The molecular weight of the polymer obtained herein can be evaluated according to the above-mentioned measurements (1) and (2). In other words, the polymer of which the value of MFR determined in the measurement (1) is smaller, and the polymer of which the number-average molecular weight determined in the measurement (2) is larger can be said to be polymers having a higher molecular weight.

In addition, the comonomer content in the copolymer obtained herein, concretely, the content of 1-hexene that is α-olefin in the copolymer obtained in Examples and Comparative Examples can be evaluated according to the above-mentioned measurements (3) and (4). The polymer of which the value of the density determined in the measurement (3) is smaller, and the polymer of which the hexene content determined in (4) is larger can be said to be polymers having a higher comonomer content. In other words, it may be said that the polymer obtained using a different catalyst and at the same temperature and in the same monomer ratio and having a smaller density or having a higher hexene content is excellent in copolymerizability (excellent in the performance of efficiently taking in the comonomer).

<1> Synthesis of Metallocene Compound

Synthesis of Metallocene Compound A: isopropylidenebis(4-phenyl-1-indenyl)dimethylhafnium

[Chem. 5]

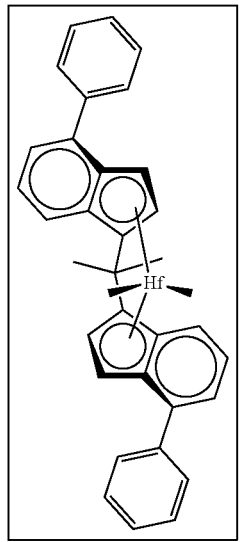

(Metallocene Compound A)

(1) Synthesis of 4-phenyl-indene

This was synthesized according to the method described in JP-A 2008-101034.

(2) Synthesis of 2,2-bis(4-phenyl-inden-1-yl)propane 1.00 g (5.21 mmol) of 4-phenyl-1-indene, 10 mL of 1,2-dimethoxyethane (DME) and 0.583 g (10.4 mmol) of potassium hydroxide were put in a 100-mL glass reactor, and heated under reflux at 90° C. for 1 hour. The reaction liquid was cooled to 0° C., then 0.151 g (2.60 mmol) of acetone was added thereto and heated under reflux at 90° C. for 6 hours. The reaction liquid was cooled to room temperature, then 20 mL of distilled water was added thereto, transferred into a reparatory funnel, extracted three times with ethyl acetate, and dried with sodium sulfate. Sodium sulfate was filtered away, the solvent was evaporated away under reduced pressure, and the resultant crude product was purified through silica gel column chromatography (developing solvent, dichloromethane/petroleum ether=1/20) to give 0.45 g (yield 41%) of 2,2-bis(4-phenyl-inden-1-yl)propane as a pale yellow solid.

$^1$H-NMR (400 MHz, CDCl$_3$): δ7.52 (dd, 4H), 7.44 (t, 4H), 7.41-7.34 (m, 4H), 7.16 (t, 2H), 7.11 (dd, 2H), 6.59 (t, 2H), 3.48 (d, 2H), 1.81 (s, 6H).

(3) Synthesis of isopropylidenebis(4-phenyl-1-indenium)hafnium dichloride 1.50 g (3.5 mmol) of 2,2-bis(4-phenyl-inden-1-yl)propane was put in a 200-mL three-neck flask having a rotor set therein and equipped with a three-way cock and a thermometer, and 70 ml of toluene and 15 ml of diethyl ether were added thereto to dissolve the compound. This was cooled to −70° C. in a dry ice-isopropyl alcohol bath, and 4.7 ml (7.5 mmol) of n-butyllithium/hexane (1.59 M solution) was added thereto and stirred for 40 minutes. The cooling bath was removed, and the mixture was heated up to 20° C., kept as such for 1 hour, and then the solvent was evaporated away. 70 mL of toluene and 3 mL of diethyl ether were added thereto to dissolve the mixture, and cooled to −70° C. 1.25 g (3.9 mmol) of hafnium tetrachloride was added, and immediately the cooling bath was removed, and the mixture was gradually restored to room temperature. From $^1$H-NMR thereof, the stereoisomeric composition of the resultant complex was racemic form/meso form=33/67. The solvent was evaporated away, 60 ml of DME was added to the residue and heated with stirring at 60° C. for 3 hours. Through the operation, the stereoisomeric composition of the complex became racemic form/meso form=93/7. The supernatant was removed through decantation, then the precipitate was dissolved in dichloromethane, and the insoluble matter was removed through filtration. The filtrate was concentrated, the resultant solid was washed with a small amount of toluene, and then dried under reduced pressure to give isopropylidenebis(4-phenyl-1-indenium) hafnium dichloride as a yellow powdery solid. The racemic form purity of the product was 100%, and the yield thereof was 1.25 g, and 53%.

$^1$H-NMR (400 MHz, CDCl$_3$): δ7.78 (d, J=8.8 Hz, 2H), 7.57 (dd, J=8.3 Hz, 4H), 7.42 (t, J=7.1 Hz, 4H), 7.34 (t, J=7.3 Hz, 2H), 7.26 (d, J=6.3 Hz, 2H), 7.13-7.09 (m, 2H), 6.72 (dd, J=3.6 Hz, 2H), 6.18 (d, J=3.6 Hz, 2H), 2.41 (s, 6H).

(4) Synthesis of isopropylidenebis(4-phenyl-1-indenyedimethylhafnium 0.51 g (0.76 mmol) of isopropylidenebis(4-phenyl-1-indenium)hafnium dichloride and 40 ml of toluene were put in a 100-mL side-arm flask having a rotor set therein, and dissolved. This was cooled to 0° C. in an ice bath, 1.8 mL (5.4 mmol) of methylmagnesium bromide/diethyl ether (3.0 M solution) was added, and then heated with stirring at 40° C. for 11 hours. At room temperature, 0.47 ml (3.7 mmol) of trimethylsilyl chloride was added, stirred for 30 minutes, and 10 ml of dioxane was added and stirred for 30 minutes. The insoluble matter was removed through filtration, and the filtrate was concentrated to give a yellow solid. This was washed with a small amount of hexane, then the supernatant was removed through decantation, and the residue was dried under reduced pressure to give a pale yellow powdery solid of isopropylidenebis(4-phenyl-1-indenyl)dimethylhafnium. The racemic form purity of the compound was 100%, the yield thereof was 0.32 g and 66%.

$^1$H-NMR (400 MHz, C$_6$D$_6$): δ7.69 (dd, J=8.4 Hz, 4H), 7.35 (d, J=9.0 Hz, 2H), 7.22 (t, J=7.6 Hz, 4H), 7.15-7.09 (m, 4H), 6.84-6.80 (m, 4H), 5.57 (d, J=3.5 Hz, 2H), 1.77 (s, 6H), −0.99 (s, 6H).

Synthesis of Metallocene Compound B: di-n-propylmethylenebis(4-phenyl-1-indenyl)dimethylhafnium

[Chem. 6]

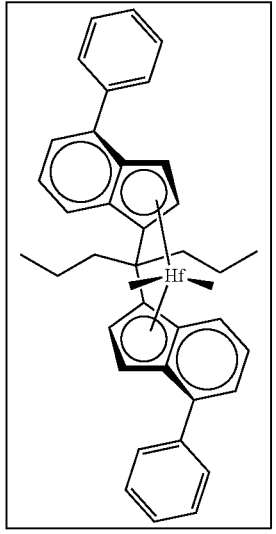

(Metallocene Compound B)

(1) Synthesis of 4,4-bis(4-phenyl-inden-1-yl)heptane 25.0 g (130 mmol) of 4-phenyl-1-indene, 200 mL of DME, and 14.6 g (260 mmol) of potassium hydroxide were put in a 100-mL glass reactor, and heated under reflux at 90° C. for 1 hour. The reaction liquid was cooled to 0° C., then 7.42 g (65.1 mmol) of 4-heptanone was added thereto and heated under reflux at 90° C. for 15 hours. The reaction liquid was cooled to room temperature, then 150 mL of distilled water was added thereto, transferred into a separatory funnel, extracted three times with ethyl acetate, and dried with sodium sulfate. Sodium sulfate was filtered away, the solvent was evaporated away under reduced pressure, and the resultant crude product was purified through silica gel column chromatography (developing solvent, petroleum ether) to give 7.0 g (yield 24%) of 4,4-bis(4-phenyl-inden-1-yl)heptane as a pale yellow solid.

$^1$H-NMR (400 MHz, CDCl$_3$): δ7.54 (dd, 4H), 7.45 (t, 4H), 7.40-7.30 (m, 4H), 7.12-7.05 (m, 4H), 6.63 (s, 2H), 3.51 (d, 4H), 2.25-2.17 (m, 4H), 1.22-1.08 (m, 4H), 0.89 (t, 6H).

(2) Synthesis of di-n-propylmethylenebis(4-phenyl-1-indenyl)hafnium dichloride 3.00 g (6.2 mmol) of 4,4-bis(4-phenyl-inden-1-yl)heptane was put in a 200-mL three-neck flask having a rotor set therein and equipped with a three-way cock and a thermometer, and 60 ml of toluene and 50 ml of diethyl ether were added thereto to dissolve the compound. This was cooled to −70° C. in a dry ice-isopropyl alcohol bath, and 9.2 ml (14.9 mmol) of n-butyllithium/hexane (1.63 M solution) was added thereto and stirred for 60 minutes. The cooling bath was removed, and the mixture was restored to room temperature, and the solvent was evaporated away. 100 mL of toluene and 5 mL of diethyl ether were added thereto to dissolve the mixture, and cooled to −70° C. 2.29 g (7.2 mmol) of hafnium tetrachloride was added, and immediately the cooling bath was removed, and the mixture was gradually restored to room temperature. From $^1$H-NMR thereof, the stereoisomeric composition of the resultant complex was racemic form/meso form=38/62. The solvent was evaporated away, 110 ml of DME was added to the residue and heated with stirring at 50° C. for 7 hours. The solvent was evaporated away, 130 ml of toluene was added to the residue to dissolve it, and the insoluble matter was removed through filtration. The filtrate was concentrated, the resultant solid was washed with a small amount of hexane, and then dried under reduced pressure to give di-n-propylmethylenebis(4-phenyl-1-indenyl)hafnium dichloride as a yellow powdery solid. The racemic form purity of the product was 100%, and the yield thereof was 0.57 g, and 13%.

$^1$H-NMR (400 MHz, CDCl$_3$): δ7.62 (d, J=8.8 Hz, 2H), 7.57 (dd, J=8.4 Hz, 4H), 7.42 (t, J=7.2 Hz, 4H), 7.34 (t, J=7.2 Hz, 2H), 7.25 (d, 2H), 7.14-7.10 (m, 2H), 6.72 (dd, J=3.6 Hz, 2H), 6.23 (d, J=3.6 Hz, 2H), 2.96-2.85 (m, 2H), 82.67-1.97 (m, 2H), 1.91-1.75 (m, 4H), 1.23 (t, J=7.2 Hz, 6H).

(3) Synthesis of di-n-propylmethylenebis(4-phenyl-1-indenyl)dimethylhafnium 0.57 g (0.78 mmol) of di-n-propylmethylenebis(4-phenyl-1-indenyl)hafnium dichloride and 30 ml of toluene were put in a 100-mL side-arm flask having a rotor set therein, and dissolved. 2.7 mL (8.1 mmol) of methylmagnesium bromide/diethyl ether (3.0 M solution) was added, and then heated with stirring at 50° C. for 5 hours. At room temperature, 0.79 ml (6.3 mmol) of trimethylsilyl chloride was added, stirred for 30 minutes, and 5 ml of dioxane was added and stirred for 30 minutes. The insoluble matter was removed through filtration, and the filtrate was concentrated to give a yellow solid. This was washed with a small amount of hexane, then the supernatant was removed through decantation, and the residue was dried under reduced pressure to give a pale yellow powdery solid of di-n-propylmethylenebis(4-phenyl-1-indenyl)dimethylhafnium. The racemic form purity of the compound was 100%, the yield thereof was 0.28 g and 53%.

$^1$H-NMR (400 MHz, C$_6$D$_6$): δ7.69 (dd, J=8.4 Hz, 4H), 7.35 (d, J=8.8 Hz, 2H), 7.23 (t, J=7.2 Hz, 4H), 7.15-7.09 (m, 4H), 6.88-6.83 (m, 4H), 5.73 (d, J=3.6 Hz, 2H), 2.55-2.44 (m, 2H), 2.25-2.15 (m, 2H), 1.66-1.50 (m, 4H), 81.03 (t, J=7.2 Hz, 6H), −0.97 (s, 6H).

Synthesis of Metallocene Compound C: cyclobutylidenebis(4-phenyl-1-indenyl)dimethylhafnium

[Chem. 7]

(Metallocene Compound C)

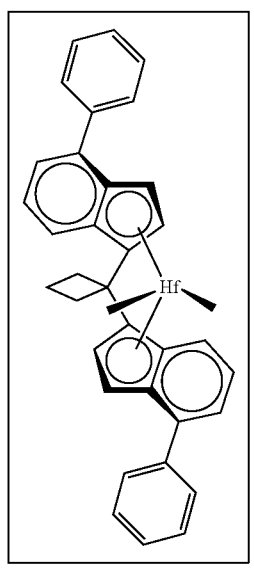

(1) Synthesis of 1,1-bis(4-phenyl-inden-1-yl)cyclobutane 22.4 g (116 mmol) of 4-phenylindene, 150 mL of DME, and 13.0 g (233 mmol) of potassium hydroxide were put in a 500-mL glass reactor, and heated under reflux at 90° C. for 1 hour. The reaction liquid was cooled to 0° C., then 4.00 g (57.2 mmol) of cyclobutanone was added thereto and heated under reflux at 90° C. for 10 hours. The reaction liquid was cooled to room temperature, then 200 mL of distilled water was added thereto, transferred into a separatory funnel, extracted three times with ethyl acetate, and dried with sodium sulfate. Sodium sulfate was filtered away, the solvent was evaporated away under reduced pressure, and the resultant crude product was purified through silica gel column chromatography (developing solvent, petroleum ether) to give 10.0 g (yield 40%) of 1,1-bis(4-phenyl-inden-1-yl)cyclobutane as a pale yellow solid.

$^1$H-NMR (400 MHz, CDCl$_3$): δ7.51 (dd, 4H), 7.46-7.39 (m, 6H), 7.36-7.22 (m, 2H), 7.24 (t, 2H), 7.14 (dd, 2H), 6.07 (t, 2H), 3.49 (d, 4H), 2.78 (t, 4H), 2.11 (quint, 2H).

(2) Synthesis of racemic cyclobutylidenebis(4-phenyl-1-indenyl)hafnium dichloride 4.37 g (10.0 mmol) of 1,1-bis(4-phenyl-inden-1-yl)cyclobutane and 100 ml of diethyl ether were put in a 300-mL glass reactor, and cooled to −70° C. in a dry ice-heptane bath. 12.8 ml (20.4 mmol) of n-butyllithium/n-hexane solution (1.59 mol/L) was dropwise added thereto and stirred at room temperature for 4 hours. The solvent was evaporated away under reduced pressure from the reaction liquid, then 100 ml of toluene was added, and cooled to −70° C. in a dry ice-heptane bath. 3.20 g (10.0 mmol) of hafnium chloride was added thereto. Subsequently, while gradually restored to room temperature, this was stirred for 17 hours. In this stage, the ratio of the racemic form to the meso form of the resultant compound was 48/52.

The solvent was evaporated away under reduced pressure from the reaction liquid, 26 mL of DME was added thereto, and stirred at 60° C. for 5 hours. The reaction liquid was cooled to room temperature, then filtered through glass fit, and the solid was washed twice with 3 mL of DME. The resultant crude product was extracted with 150 mL of dichloromethane, filtered through Celite, and the solvent was evaporated away under reduced pressure to give 4.84 g (yield 71%) of a racemic form of racemic 1,1-cyclobutylidenebis(4-phenylindenyl)hafnium dichloride as an orange solid.

$^1$H-NMR (400 MHz, CDCl$_3$): δ=7.57 (d, 4H), 7.52 (d, 2H), 7.42 (t, 4H), 7.35 (t, 2H), 7.27 (d, 2H), 7.09 (dd, 2H), 6.66 (d, 2H), 6.07 (d, 2H), 3.60 (quartet, 2H), 3.17 (quartet, 2H), 2.49 (quintet, 2H).

(3) Synthesis of racemic cyclobutylidenebis(4-phenyl-1-indenyl)dimethylhafnium 1.50 g (2.19 mmol) of 1,1-cyclobutylidenebis(4-phenyl-indenyl)hafnium dichloride and 60 ml of toluene were put in a 100-mL glass reactor. 6.55 mL (19.7 mmol) of methylmagnesium bromide/diethyl ether solution (3.0 mol/L) was dropwise added thereto at room temperature, and stirred at 80° C. for 5 hours. The reaction liquid was cooled to 0° C. in an ice bath, then 2.4 mL (19.0 mmol) of chlorotrimethylsilane was added thereto, stirred at room temperature for 30 minutes, and subsequently 5.0 mL (58.4 mmol) of 1,4-dioxane was added, and further stirred at room temperature for 30 minutes. The suspension was filtered through Celite, the solvent was evaporated away under reduced pressure, and the resultant yellow solid was suspended in 5 mL of hexane, filtered through glass frit, and the solid was further washed twice with 5 mL of hexane to give 1.37 g (97%) of a racemic form of racemic cyclobutylidenebis(4-phenyl-1-indenyl)dimethylhafnium as a yellow solid.

$^1$H-NMR (400 MHz, C$_6$D$_6$): δ7.70 (dd, 4H), 7.23 (t, 4H), 7.18-7.08 (m, 6H), 6.80 (dd, 2H), 6.78 (d, 2H), 5.52 (d, 2H), 3.05 (quartet, 2H), 2.60 (quartet, 2H), 2.07 (quintet, 2H), −1.02 (s, 6H).

Synthesis of Metallocene Compound D: cyclopentylidenebis(4-phenyl-1-indenyl)dimethylhafnium

[Chem. 8]

(Metallocene Compound D)

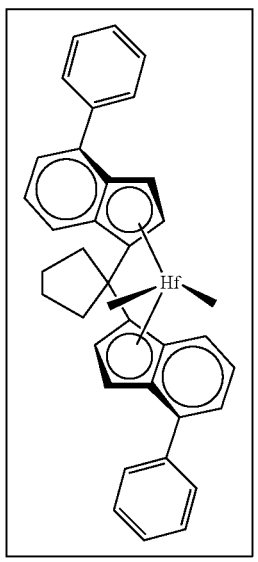

(1) Synthesis of 1,1-bis(4-phenylinden-1-yl)cyclopentane 25.0 g (130 mmol) of 4-phenyl-indene, 200 mL of DME, and 14.6 g (260 mmol) of potassium hydroxide were put in a 100-mL glass reactor, and heated under reflux at 90° C. for 1 hour. The reaction liquid was cooled to 0° C., then 4.94 g (58.6 mmol) of cyclopentanone was added thereto and heated under reflux at 90° C. for 6 hours. The reaction liquid was cooled to room temperature, then 150 mL of distilled water was added thereto, transferred into a separatory funnel, extracted three times with dichloromethane, and dried with sodium sulfate. Sodium sulfate was filtered away, the solvent was evaporated away under reduced pressure, and the resultant crude product was purified through silica gel column chromatography (developing solvent, petroleum ether) to give 9.0 g (yield 31%) of 1,1-bis(4-phenylinden-1-yl)cyclopentane as a pale yellow solid.

$^1$H-NMR (400 MHz, CDCl$_3$): δ7.52 (m, 6H), 7.44 (t, 4H), 7.36 (t, 2H), 7.21 (t, 2H), 7.12 (d, 2H), 6.60 (s, 2H), 3.47 (d, 4H), 2.43 (t, 4H), 1.84 (quint, 4H).

(2) Synthesis of cyclopentylidenebis(4-phenyl-1-indenyl)hafnium dichloride 2.50 g (5.6 mmol) of 1,1-bis(4-phenylinden-1-yl)cyclopentane, 20 mL of toluene and 20 mL of diethyl ether were put in a 100-mL three-neck flask having a rotor set therein and equipped with a three-way cock and a thermometer, and dissolved. This was cooled to −70° C. in a dry ice-isopropyl alcohol bath, and 7.2 ml (11.8 mmol) of n-butyllithium/hexane (1.64 M solution) was added thereto and stirred for 90 minutes. The cooling bath was removed, and the mixture was restored to room temperature, and the solvent was evaporated away under reduced pressure. 30 mL of toluene and 1.5 mL of diethyl ether were added thereto to dissolve the mixture, and cooled to −70° C. 1.79 g (5.6 mmol) of hafnium tetrachloride was added, and immediately the cooling bath was removed, and the mixture was gradually restored to room temperature. From $^1$H-NMR thereof, the stereoisomeric composition of the resultant complex was racemic form/meso form=33/67. The solvent was evaporated away, 30 ml of DME was added to the residue and heated with stirring at 60° C. for 11 hours. The supernatant was collected through decantation. 40 mL of DME was added to the resultant residue, heated at 60° C. for 3 hours, the supernatant was collected through decantation and combined with the previously-collected liquid, and the solvent was evaporated away. 45 mL of toluene was added and heated at 40° C., and the insoluble matter was removed through hot filtration. The filtrate was concentrated to be 20 mL, then 5 mL of hexane was added and cooled to −20° C., and the precipitated yellow powdery solid was collected. The solid was washed with a small amount of hexane, and dried under reduced pressure to give a yellow powdery solid of 1,1-cyclopentylidenebis(4-phenyl-1-indenyl)hafnium dichloride. The racemic purity of the compound was 100%, and the yield thereof was 0.55 g and 14%.

$^1$H-NMR (400 MHz, CDCl$_3$): δ7.70 (d, J=8.8 Hz, 4H), 7.57 (dd, J=8.3 Hz, 4H), 7.41 (t, J=7.0 Hz, 4H), 7.34 (t, J=7.3 Hz, 4H), 7.26 (dd, J=6.8 Hz, 4H), 7.12-7.08 (m, 2H), 6.69 (dd, J=3.6 Hz, 2H), 6.15 (d, J=3.5 Hz, 2H), 3.16-3.09 (m, 2H), 2.95-2.88 (m, 2H), 2.19-1.99 (m, 4H).

(3) Synthesis of cyclopentylidenebis(4-phenyl-1-indenyl)dimethylhafnium 0.50 g (0.72 mmol) of cyclopentylidenebis(4-phenyl-1-indenyl)hafnium dichloride and 30 ml of toluene were put in a 100-mL side-arm flask having a rotor set therein, and dissolved. 2.4 mL (7.2 mmol) of methylmagnesium bromide/diethyl ether (3.0 M solution) was added, and then heated with stirring at 50° C. for 7 hours. At room temperature, 0.70 ml (5.5 mmol) of trimethylsilyl chloride was added, stirred for 30 minutes, and 5 ml of dioxane was added and stirred for 30 minutes. The insoluble matter was removed through filtration, and the filtrate was concentrated to give a yellow solid. This was washed with a small amount of hexane, then the supernatant was removed through decantation, and the residue was dried under reduced pressure to give a pale yellow powdery solid of 1,1-cyclopentylidenebis (4-phenyl-1-indenyl)dimethylhafnium. The racemic form purity of the compound was 100%, the yield thereof was 0.32 g and 68%.

$^1$H-NMR (400 MHz, C$_6$D$_6$): δ7.69 (d, J=8.0 Hz, 4H), 7.28 (d, J=9.2 Hz, 2H), 7.22 (t, J=7.2 Hz, 4H), 7.13-7.08 (m, 4H), 6.83-6.78 (m, 4H), 5.57 (d, J=3.6 Hz, 2H), 2.60-2.51 (m, 2H), 2.34-2.26 (m, 2H), 1.80-1.62 (m, 4H), −0.99 (s, 6H).

Synthesis of Metallocene Compound E: cyclohexylidenebis(4-phenyl-1-indenyl)dimethylhafnium

[Chem. 9]

(Metallocene Compound E)

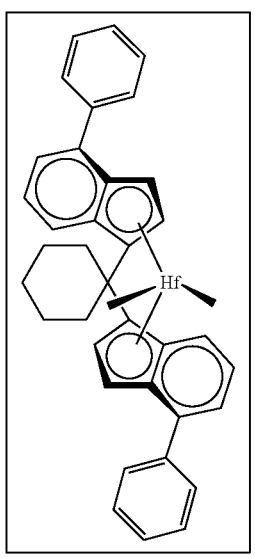

(1) Synthesis of 1,1-bis(4-phenylindenyl-1-yl)cyclohexane 25.0 g (130 mmol) of 4-phenylindene, 200 mL of DME, and 14.6 g (260 mmol) of potassium hydroxide were put in a 100-mL glass reactor, and heated under reflux at 90° C. for 1 hour. The reaction liquid was cooled to 0° C., then 6.38 g (65.1 mmol) of cyclohexanone was added thereto and heated under reflux at 90° C. for 6 hours. The reaction liquid was cooled to room temperature, then 150 mL of distilled water was added thereto, transferred into a separatory funnel, extracted three times with dichloromethane, and dried with sodium sulfate. Sodium sulfate was filtered away, the solvent was evaporated away under reduced pressure, and the resultant crude product was purified through silica gel column chromatography (developing solvent, petroleum ether) to give 9.0 g (yield 30%) of 1,1-bis(4-phenylinden-1-yl)cyclohexane as a pale yellow solid.

$^1$H-NMR (400 MHz, CDCl$_3$): δ7.51 (m, 6H), 7.44 (t, 4H), 7.36 (t, 2H), 7.16 (t, 2H), 7.09 (d, 2H), 6.73 (s, 2H), 3.49 (d, 4H), 2.45 (m, 4H), 1.71 (brs, 4H), 1.58 (m, 4H).

(2) Synthesis of cyclohexylidenebis(4-phenyl-1-indenyl)hafnium dichloride 3.00 g (6.5 mmol) of 1,1-bis(4-phenylinden-1-yl)cyclohexane was put in a 200-mL three-neck flask having a rotor set therein and equipped with a three-way cock and a thermometer, and 40 mL of toluene and 30 mL of diethyl ether were added thereto to dissolve the compound. This was cooled to −70° C. in a dry ice-isopropyl alcohol bath, and 8.4 ml (13.8 mmol) of n-butyllithium/hexane (1.64 M solution) was added thereto and stirred for 60 minutes. The cooling bath was removed, and the mixture was restored to room temperature, and the solvent was evaporated away under reduced pressure. 50 mL of toluene and 3 mL of diethyl ether were added thereto to dissolve the mixture, and cooled to −70° C. 2.09 g (6.5 mmol) of hafnium tetrachloride was added, and immediately the cooling bath was removed, and the mixture was gradually restored to room temperature. From $^1$H-NMR thereof, the stereoisomeric composition of the resultant complex was racemic form/meso form=24/76. The solvent was evaporated away, 150 ml of DME was added to the residue and heated with stirring at 60° C. for 13 hours. The supernatant was collected through decantation. 100 mL of DME was added to the resultant residue, heated at 60° C. for 5 hours, the supernatant was collected through decantation and combined with the previously-collected liquid, and the solvent was evaporated away. 80 mL of toluene was added, and the insoluble matter was removed through filtration. The filtrate was concentrated and cooled to −20° C., and the precipitated yellow powdery solid was collected. The solid was washed with a small amount of hexane, and dried under reduced pressure to give cyclohexylidenebis(4-phenyl-1-indenyl)hafnium dichloride. The racemic purity of the compound was 100%, and the yield thereof was 0.46 g and 10%.

$^1$H-NMR (400 MHz, CDCl$_3$): δ7.72 (d, J=8.8 Hz, 2H), 7.58 (dd, J=8.4 Hz, 4H), 7.42 (t, J=7.2 Hz, 4H), 7.35 (t, J=7.2 Hz, 2H), 7.26 (d, J=6.4 Hz, 2H), 7.13-7.09 (m, 2H), 6.74 (dd, J=3.6 Hz, 2H), 6.20 (d, J=3.6 Hz, 2H), 3.02-2.87 (m, 4H), 2.03-1.94 (m, 4H), 1.82-1.74 (m, 2H).

(3) Synthesis of cyclohexylidenebis(4-phenyl-1-indenyl)dimethylhafnium 0.46 g (0.64 mmol) of cyclohexylbis(4-phenylindenyl)hafnium dichloride and 30 ml of toluene were put in a 100-mL side-arm flask having a rotor set therein, and dissolved. 2.2 mL (6.6 mmol) of methylmagnesium bromide/diethyl ether (3.0 M solution) was added, and then heated with stirring at 50° C. for 4 hours. At room temperature, 0.64 ml (5.1 mmol) of trimethylsilyl chloride was added, stirred for 30 minutes, and 5 ml of dioxane was added and stirred for 30 minutes. The insoluble matter was removed through filtration, and the filtrate was concentrated to give a yellow solid. This was washed with a small amount of hexane, then the supernatant was removed through decantation, and the residue was dried under reduced pressure to give a pale yellow powdery solid of cyclopentylidenebis(4-phenyl-1-indenyedimethylhafnium. The racemic form purity of the compound was 100%, the yield thereof was 0.25 g and 59%.

$^1$H-NMR (400 MHz, C$_6$D$_6$): δ7.70 (dd, J=8.3 Hz, 4H), 7.30 (d, J=8.8 Hz, 2H), 7.23 (t, J=7.6 Hz, 4H), 7.14-7.09 (m, 4H), 6.86-6.82 (m, 4H), 5.57 (d, J=3.6 Hz, 2H), 2.42-2.27 (m, 4H), 1.69-1.62 (m, 4H), 1.51-1.43 (m, 2H), −0.99 (s, 6H).

Synthesis of Metallocene Compound F: isopropylidenebis[4-(4-isopropylphenyl)-1-inden yl]dimethylhafnium

[Chem. 10]

(Metallocene Compound F)

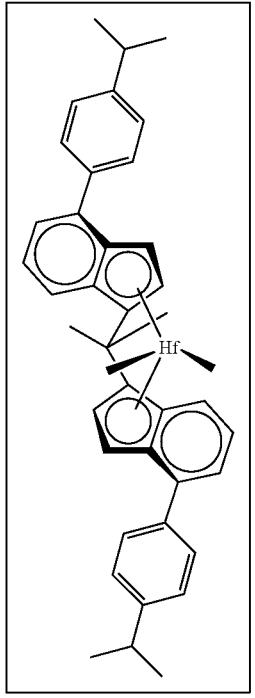

(1) Synthesis of 4-(4-isopropylphenyl)indene 38 g (180 mmol) of tripotassium phosphate, 100 mL of distilled water, 100 mL of DME, 11 g (67.1 mmol) of 4-isopropylphenylboronic acid, 11.0 g (56.4 mmol) of 7-bromo-1H-indene, 323 mg (0.460 mmol) of dichlorobis(triphenylphosphine)palladium, and 432 mg (1.65 mmol) of triphenyl phosphine were put into a 500-mL glass reactor in that order, and then heated under reflux at 90° C. for 8 hours. This was left cooled to room temperature, then the reaction liquid was poured into 100 mL of distilled water, transferred into a separatory funnel, and extracted three times with hexane. At room temperature 5 mL of concentrated hydrochloric acid was added to the hexane solution, then stirred at room temperature for 30 minutes, the palladium compound was precipitated, filtered out through filter paper, and the filtrate was washed three times each with saturated saline water and distilled water, and dried with sodium sulfate. Sodium sulfate was filtered away, the solvent was evaporated away under reduced pressure, and the residue was purified through silica gel column chromatography (developing solvent, hexane/diisopropyl ether=20/1) to give 13.2 g (yield 100%) of 4-(4-isopropylphenyl)indene as a pale red oil.

(2) Synthesis of 2,2-bis(4-(4-isopropylphenyl)-inden-1-yl)propane 13.18 g (56.2 mmol) of 4-(4-isopropylphenyl)indene, 85 mL of DME, and 4.26 g (75.9 mmol) of potassium hydroxide were put in a 200-mL glass reactor, and heated under reflux at 90° C. for 2 hours. The reaction liquid was cooled to 0° C., then 2.1 mL (28.6 mmol) of acetone was added thereto and heated under reflux at 90° C. for 6 hours. The reaction liquid was cooled to room temperature, then 100 mL of distilled water was added thereto, cooled to 0° C. in an ice bath, 6 mL of concentrated hydrochloric acid was added thereto, and stirred at room temperature for 15 minutes. The reaction liquid was transferred into a separatory funnel, extracted three times with diisopropyl ether, and the resultant diisopropyl ether solution as washed three times each with saturated saline water and distilled water, and dried with sodium sulfate. Sodium sulfate was filtered away, the solvent was evaporated away under reduced pressure, and the resultant solid was washed with 30 mL of hexane, and dried in vacuum to give 10.3 g (yield 72%) of 2,2-bis (4-(4-isopropylphenyl)-inden-1-yl)propane as a pale yellow solid.

$^1$H-NMR (400 MHz, CDCl$_3$): δ 7.45 (d, 4H), 7.36 (d, 2H), 7.30 (d, 4H), 7.13 (t, 2H), 7.10 (d, 2H), 6.57 (t, 2H), 3.49 (d, 2H), 2.97 (sept, 2H), 1.79 (s, 6H), 1.31 (d, 2H).

(3) Synthesis of racemic-isopropylidenebis[4-(4-isopropylphenyl)-1-indenyl]hafnium dichloride 3.56 g (7.00 mmol) of 2,2-bis(4-(4-isopropylphenyl)-inden-1-yl)propane and 70 ml of diethyl ether were put in a 200-mL glass reactor, and cooled to −70° C. in a dry ice-heptane bath. 8.7 mL (14.4 mmol) of n-butyl lithium/n-hexane solution (1.65 mol/L) was dropwise added thereto, and stirred at room temperature for 4 hours. The solvent was evaporated away under reduced pressure from the reaction liquid, 80 mL of toluene was added, and cooled to −70° C. in a dry ice/heptane bath. 2.24 g (6.99 mmol) of hafnium tetrachloride was added thereto. Subsequently, while gradually restored to room temperature, this was stirred for 17 hours. The ratio of the racemic form to the meso form formed in this stage was 2/8.

The solvent was evaporated away under reduced pressure from the reaction liquid, 60 mL of DME was added, and stirred at 60° C. for 4 hours. The reaction liquid was cooled to room temperature, then filtered through glass frit, and the solid was collected through filtration to give 4.32 g of a racemic form of isopropylidenebis[4-(4-isopropylphenyl)-1-indenyl]hafnium dichloride containing lithium chloride, as a yellow solid.

$^1$H-NMR (400 MHz, CDCl$_3$): δ=7.76 (d, 2H), 7.52 (d, 4H), 7.28 (d, 4H), 7.25 (d, 2H), 7.09 (dd, 2H), 6.75 (d, 2H), 6.16 (d, 2H), 2.92 (sep, 2H), 2.40 (s, 6H), 1.26 (d, 12H).

(4) Synthesis of racemic-isopropylidenebis[4-(4-isopropylphenyl)-1-indenyl]dimethylhafnium 1.00 g of the above-mentioned, lithium chloride-containing isopropylidenebis[4-(4-isopropylphenyl)-1-indenyl]hafnium dichloride (the content is 1.32 mmol or less) and 50 mL of toluene were put in a 100-mL glass reactor. 3.1 mL (9.3 mmol) of methylmagnesium bromide/diethyl ether solution (3.0 mol/L) was dropwise added thereto at room temperature, and stirred at 80° C. for 4 hours. The reaction liquid was cooled to 0° C. in an ice bath, then 0.84 mL (6.65 mmol) of chlorotrimethylsilane was added thereto, stirred at room temperature for 20 minutes, and subsequently 1.70 mL (19.9 mmol) of 1,4-dioxane was added, and further stirred at room temperature for 30 minutes. The suspension was filtered through Celite, the solvent was evaporated away under reduced pressure, and the resultant yellow solid was suspended in 10 mL of hexane, filtered through glass frit, and the solid was further washed three times with 5 mL of hexane to give 702 mg of a racemic form of isopropylidenebis[4-(4-isopropylphenyl)-1-indenyl]dimethylhafnium as a yellow solid. The yield based on the ligand was 61% (presumed that all the dichloro form was used).

$^1$H-NMR (400 MHz, $C_6D_6$): δ=7.74 (d, 4H), 7.37 (d, 2H), 7.21 (d, 2H), 7.17 (d, 4H), 6.90 (d, 2H), 6.86 (dd, 2H), 5.59 (d, 2H), 2.71 (sep, 2H), 1.80 (s, 6H), 1.13 (d, 12H), −0.90 (s, 6H).

Synthesis of Metallocene Compound G: isopropylidenebis[4-(3,5-dimethylphenyl)-1-indenyl]dimethylhafnium

[Chem. 11]

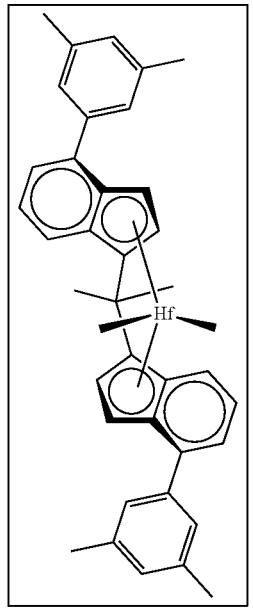

(Metallocene Compound G)

(1) Synthesis of 4-(3,5-dimethylphenyl)indene

This was synthesized according to the method described in JP-A 2008-101034.

(2) Synthesis of 2,2-bis(4-(3,5-dimethylphenyl)-inden-1-yl)propane 24.4 g (111 mmol) of 4-(3,5-dimethylphenyl)indene, 200 mL of DME and 12.4 g (222 mmol) of potassium hydroxide were put in a 500-mL glass reactor, and heated under reflux at 90° C. for 1 hour. The reaction liquid was cooled to 0° C., then 3.22 g (55.5 mmol) of acetone was added thereto and heated under reflux at 90° C. for 6 hours. The reaction liquid was cooled to room temperature, then 200 mL of distilled water was added thereto, and the resultant suspension was filtered through filter paper, and the solid on the filter paper was washed twice with 50 mL of petroleum ether. The resultant crude product was purified through silica gel column chromatography (developing solvent, dichloromethane/petroleum ether=1/20) to give 10.0 g (yield 37%) of 2,2-bis(4-(3,5-dimethylphenyl)-inden-1-yl)propane as a gray solid.

$^1$H-NMR (400 MHz, $CDCl_3$): δ7.35 (dd, 2H), 7.14 (t, 2H), 7.14 (s, 4H), 7.09 (d, 2H), 7.01 (s, 2H), 6.57 (s, 2H), 3.48 (d, 4H), 2.39 (s, 12H), 1.80 (s, 6H).

(3) Synthesis of racemic-isopropylidenebis[4-(3,5-dimethylphenyl)-1-indenyl]hafnium dichloride 2.40 g (5.00 mmol) of 2,2-bis(4-(3,5-dimethylphenyl)-inden-1-yl)propane and 50 mL of diethyl ether were put in a 200-mL glass reactor, and cooled to −70° C. in a dry ice-heptane bath. 6.2 mL (10.2 mmol) of n-butyllithium-n-hexane solution (1.64 mol/L) was dropwise added thereto, and stirred at room temperature for 4 hours. The solvent was evaporated away from the reaction liquid under reduced pressure, 50 mL of toluene was added thereto, and cooled to −70° C. in a dry ice-heptane bath. 1.60 g (5.00 mmol) of hafnium tetrachloride was added thereto. Subsequently, while gradually restored to room temperature, this was stirred for 18 hours. The ratio of the racemic form to the meso form formed in this stage was 47/53.

The solvent was evaporated away under reduced pressure from the reaction liquid, 20 mL of DME was added, and stirred at 60° C. for 5 hours. The reaction liquid was cooled to room temperature, then filtered through glass frit, and the solid was washed twice with 5 mL of DME to give 3.07 g of a racemic form of isopropylidenebis[4-(3,5-dimethylphenyl)-1-indenyl]hafnium dichloride, as a yellow solid.

$^1$H-NMR (400 MHz, $CDCl_3$): δ=7.74 (d, 2H), 7.24 (d, 2H), 7.21 (s, 4H), 7.07 (dd, 2H), 6.98 (s, 2H), 6.74 (d, 2H), 6.17 (d, 2H), 2.39 (s, 6H), 2.32 (s, 12H).

(4) Synthesis of racemic-isopropylidenebis[4-(3,5-dimethylphenyl)-1-indenyl]dimethylhafnium 1.00 g of the above-mentioned, lithium chloride-containing isopropylidenebis[4-(3,5-dimethylphenyl)-1-indenyl]hafnium dichloride (the content is 1.37 mmol or less) and 50 mL of toluene were put in a 100-mL glass reactor. 3.2 mL (9.6 mmol) of methylmagnesium bromide/diethyl ether solution (3.0 mol/L) was dropwise added thereto at room temperature, and stirred at 80° C. for 2 hours. The reaction liquid was cooled to 0° C. in an ice bath, then 0.87 mL (6.9 mmol) of chlorotrimethylsilane was added thereto, stirred at room temperature for 10 minutes, and subsequently 1.75 mL (20.5 mmol) of 1,4-dioxane was added, and further stirred at room temperature for 1.5 hours. The suspension was filtered through Celite, the solvent was evaporated away under reduced pressure, and the resultant yellow solid was suspended in 10 mL of hexane, filtered through glass frit, and the solid was further washed twice with 3 mL of hexane to give 593 mg of a racemic form of isopropylidenebis[4-(3,5-dimethylphenyl)-1-indenyl]dimethylhafnium as a yellow solid. The yield based on the ligand was 53% (presumed that all the dichloro form was used).

$^1$H-NMR (400 MHz, $C_6D_6$): δ=7.44 (s, 4H), 7.39 (d, 2H), 7.23 (d, 2H), 6.92 (d, 2H), 6.88 (dd, 2H), 6.81 (s, 2H), 5.65 (d, 2H), 2.15 (s, 12H), 2.32 (s, 6H), −0.88 (s, 6H).

Synthesis of Metallocene Compound H: isopropylidenebis[4-(3,5-di-t-butylphenyl)-1-indenyl]dimethylhafnium

[Chem. 12]

(Metallocene Compound H)

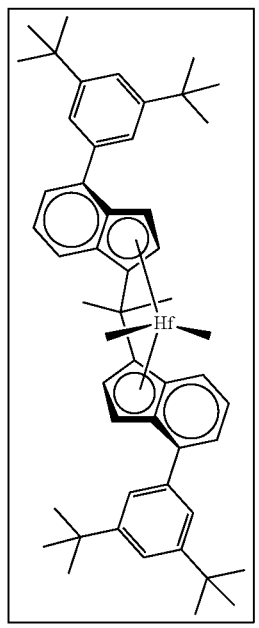

(1) Synthesis of 2,2-bis(4-bromo-inden-1-yl)propane 20.0 g (103 mmol) of 4-bromophenylindene, 200 mL of DME and 12.0 g (206 mmol) of potassium hydroxide were put in a 500-mL glass reactor, and heated under reflux at 90° C. for 1 hour. The reaction liquid was cooled to 0° C., then 3.00 g (52.0 mmol) of acetone was added thereto and heated under reflux at 90° C. for 4 hours. The reaction liquid was cooled to room temperature, and the solvent was evaporated away under reduced pressure. The resultant crude product was purified through silica gel column chromatography (developing solvent, petroleum ether) to give 12.0 g (yield 54%) of 2,2-bis(4-bromo-inden-1-yl)propane as a yellow solid.

$^1$H-NMR (400 MHz, CDCl$_3$); δ7.20 (d, 2H), 7.19 (d, 2H), 6.92 (t, 2H), 6.58 (s, 2H), 3.39 (s, 4H), 1.72 (s, 6H).

(2) Synthesis of 3,5-di-t-butylphenylboronic acid

1-Bromo-3,5-di-t-butylbenzene and 40 mL of tetrahydrofuran were put in a 100-mL glass reactor, and cooled to −70° C. in a dry ice-heptane bath. 16.4 mL (40.9 mmol) of n-butyllithium-n-hexane solution (2.5 mol/L) was dropwise added thereto, and stirred for 30 minutes. Subsequently at −78° C., 4.25 g (40.9 mmol) of trimethyl borate was added and stirred for 2 hours, and further stirred at room temperature for 12 hours. An aqueous 1 M hydrogen chloride solution was added to the reaction liquid until the pH of the liquid could reach 3, then transferred into a separatory funnel, extracted three times with t-butyl methyl ether, and dried with sodium sulfate. Sodium sulfate was filtered away, the solvent was evaporated under reduced pressure, and the resultant crude product was purified through silica gel column chromatography (developing solvent, petroleum ether/ethyl acetate=20/1) to give 8.00 g (yield 91%) of 3,5-di-t-butylphenylboronic acid as a pale yellow solid.

$^1$H-NMR (400 MHz, CDCl$_3$): δ7.72 (d, 1H), 7.57 (s, 2H), 4.61 (s, 2H), 1.32 (s, 18H).

(3) Synthesis of dimethylbis(4-(3,5-di-t-butylphenyl)-inden-1-yl)methane 21.6 g (102 mmol) of tripotassium phosphate, 150 mL of distilled water, 150 mL of DME, 14.3 g (61.3 mmol) of 3,5-di-t-butylphenylboronic acid, 11.0 g (25.5 mmol) of 2,2-bis(4-bromoinden-1-yl)propane, 358 mg (0.510 mmol) of dichlorobis(triphenylphosphine)palladium, and 267 mg (1.02 mmol) of triphenyl phosphine were put into a 500-mL glass reactor in that order, and then heated under reflux at 90° C. for 48 hours. This was left cooled to room temperature, then the reaction liquid was poured into 50 mL of distilled water, transferred into a separatory funnel, and extracted three times with ethyl acetate, and dried with sodium sulfate. Sodium sulfate was filtered away, the solvent was evaporated away under reduced pressure, and the resultant crude product was purified through silica gel column chromatography (developing solvent, petroleum ether) to give 10.0 g (yield 60%) of dimethylbis(4-(3,5-di-t-butylphenyl)-inden-1-yl)methane as a yellow solid.

$^1$H-NMR (400 MHz, CDCl$_3$): δ7.43 (m, 4H), 7.38 (d, 4H), 7.22-7.12 (m, 4H), 6.59 (s, 2H), 3.50 (d, 4H), 1.82 (s, 6H), 1.39 (s, 36H).

(4) Synthesis of racemic-isopropylidenebis[4-(3,5-di-t-butylphenyl)-1-indenyl]hafnium dichloride 3.25 g (5.00 mmol) of dimethylbis(4-(3,5-di-t-butylphenyl)-inden-1-yl)methane and 50 ml of diethyl ether were put in a 200-mL glass reactor, and cooled to −70° C. in a dry ice-heptane bath. 6.2 mL (10.2 mmol) of n-butyllithium-n-hexane solution (1.64 mol/L) was dropwise added thereto, and stirred at room temperature for 4 hours. The solvent was evaporated away from the reaction liquid under reduced pressure, 60 mL of toluene was added thereto, and cooled to −70° C. in a dry ice-heptane bath. 1.60 g (5.00 mmol) of hafnium tetrachloride was added thereto. Subsequently, while gradually restored to room temperature, this was stirred for 16 hours. The ratio of the racemic form to the meso form formed in this stage was 17/83.

The solvent was evaporated away under reduced pressure from the reaction liquid, 10 mL of DME was added, and stirred at 60° C. for 5 hours. The reaction liquid was cooled to room temperature, then filtered through glass frit, and the solid was washed twice with 3 mL of DME to give 3.35 g of a racemic form of isopropylidenebis[4-(3,5-di-t-butylphenyl)-1-indenyl]hafnium dichloride, as a yellow solid.

$^1$H-NMR (400 MHz, CDCl$_3$): δ=7.79 (d, 2H), 7.50 (d, 4H), 7.41 (s, 2H), 7.32 (d, 2H), 7.13 (dd, 2H), 6.80 (d, 2H), 6.19 (d, 2H), 2.42 (s, 6H), 1.31 (s, 36H).

(5) Synthesis of racemic-isopropylidenebis[4-(3,5-di-t-butylphenyl)-1-indenyl]dimethylhafnium 1.00 g of the above-mentioned, lithium chloride-containing isopropylidenebis[4-(3,5-dimethylphenyl)-1-indenyl] hafnium dichloride (the content is 1.16 mmol or less) and 50 mL of toluene were put in a 100-mL glass reactor. 3.7 mL (11.1 mmol) of methylmagnesium bromide/diethyl ether solution (3.0 mol/L) was dropwise added thereto at room temperature, and stirred at 90° C. for 2.5 hours. The reaction liquid was cooled to 0° C. in an ice bath, then 1.15 mL (9.10 mmol) of chlorotrimethylsilane was added thereto, stirred at room temperature for 15 minutes, and subsequently 2.3 mL (26.9 mmol) of 1,4-dioxane was added, and further stirred at room temperature for 40 minutes. The suspension was filtered through Celite, and the solvent was evaporated away under reduced pressure. The resultant yellow solid was suspended in 5 mL of hexane, filtered through glass frit, and the solid was further washed three times with 3 mL of hexane to give 611 mg of a racemic form of isopropylidenebis[4-(3,5-di-t-butylphenyl)-1-indenyl]dimethylhafnium as a yellow solid. The yield based on the ligand was 48% (presumed that all the dichloro form was used).

$^1$H-NMR (400 MHz, C$_6$D$_6$): δ=7.79 (d, 4H), 7.60 (s, 2H), 7.41 (d, 2H), 7.33 (d, 2H), 6.94 (d, 2H), 6.90 (dd, 2H), 5.57 (d, 2H), 1.80 (s, 6H), 1.35 (s, 36H), −0.86 (s, 6H).

Synthesis of Metallocene Compound I: isopropylidenebis[4-(3-t-butylphenyl)-1-indenyl]dimethylhafnium

[Chem. 13]

(Metallocene Compound I)

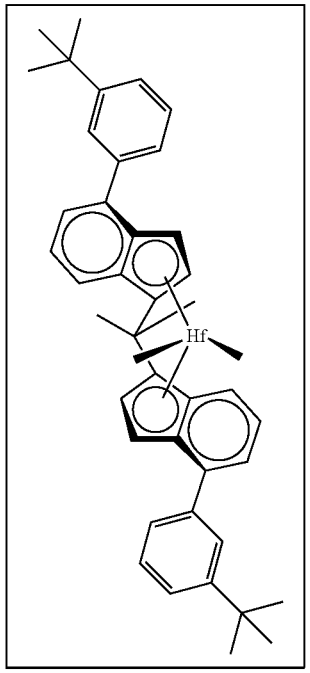

(1) Synthesis of 4-(3-t-butylphenyl)indene 40.4 g (205 mmol) of tripotassium phosphate, 200 mL of distilled water, 200 mL of DME, 21.9 g (123 mmol) of 3-t-butylphenylboronic acid, 20.0 g (102 mmol) of 7-bromo-1H-indene, 720 mg (1.02 mmol) of dichlorobis(triphenylphosphine)palladium, and 537 mg (2.05 mmol) of triphenyl phosphine were put into a 500-mL glass reactor in that order, and then heated under reflux at 90° C. for 15 hours. This was left cooled to room temperature, transferred into a separatory funnel, and extracted three times with ethyl acetate. The ethyl acetate solution was washed three times with saturated saline water, and dried with sodium sulfate. Sodium sulfate was filtered away, the solvent was evaporated away under reduced pressure, and the residue was purified through silica gel column chromatography (developing solvent, petroleum ether) to give 22.7 g (yield 89%) of 4-(3-t-butylphenyl) indene as a yellow oil.

(2) Synthesis of 2,2-bis(4-(3-t-butylphenyl)-inden-1-yl)propane 10.0 g (40.3 mmol) of 4-(3-t-butylphenyl)indene, 100 mL of DME and 3.00 g (52.3 mmol) of potassium hydroxide were put in a 200-mL glass reactor, and heated under reflux at 90° C. for 1 hour. The reaction liquid was cooled to 0° C., 1.20 mL (20.0 mmol) of acetone was added, and then heated under reflux at 90° C. for 12 hours. The reaction liquid was cooled to room temperature, 200 mL of distilled water was added, transferred into a separatory funnel, extracted three times with ethyl acetate, and dried with sodium sulfate. Sodium sulfate was filtered away, the solvent was evaporated away under reduced pressure, and the residue was purified through silica gel column chromatography (developing solvent, petroleum ether/dichloromethane=20/1) to give 5.00 g (yield 46%) of 2,2-bis(4-(3-t-butylphenyl)-inden-1-yl)propane as a yellow solid.

$^1$H-NMR (400 MHz, CDCl$_3$): δ7.55 (s, 2H), 7.42-7.37 (m, 6H), 7.36-7.31 (m, 2H), 7.18 (d, 2H), 7.13 (t, 2H), 6.58 (t, 2H), 3.48 (d, 2H), 1.81 (s, 6H), 1.38 (s, 18H).

(3) Synthesis of isopropylidenebis(4-(3-t-butylphenyl)-1-indenyl)hafnium dichloride 3.01 g (5.6 mmol) of 2,2-bis(4-(3-t-butylphenyl)-inden-1-yl)propane was put in a 200-mL three-neck flask having a rotor set therein and equipped with a three-way cock and a thermometer, and 50 mL of toluene and 30 mL of diethyl ether were added to dissolve the compound. This was cooled to −70° C. in a dry ice-isopropyl alcohol bath, and 7.2 mL (13.0 mmol) of n-butyllithium/hexane (1.64 M solution) was added and stirred for 80 minutes. The cooling bath was removed and the mixture was restored to room temperature, and the solvent was evaporated away. 80 mL of toluene and 4 mL of diethyl ether were added to dissolve the mixture, and cooled to −70° C. 1.90 g (5.9 mmol) of hafnium tetrachloride was added, and immediately the cooling bath was removed and the mixture was gradually restored to room temperature. From $^1$H-NMR thereof, the stereoisomeric composition of the resultant complex was racemic form/meso form=33/67. The solvent was evaporated away, 30 ml of DME was added and heated with stirring at 60° C. for 5 hours. The supernatant was collected through decantation. The solid was dried under reduced pressure, 50 mL of toluene was added, and the insoluble matter was removed through filtration. The filtrate was concentrated, and the resultant solid was washed with a small amount of hexane and dried under reduced pressure to give isopropylidenebis (4-(3-t-butylphenyl)-1-indenyl)hafnium dichloride as a pale yellow powdery solid. The racemic purity of the compound was 100%, and the yield thereof was 2.24 g and 51%.

$^1$H-NMR (400 MHz, CDCl$_3$): δ7.79 (d, J=8.8 Hz, 2H), 7.72 (s, 2H), 7.39-7.34 (m, 6H), 6.29 (d, J=6.4 Hz, 2H), 7.13-7.10 (m, 2H), 6.74 (dd, J=3.6 Hz, 6H), 6.19 (d, J=3.6 Hz, 2H), 2.41 (s, 6H), 1.29 (s, 18H).

(4) Synthesis of isopropylidenebis(4-(3-t-butylphenyl)-1-indenyl)dimethylhafnium 0.51 g (0.64 mmol) of isopropylidenebis(4-(3-t-butylphenyl)-1-indenyl)hafnium dichloride and 30 ml of toluene were put in a 100-mL side-arm flask having a rotor set therein, and dissolved. 2.2 mL (6.6 mmol) of methylmagnesium bromide/diethyl ether (3.0 M solution) was added, and then heated with stirring at 60° C. for 9 hours. At room temperature, 0.63 ml (5.0 mmol) of trimethylsilyl chloride was added, stirred for 20 minutes, and 5 ml of dioxane was added and stirred for 30 minutes. The insoluble matter was removed through filtration, and the filtrate was concentrated to give a yellow solid. This was washed with a small amount of hexane, and the supernatant was removed three times through decantation, and the residue was dried under reduced pressure to give a pale yellow powdery solid of isopropylidenebis(4-(3-t-butylphenyl)-1-indenyl)dimethylhafnium. The racemic form purity of the compound was 100%, the yield thereof was 0.36 g and 76%.

$^1$H-NMR (400 MHz, $C_6D_6$): δ7.88 (s, 2H), 7.57-7.54 (m, 2H), 7.35 (d, J=8.8 Hz, 2H), 7.24-7.20 (m, 6H), 6.86-6.82 (m, 4H), 5.56 (d, J=3.6 Hz, 2H), 1.77 (s, 6H), 1.23 (s, 18H), −0.91 (s, 6H).

Synthesis of Metallocene Compound J: isopropylidenebis[4-(2,5-dimethylphenyl)-1-indenyl]dimethylhafnium

[Chem. 14]

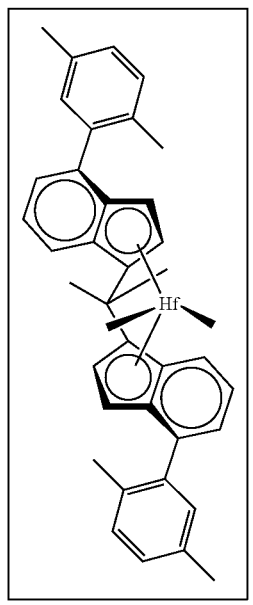

(Metallocene Compound J)

(1) Synthesis of 4-(2,5-dimethylphenyl)indene 38 g (180 mmol) of tripotassium phosphate, 100 mL of distilled water, 100 mL of DME, 10 g (66.7 mmol) of 2,5-dimethylphenylboronic acid, 10.8 g (55.4 mmol) of 7-bromo-1H-indene, 969 mg (1.38 mmol) of dichlorobis(triphenylphosphine)palladium, and 1.30 g (4.96 mmol) of triphenyl phosphine were put into a 500-mL glass reactor in that order, and then heated under reflux at 90° C. for 16 hours. This was left cooled to room temperature, and the reaction liquid was poured into 100 mL of distilled water, transferred into a separatory funnel, and extracted three times with hexane. 6 mL of concentrated hydrochloric acid was added to the hexane solution at room temperature, then stirred at room temperature for 30 minutes, the palladium compound was precipitated, filtered away through filter paper, and the filtrate was washed three times each with saturated saline water and distilled water, and then dried with sodium sulfate. Sodium sulfate was filtered away, the solvent was evaporated away under reduced pressure, and the residue was purified through silica gel column chromatography (developing solvent, hexane/diisopropyl ether=20/1) to give 12.2 g (yield 100%) of 4-(2,5-dimethylphenyl)indene as a colorless liquid.

(2) Synthesis of 2,2-bis(4-(2,5-dimethylphenyl)-inden-1-yl)propane 12.2 g (55.4 mmol) of 4-(2,5-dimethylphenyl)indene, 85 mL of DME and 4.26 g (75.9 mmol) of potassium hydroxide were put in a 200-mL glass reactor, and heated under reflux at 90° C. for 2 hours. The reaction liquid was cooled to 0° C., 2.05 mL (27.2 mmol) of acetone was added, and then heated under reflux at 90° C. for 6 hours. The reaction liquid was cooled to room temperature, 100 mL of distilled water was added, cooled to 0° C. in an ice bath, 6 mL of concentrated hydrochloric acid was added, and then stirred at room temperature for 15 minutes. The reaction liquid was transferred into a separatory funnel, extracted three times with diisopropyl ether, and the resultant diisopropyl ether solution was washed three times each with saturated saline water and distilled water, and then dried with sodium sulfate. Sodium sulfate was filtered away, the solvent concentrated, and the residue was recrystallized at −20° C. to give 6.47 g (yield 49%) of 2,2-bis(4-(2,5-dimethylphenyl)-inden-1-yl)propane as a white solid.

$^1$H-NMR (400 MHz, 400 MHz, $CDCl_3$): δ7.34 (dd, 2H), 7.22-7.00 (m, 8H), 6.91 (d, 2H), 6.51 (t, 2H), 3.15 (brs, 4H), 2.34 (s, 6H), 2.07 (s, 6H), 1.79 (s, 6H).

(3) Synthesis of isopropylidenebis(4-(2,5-dimethylphenyl)-1-indenyl)hafnium dichloride 3.01 g (6.3 mmol) of 2,2-bis(4-(2,5-dimethylphenyl)-inden-1-yl)propane was put in a 200-mL three-neck flask having a rotor set therein and equipped with a three-way cock and a thermometer, and 50 mL of toluene and 30 mL of diethyl ether were added to dissolve the compound. This was cooled to −70° C. in a dry ice-isopropyl alcohol bath, and 8.0 mL (13.0 mmol) of n-butyllithium/hexane (1.63 M solution) was added and stirred for 60 minutes. The cooling bath was removed and the mixture was restored to room temperature, and the solvent was evaporated away under reduced pressure. 80 mL of toluene and 5 mL of diethyl ether were added to dissolve the mixture, and cooled to −70° C. 2.11 g (6.6 mmol) of hafnium tetrachloride was added, and immediately the cooling bath was removed and the mixture was gradually restored to room temperature. The solvent was evaporated away, and 50 mL of DME was added and heated with stirring at 60° C. for 6 hours. The supernatant was removed through decantation, the solid was dried under reduced pressure, 60 mL of toluene was added, and the insoluble matter was removed through filtration. The filtrate was concentrated, and the resultant solid was washed with a small amount of hexane, and dried under reduced pressure to give isopropylidenebis(4-(2,5-dimethylphenyl)-1-indenyl)hafnium dichloride as a yellow powdery solid. The racemic purity of the compound was 100%, and the yield thereof was 1.60 g and 35%.

¹H-NMR (400 MHz, CDCl₃): δ7.74 (d, J=8.8 Hz, 2H), 7.31 (s, 2H), 7.19-7.03 (m, 10H), 6.31 (s, 2H), 6.12 (s, 2H), 2.40 (s, 6H), 2.30 (s, 6H), 62.05 (s, 6H).

(4) Synthesis of isopropylidenebis(4-(2,5-dimethylphenyl)-1-indenyl)dimethylhafnium 0.55 g (0.76 mmol) of isopropylidenebis(4-(2,5-dimethylphenyl)-1-indenyl)hafnium dichloride and 30 ml of toluene were put in a 100-mL side-arm flask having a rotor set therein, and dissolved. 2.5 mL (7.5 mmol) of methylmagnesium bromide/diethyl ether (3.0 M solution) was added, and then heated with stirring at 60° C. for 6 hours. At room temperature, 0.68 ml (5.4 mmol) of trimethylsilyl chloride was added, stirred for 20 minutes, and 5 ml of dioxane was added and stirred for 30 minutes. The precipitate was removed through filtration, and the resulting filtrate was concentrated to give a yellow solid. This was washed with a small amount of hexane, and the supernatant was removed through decantation, and the residue was dried under reduced pressure to give a pale yellow powdery solid of isopropylidenebis(4-(2,5-dimethylphenyl)-1-indenyl)dimethylhafnium. The racemic form purity of the compound was 100%, the yield thereof was 0.42 g and 80%.

¹H-NMR (400 MHz, C₆D₆): δ7.48 (s, 2H), 7.31 (d, J=8.8 Hz, 2H), 7.11 (d, J=7.8 Hz, 2H), 7.04 (d, J=6.6 Hz, 2H), 6.97 (d, J=7.8 Hz, 2H), 6.82-6.78 (m, 2H), 6.41 (s, 2H), 5.60 (d, J=3.6 Hz, 2H), 2.16 (s, 6H), 2.09 (s, 6H), 1.77 (s, 6H), −0.94 (s, 6H).

Synthesis of Metallocene Compound K: isopropylidenebis(4-(2,3-dimethylphenyl)-1-indenyl)dimethylhafnium

[Chem. 15]

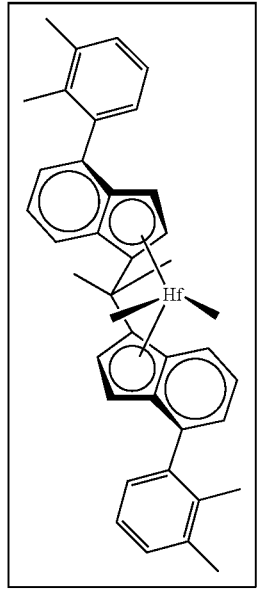

(Metallocene Compound K)

(1) Synthesis of 4-(2,3-dimethylphenyl)indene 38 g (180 mmol) of tripotassium phosphate, 100 mL of distilled water, 100 mL of DME, 10 g (66.7 mmol) of 2,3-dimethylphenylboronic acid, 10.8 g (55.4 mmol) of 7-bromo-1H-indene, 1.0 g (1.42 mmol) of dichlorobis(triphenylphosphine)palladium, and 1.30 g (4.96 mmol) of triphenyl phosphine were put into a 500-mL glass reactor in that order, and then heated under reflux at 90° C. for 11 hours. This was left cooled to room temperature, and the reaction liquid was poured into 100 mL of distilled water, transferred into a separatory funnel, and extracted three times with hexane. 6 mL of concentrated hydrochloric acid was added to the hexane solution at room temperature, then stirred at room temperature for 30 minutes, the palladium compound was precipitated, filtered away through filter paper, and the filtrate was washed three times each with saturated saline water and distilled water, and then dried with sodium sulfate. Sodium sulfate was filtered away, the solvent was evaporated away under reduced pressure, and the residue was purified through silica gel column chromatography (developing solvent, hexane/diisopropyl ether=20/1) to give 11.66 g (yield 96%) of 4-(2,3-dimethylphenyl) indene as a colorless oil.

(2) Synthesis of 2,2-bis(4-(2,3-dimethylphenyl)-inden-1-yl)propane 11.66 g (52.9 mmol) of 4-(2,3-dimethylphenyl)indene, 85 mL of DME and 4.00 g (71.3 mmol) of potassium hydroxide were put in a 200-mL glass reactor, and heated under reflux at 90° C. for 2 hours. The reaction liquid was cooled to 0° C., 1.95 mL (26.5 mmol) of acetone was added, and then heated under reflux at 90° C. for 7 hours. The reaction liquid was cooled to room temperature, 100 mL of distilled water was added, cooled to 0° C. in an ice bath, 6 mL of concentrated hydrochloric acid was added, and then stirred at room temperature for 15 minutes. 100 mL of diisopropyl ether was added to the reaction liquid, stirred, and the resultant suspension was filtered through filter paper, and the solid on the filtrate was washed with hexane to give 7.24 g (yield 57%) of 2,2-bis(4-(2,3-dimethylphenyl)-inden-1-yl) propane as a white solid.

¹H-NMR (400 MHz, CDCl₃); racemic form: 87.35 (d, 2H), 7.22-7.04 (m, 8H), 6.92 (d, 2H), 6.52 (t, 2H), 3.20 (d, 2H), 3.06 (d, 2H), 2.35 (s, 6H), 2.02 (brs, 6H), 1.80 (s, 6H).

(3) Synthesis of racemic-isopropylidenebis(4-(2,3-dimethylphenyl)-1-indenyl)hafnium dichloride 2.60 g (5.00 mmol) of 2,2-bis(4-(2,3-dimethylphenyl)-inden-1-yl)propane and 50 mL of diethyl ether were put in a 200-mL glass reactor, and cooled to −70° C. in a dry ice-heptane bath. 6.2 mL (10.2 mmol) of n-butyllithium/n-hexane solution (1.64 mol/L) was dropwise added thereto, and stirred at room temperature for 4 hours. The solvent was evaporated away from the reaction liquid under reduced pressure, 80 mL of toluene was added, and cooled to −70° C. in a dry ice-heptane bath. 1.60 g (5.00 mmol) of hafnium tetrachloride was added thereto. Subsequently, while gradually restored to room temperature, this was stirred for 17 hours. The ratio of the racemic form to the meso form formed in this stage was 3/7.

The solvent was evaporated away from the reaction liquid under reduced pressure, and 35 mL of DME was added thereto and stirred at 60° C. for 5 hours. The reaction liquid was cooled to room temperature, filtered through glass frit, and the solid was collected through filtration to give 2.25 g of a racemic form of isopropylidenebis[4-(2,3-dimethylphenyl)-1-indenyl]hafnium dichloride containing lithium chloride, as a yellow solid.

$^1$H-NMR (400 MHz, CDCl$_3$): δ=7.74 (d, 2H) 7.31 (dd, 2H), 7.20-7.00 (m, 8H), 6.25 (d, 2H), 6.12 (d, 2H), 2.40 (s, 6H), 2.31 (s, 6H), 1.95 (s, 6H).

(4) Synthesis of racemic-isopropylidenebis[4-(2,3-methylphenyl)-1-indenyl]dimethylhafnium 1.00 g of the above-mentioned, lithium chloride-containing isopropylidenebis[4-(2,3-dimethylphenyl)-1-indenyl]hafnium dichloride (the content is 1.37 mmol or less) and 50 mL of toluene were put in a 100-mL glass reactor. 3.2 mL (9.6 mmol) of methylmagnesium bromide/diethyl ether solution (3.0 mol/L) was dropwise added thereto at room temperature, and stirred at 80° C. for 4.5 hours. The reaction liquid was cooled to 0° C. in an ice bath, then 0.84 mL (6.8 mmol) of chlorotrimethylsilane was added thereto, stirred at room temperature for 10 minutes, and subsequently 1.70 mL (20.5 mmol) of 1,4-dioxane was added, and further stirred at room temperature for 30 minutes. The suspension was filtered through Celite, the solvent was evaporated away under reduced pressure, and the resultant yellow solid was suspended in 10 mL of hexane, filtered through glass frit, and the solid was further washed twice with 3 mL of hexane to give 260 mg of a racemic form of isopropylidenebis[4-(2,3-dimethylphenyl)-1-indenyl]dimethylhafnium as a yellow solid. The yield based on the ligand was 26% (presumed that all the dichloro form was used).

$^1$H-NMR (400 MHz, C$_6$D$_6$): δ=7.63 (d, 2H), 7.42 (d, 2H), 7.30-7.06 (m, 6H), 6.91 (dd, 2H), 6.48 (d, 2H), 5.71 (d, 2H), 2.21 (s, 6H), 2.15 (s, 6H), 1.88 (s, 6H), −0.87 (s, 6H).

Synthesis of Metallocene Compound L: isopropylidenebis[4-(3-methylphenyl)-1-indenyl]dimethylhafnium

[Chem. 16]

(Metallocene Compound L)

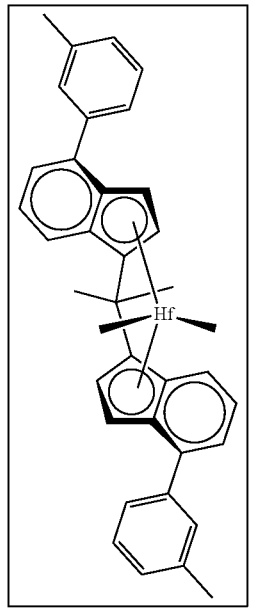

(1) Synthesis of 4-(3-methylphenyl)indene 38 g (180 mmol) of tripotassium phosphate, 100 mL of distilled water, 100 mL of DME, 10 g (73.6 mmol) of 3-methylphenylboronic acid, 12.0 g (61.5 mmol) of 7-bromo-1H-indene, 323 mg (0.460 mmol) of dichlorobis(triphenylphosphine)palladium, and 432 mg (1.65 mmol) of triphenyl phosphine were put into a 500-mL glass reactor in that order, and then heated under reflux at 90° C. for 8 hours. This was left cooled to room temperature, then the reaction liquid was poured into 100 mL of distilled water, transferred into a separatory funnel, and extracted three times with hexane. At room temperature 6 mL of concentrated hydrochloric acid was added to the hexane solution, then stirred at room temperature for 30 minutes, the palladium compound was precipitated, filtered out through filter paper, and the filtrate was washed three times each with saturated saline water and distilled water, and dried with sodium sulfate. Sodium sulfate was filtered away, the solvent was evaporated away under reduced pressure, and the residue was purified through silica gel column chromatography (developing solvent, hexane/diisopropyl ether=20/1) to give 12.7 g (yield 100%) of 4-(3-methylphenyl)indene as a colorless oil.

(2) Synthesis of 2,2-bis(4-(3-methylphenyl)-inden-1-yl)propane 12.7 g (61.6 mmol) of 4-(3-methylphenyl)indene, 85 mL of DME, and 4.66 g (83.1 mmol) of potassium hydroxide were put in a 200-mL glass reactor, and heated under reflux at 90° C. for 2 hours. The reaction liquid was cooled to 0° C., then 2.25 mL (30.6 mmol) of acetone was added thereto and heated under reflux at 90° C. for 7 hours. The reaction liquid was cooled to room temperature, then 100 mL of distilled water was added thereto, cooled to 0° C. in an ice bath, 6 mL of concentrated hydrochloric acid was added thereto, and stirred at room temperature for 15 minutes. 100 mL of diisopropyl ether was added to the reaction liquid and stirred, and then the resultant suspension was filtered through filter paper, and the solid on the filter paper was washed with distilled water to give 9.65 g (yield 69%) of 2,2-bis(4-(3-methylphenyl)-inden-1-yl)propane as a yellow solid.

$^1$H-NMR (400 MHz, CDCl$_3$): δ7.44-7.30 (m, 8H), 7.22-7.06 (m, 6H), 6.58 (t, 2H), 3.48 (d, 4H), 2.42 (s, 6H), 1.80 (s, 6H).

(3) Synthesis of racemic-isopropylidenebis[4-(3-methylphenyl)-1-indenyl]hafnium dichloride 2.40 g (5.00 mmol) of 2,2-bis(4-(3-methylphenyl)-inden-1-yl)propane and 50 ml of diethyl ether were put in a 200-mL glass reactor, and cooled to −70° C. in a dry ice-heptane bath. 6.2 mL (10.2 mmol) of n-butyl lithium/n-hexane solution (1.64 mol/L) was dropwise added thereto, and stirred at room temperature for 4 hours. The solvent was evaporated away under reduced pressure from the reaction liquid, 60 mL of toluene was added, and cooled to −70° C. in a dry ice/heptane bath. 1.60 g (5.00 mmol) of hafnium tetrachloride was added thereto. Subsequently, while gradually restored to room temperature, this was stirred for 16 hours. The ratio of the racemic form to the meso form formed in this stage was 3/4.

The solvent was evaporated away under reduced pressure from the reaction liquid, 13 mL of DME was added, and stirred at 60° C. for 5 hours. The reaction liquid was cooled to room temperature, then filtered through glass frit, and the solid was washed twice with 3 ml of DME to give 2.79 g of a racemic form of isopropylidenebis[4-(3-methylphenyl)-1-indenyl]hafnium dichloride containing lithium chloride, as an orange solid.

$^1$H-NMR (400 MHz, CDCl$_3$): δ=7.76 (d, 2H), 7.41 (s, 2H), 7.38 (d, 2H), 7.31 (t, 2H), 7.26 (d, 2H), 7.16 (d, 2H), 7.10 (dd, 2H), 6.73 (d, 2H), 6.17 (d, 2H), 2.40 (s, 6H), 2.37 (s, 6H).

(4) Synthesis of racemic-isopropylidenebis[4-(3-methylphenyl)-1-indenyl]dimethylhafnium 1.00 g of the above-mentioned, lithium chloride-containing isopropylidenebis[4-(3-methylphenyl)-1-indenyl]hafnium dichloride (the content is 1.43 mmol or less) and 50 mL of toluene were put in a 100-mL glass reactor. 3.3 mL (9.9 mmol) of methylmagnesium bromide/diethyl ether solution (3.0 mol/L) was dropwise added thereto at room temperature, and stirred at 80° C. for 2 hours. The reaction liquid was cooled to 0° C. in an ice bath, then 0.90 mL (7.1 mmol) of chlorotrimethylsilane was added thereto, stirred at room temperature for 30 minutes, and subsequently 1.80 mL (21.0 mmol) of 1,4-dioxane was added, and further stirred at room temperature for 40 minutes. The suspension was filtered through Celite, and the solvent was evaporated away under reduced pressure. The resultant yellow solid was suspended in 10 mL of hexane, filtered through glass frit, and the solid was further washed three times with 5 mL of hexane to give 678 mg of a racemic form of isopropylidenebis[4-(3-methylphenyl)-1-indenyl]dimethylhafnium as a yellow solid. The yield based on the ligand was 56% (presumed that all the dichloro form was used).

$^1$H-NMR (400 MHz, C$_6$D$_6$): δ=7.59 (d, 2H), 7.58 (s, 2H), 7.38 (d, 2H), 7.26-7.12 (m, 4H), 6.98 (d, 2H), 6.87 (d, 2H), 6.85 (dd, 2H), 5.61 (d, 2H), 2.14 (s, 6H), 1.80 (s, 6H), −0.92 (s, 6H).

Synthesis of Metallocene Compound M:
isopropylidenebis[4-(2-methylphenyl)-1-indenyl]dimethylhafnium

[Chem. 17]

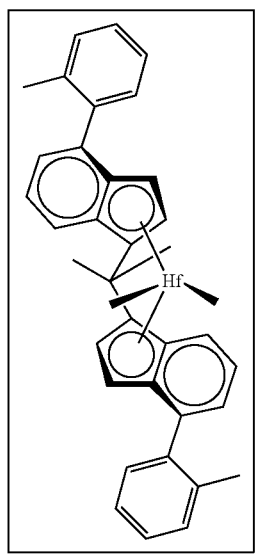

(Metallocene Compound M)

(1) Synthesis of 4-(2-methylphenyl)indene 38 g (180 mmol) of tripotassium phosphate, 100 mL of distilled water, 100 mL of DME, 10 g (73.6 mmol) of 2-methylphenylboronic acid, 12.0 g (61.5 mmol) of 7-bromo-1H-indene, 1.00 g (1.42 mmol) of dichlorobis(triphenylphosphine)palladium, and 1.30 g (4.96 mmol) of triphenyl phosphine were put into a 500-mL glass reactor in that order, and then heated under reflux at 90° C. for 11 hours. This was left cooled to room temperature, then the reaction liquid was poured into 100 mL of distilled water, transferred into a separatory funnel, and extracted three times with hexane. At room temperature 6 mL of concentrated hydrochloric acid was added to the hexane solution, then stirred at room temperature for 30 minutes, the palladium compound was precipitated, filtered out through filter paper, and the filtrate was washed three times each with saturated saline water and distilled water, and dried with sodium sulfate. Sodium sulfate was filtered away, the solvent was evaporated away under reduced pressure, and the residue was purified through silica gel column chromatography (developing solvent, hexane/diisopropyl ether=20/1) to give 12.7 g (yield 100%) of 4-(2-methylphenyl)indene as a colorless oil.

(2) Synthesis of 2,2-bis(4-(2-methylphenyl)-inden-1-yl)propane 13.0 g (63.0 mmol) of 4-(2-methylphenyl)indene, 90 mL of DME, and 4.77 g (85.0 mmol) of potassium hydroxide were put in a 200-mL glass reactor, and heated under reflux at 90° C. for 2 hours. The reaction liquid was cooled to 0° C., then 2.35 mL (32.0 mmol) of acetone was added thereto and heated under reflux at 90° C. for 7 hours. The reaction liquid was cooled to room temperature, then 100 mL of distilled water was added thereto, cooled to 0° C. in an ice bath, 7.2 mL of concentrated hydrochloric acid was added thereto, and stirred at room temperature for 15 minutes. The reaction liquid was filtered through filter paper, and the solid on the filter paper was washed with distilled water and hexane to give 9.58 g (yield 67%) of 2,2-bis(4-(2-methylphenyl)-inden-1-yl)propane as a white solid.

$^1$H-NMR (400 MHz, CDCl$_3$): δ7.35 (d, 2H), 7.33-7.18 (m, 8H), 7.11 (t, 2H), 6.93 (d, 2H), 6.25 (t, 2H), 3.15 (brs, 4H), 2.12 (s, 6H), 1.80 (s, 6H).

(3) Synthesis of racemic-isopropylidenebis[4-(2-methylphenyl)-1-indenyl]hafnium dichloride 2.26 g (5.00 mmol) of 2,2-bis(4-(2-methylphenyl)-inden-1-yl)propane and 50 ml of diethyl ether were put in a 200-mL glass reactor, and cooled to −70° C. in a dry ice-heptane bath. 6.2 mL (10.2 mmol) of n-butyl lithium/n-hexane solution (1.64 mol/L) was dropwise added thereto, and stirred at room temperature for 4 hours. The solvent was evaporated away under reduced pressure from the reaction liquid, 60 mL of toluene was added, and cooled to −70° C. in a dry ice/heptane bath. 1.60 g (5.00 mmol) of hafnium tetrachloride was added thereto. Subsequently, while gradually restored to room temperature, this was stirred for 16 hours. The ratio of the racemic form to the meso form formed in this stage was 3/4.

The solvent was evaporated away under reduced pressure from the reaction liquid, 13 mL of DME was added, and stirred at 60° C. for 5 hours. The reaction liquid was cooled to room temperature, then filtered through glass frit, and the solid was washed twice with 3 ml of DME to give 2.57 g of a racemic form of isopropylidenebis[4-(2-methylphenyl)-1-indenyl]hafnium dichloride containing lithium chloride, as an orange solid.

$^1$H-NMR (400 MHz, CDCl$_3$): δ=7.79 (d, 2H), 7.44 (brs, 2H), 7.24 (brs, 6H), 7.31 (t, 2H), 7.10 (d, 2H), 7.06 (t, 2H), 6.26 (brs, 2H), 6.13 (brs, 2H), 2.40 (s, 6H), 2.07 (s, 6H).

(4) Synthesis of racemic-isopropylidenebis[4-(2-methylphenyl)-1-indenyl]dimethylhafnium 1.00 g of the above-mentioned, lithium chloride-containing isopropylidenebis[4-(2-methylphenyl)-1-indenyl]hafnium dichloride (the content is 1.43 mmol or less) and 50 mL of toluene were put in a 100-mL glass reactor. 3.3 mL (9.9 mmol) of methylmagnesium bromide/diethyl ether solution (3.0 mol/L) was dropwise added thereto at room temperature, and stirred at 80° C. for 2 hours. The reaction liquid was cooled to 0° C. in an ice bath, then 0.90 mL (7.1 mmol) of chlorotrimethylsilane was added thereto, stirred at room temperature for 30 minutes, and subsequently 1.85 mL (21.6 mmol) of 1,4-dioxane was added, and further stirred at room temperature for 40 minutes. The suspension was filtered through Celite, and the solvent was evaporated away under reduced pressure. The resultant yellow solid was suspended in 5 mL of hexane, filtered through glass frit, and the solid was further washed three times with 3 mL of hexane to give 688 mg of a racemic form of isopropylidenebis[4-(2-methylphenyl)-1-indenyl]dimethylhafnium as a yellow solid. The yield based on the ligand was 54% (presumed that all the dichloro form was used).

$^1$H-NMR (400 MHz, C$_6$D$_6$): δ=7.62 (brs, 2H), 7.30 (d, 2H), 7.20-7.10 (m, 6H), 7.00 (d, 2H), 6.78 (dd, 2H), 6.35 (brs, 2H), 5.57 (brs, 2H), 2.16 (s, 6H), 1.76 (s, 6H), −0.99 (s, 6H).

Synthesis of Metallocene Compound N: cyclobutlidenebis[4-(4-isopropylphenyl)-1-indenyl]dimethylhafnium

[Chem. 18]

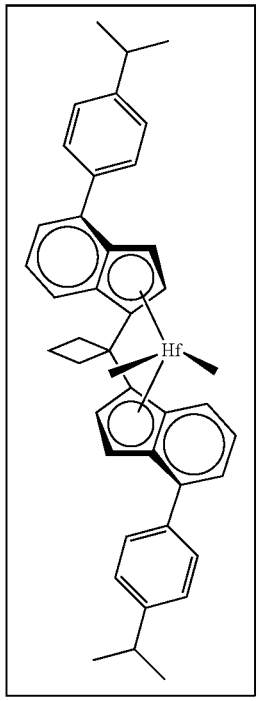

(Metallocene Compound N)

(1) Synthesis of 1,1-bis[4-(4-isopropylphenyl)-inden-1-yl]cyclobutane 12.7 g (54.2 mmol) of 4-(4-isopropylphenyl)indene, 85 mL of DME, and 4.11 g (75.9 mmol) of potassium hydroxide were put in a 200-mL glass reactor, and heated under reflux at 90° C. for 2 hours. The reaction liquid was cooled to 0° C., then 2.05 mL (27.2 mmol) of cyclobutanone was added thereto and heated under reflux at 90° C. for 6 hours. The reaction liquid was cooled to room temperature, then 100 mL of distilled water was added thereto, cooled to 0° C. in an ice bath, 6 mL of concentrated hydrochloric acid was added thereto, and stirred at room temperature for 15 minutes. The reaction liquid was transferred into a separatory funnel, extracted three times with diisopropyl ether, and the resultant diisopropyl ether solution was washed three times each with saturated saline water and distilled water, and dried with sodium sulfate. Sodium sulfate was filtered away, the solvent was evaporated away under reduced pressure, and the resultant crude product was purified through silica gel column chromatography (developing solvent: diisopropyl ether/hexane=1/20) to give 11.0 g (yield 78%) of 1, 1-b is [4-(4-isopropylphenyl)-inden-1-yl]cyclobutane as an orange solid.

$^1$H-NMR (400 MHz, CDCl$_3$): δ7.44 (d, 4H), 7.39 (d, 2H), 7.29 (d, 4H), 7.22 (t, 2H), 7.13 (d, 2H), 6.69 (s, 2H), 3.50 (s, 4H), 2.97 (sept, 2H), 2.78 (t, 4H), 2.11 (quint, 2H), 1.31 (d, 12H).

(2) Synthesis of racemic-cyclobutylidenebis[4-(4-isopropylphenyl)-indenyl]hafnium dichloride 3.12 g (6.00 mmol) of 1,1-bis[4-(4-isopropylphenyl)-inden-1-yl]cyclobutane and 60 ml of diethyl ether were put in a 200-mL glass reactor, and cooled to −70° C. in a dry ice-heptane bath. 7.5 mL (12.3 mmol) of n-butyl lithium/n-hexane solution (1.64 mol/L) was dropwise added thereto, and stirred at room temperature for 4 hours. The solvent was evaporated away under reduced pressure from the reaction liquid, 70 mL of toluene was added, and cooled to −70° C. in a dry ice/heptane bath. 1.92 g (6.00 mmol) of hafnium tetrachloride was added thereto. Subsequently, while gradually restored to room temperature, this was stirred for 17 hours. The ratio of the racemic form to the meso form formed in this stage was 1/2.

The solvent was evaporated away under reduced pressure from the reaction liquid, 20 mL of DME was added, and stirred at 60° C. for 5 hours. The reaction liquid was, as such, filtered through glass frit, and the solid was collected through filtration to give 1.62 g of a racemic form of cyclobutylidenebis[4-(4-isopropylphenyl)-indenyl]hafnium dichloride containing lithium chloride, as an orange solid.

$^1$H-NMR (400 MHz, CDCl$_3$): δ=7.43 (d, 2H), 7.40 (dd, 2H), 7.29 (d, 4H), 7.22 (t, 2H), 7.13 (dd, 2H), 6.69 (t, 2H), 3.50 (d, 2H), 2.97 (sept, 2H), 2.78 (t, 4H), 2.11 (quint, 2H), 1.31 (d, 12H).

(3) Synthesis of racemic-cyclobutylidenebis[4-(4-isopropylphenyl)-1-indenyl]dimethylhafnium 1.00 g of the above-mentioned, lithium chloride-containing 1,1-cyclobutylidenebis[4-(4-isopropylphenyl)-indenyl]hafnium dichloride (the content is 1.30 mmol or less) and 50 mL of toluene were put in a 100-mL glass reactor. 3.0 mL (9.0 mmol) of methylmagnesium bromide/diethyl ether solution (3.0 mol/L) was dropwise added thereto at room temperature, and stirred at 80° C. for 3 hours. The reaction liquid was cooled to 0° C. in an ice bath, then 0.82 mL (6.5 mmol) of chlorotrimethylsilane was added thereto, stirred at room temperature for 30 minutes, and subsequently 1.70 mL (19.9 mmol) of 1,4-dioxane was added, and further stirred at room temperature for 1 hour. The suspension was filtered through Celite, and the solvent was evaporated away under reduced pressure. The resultant yellow solid was suspended in 5 mL of hexane, filtered through glass frit, and the solid was further washed three times with 5 mL of hexane to give 612 mg of a racemic form of 1,1-cyclobutylidenebis[4-(4-isopropylphenyl)-1-indenyl]dimethylhafnium as a yellow solid. The yield based on the ligand was 23% (presumed that all the dichloro form was used).

$^1$H-NMR (400 MHz, C$_6$D$_6$): δ=7.74 (d, 4H), 7.22 (d, 2H), 7.17 (d, 4H), 7.13 (d, 2H), 6.87 (d, 2H), 6.83 (dd, 2H), 5.53 (d, 2H), 3.06 (quartet, 2H), 2.72 (sep, 2H), 2.60 (quartet, 2H), 2.07 (quintet, 2H), 1.12 (d, 12H), −0.93 (s, 6H).

Synthesis of Metallocene Compound O: cyclobutlidenebis[4-(3,5-dimethylphenyl)-1-indenyl]dimethyl hafnium

[Chem. 19]

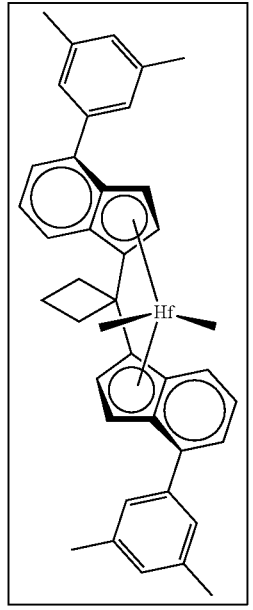

(Metallocene Compound O)

(1) Synthesis of 1,1-bis[4-(3,5-dimethylphenyl)-inden-1-yl]cyclobutane 8.69 g (39.0 mmol) of 4-(3,5-dimethylphenyl)indene, 80 mL of DME, and 2.84 g (50.7 mmol) of potassium hydroxide were put in a 200-mL glass reactor, and heated under reflux at 90° C. for 1 hour. The reaction liquid was cooled to 0° C., then a solution of cyclobutanone (1.33 g, 19.1 mmol)/DME (40 mL) was added thereto and heated under reflux at 90° C. for 16 hours. The reaction liquid was cooled to room temperature, then 200 mL of distilled water was added thereto, transferred into a separatory funnel, extracted three times with ethyl acetate, and the resultant ethyl acetate solution was washed three times each with saturated saline water and distilled water, and dried with sodium sulfate. Sodium sulfate was filtered away, the solvent was evaporated away under reduced pressure, and the resultant crude product was purified through silica gel column chromatography (developing solvent: petroleum ether) to give 4.50 g (yield 49%) of 1, 1-bis[4-(3,5-dimethylphenyl)-inden-1-yl] cyclobutane as a yellow solid.

$^1$H-NMR (400 MHz, CDCl$_3$): δ7.39 (d, 2H), 7.22 (t, 2H), 7.11 (s, 4H), 7.11 (d, 2H), 7.00 (s, 2H), 6.68 (s, 2H), 3.48 (d, 4H), 2.77 (t, 4H), 2.37 (s, 12H), 2.11 (quint, 2H).

(2) Synthesis of racemic-cyclobutylidenebis[4-(3,5-dimethylphenyl)-indenyl]hafnium dichloride 2.46 g (5.00 mmol) of 1,1-bis[4-(3,5-dimethylphenyl)-inden-1-yl]cyclobutane and 50 ml of diethyl ether were put in a 200-mL glass reactor, and cooled to −70° C. in a dry ice-heptane bath. 6.2 mL (10.2 mmol) of n-butyl lithium/n-hexane solution (1.64 mol/L) was dropwise added thereto, and stirred at room temperature for 4 hours. The solvent was evaporated away under reduced pressure from the reaction liquid, 60 mL of toluene was added, and cooled to −70° C. in a dry ice/heptane bath. 1.60 g (5.00 mmol) of hafnium tetrachloride was added thereto. Subsequently, while gradually restored to room temperature, this was stirred for 16 hours. The ratio of the racemic form to the meso form formed in this stage was 42/58.

The solvent was evaporated away under reduced pressure from the reaction liquid, 10 mL of DME was added, and stirred at 60° C. for 5 hours. The reaction liquid was, as such, filtered through glass fit, and the solid washed twice with 3 mL of DME to give 2.41 g of a racemic form of cyclobutylidenebis[4-(3,5-dimethylphenyl)-1-indenyl]hafnium dichloride containing lithium chloride, as an orange solid.

$^1$H-NMR (400 MHz, CDCl$_3$): δ=7.48 (d, 2H), 7.25 (d, 2H), 7.20 (s, 4H), 7.06 (dd, 2H), 6.98 (s, 2H), 6.68 (d, 2H), 6.06 (d, 2H), 3.58 (quartet, 2H), 3.15 (quartet, 2H), 2.49 (quintet, 2H), 2.32 (s, 12H).

(3) Synthesis of racemic-cyclobutylidenebis[4-(3,5-dimethylphenyl)-1-indenyl]dimethylhafnium 1.00 g of the above-mentioned, lithium chloride-containing cyclobutylidenebis[4-(3,5-dimethylphenyl)-1-indenyl] hafnium dichloride (the content is 1.35 mmol or less) and 50 mL of toluene were put in a 100-mL glass reactor. 3.2 mL (9.4 mmol) of methylmagnesium bromide/diethyl ether solution (3.0 mol/L) was dropwise added thereto at room temperature, and stirred at 80° C. for 3 hours. The reaction liquid was cooled to 0° C. in an ice bath, then 0.85 mL (6.7 mmol) of chlorotrimethylsilane was added thereto, stirred at room temperature for 30 minutes, and subsequently 1.75 mL (20.5 mmol) of 1,4-dioxane was added, and further stirred at room temperature for 40 minutes. The suspension was filtered through Celite, and the solvent was evaporated away under reduced pressure. The resultant yellow solid was suspended in 5 mL of hexane, filtered through glass frit, and the solid was further washed three times with 5 mL of hexane to give 622 mg of a racemic form of cyclobutylidenebis[4-(3,5-dimethylphenyl)-1-indenyl]dimethylhafnium as a yellow solid. The yield based on the ligand was 43% (presumed that all the dichloro form was used).

$^1$H-NMR (400 MHz, C$_6$D$_6$): δ=7.45 (s, 4H), 7.23 (d, 2H), 7.14 (d, 2H), 6.89 (d, 2H), 6.84 (dd, 2H), 6.81 (s, 1H), 5.57 (d, 2H), 3.07 (quartet, 2H), 2.62 (quartet, 2H), 2.15 (s, 12H), 2.09 (quintet, 2H), −0.91 (s, 6H).

Synthesis of Metallocene Compound P (Comparative Example): dimethylsilylenebis(2-methyl-4-phenyl-1-indenyl)dimethylhafnium

[Chem. 20]

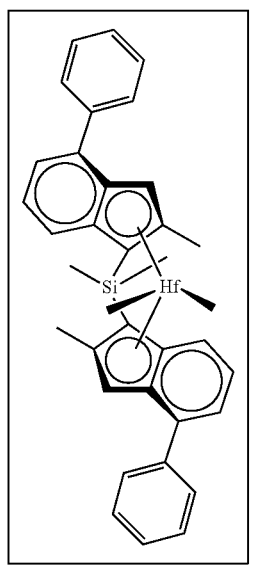
(Metallocene Compound P)

(1) Synthesis of racemic-dimethylsilylenebis(2-methyl-4-phenyl-1-indenyl)hafnium dichloride This was synthesized according to the method described in JP-A 2001-253913.

(2) Synthesis of racemic-dimethylsilylenebis(2-methyl-4-phenyl-1-indenyl)dimethylhafnium 1.48 g (2.07 mmol) of dimethylsilylenebis(2-methyl-4-phenyl-1-indenyl)hafnium dichloride and 60 mL of toluene were put in a 100-mL glass reactor. 14.0 mL (13.9 mmol) of methylmagnesium bromide/tetrahydrofuran solution (0.99 mol/L) was dropwise added thereto at room temperature, and stirred at 80° C. for 3.5 hours. The reaction liquid was cooled to 0° C. in an ice bath, then 1.0 mL (7.9 mmol) of chlorotrimethylsilane was added thereto, stirred at room temperature for 30 minutes, and subsequently 2.7 mL (32 mmol) of 1,4-dioxane was added, and further stirred at room temperature for 30 minutes. The suspension was filtered through Celite, and the filtrate was concentrated under reduced pressure, then statically left at −20° C. for recrystallization to give 322 mg (yield 23%) of a racemic form of dimethylsilylenebis(2-methyl-4-phenyl-1-indenyedimethylhafnium as a yellow crystal.

$^1$H-NMR (400 MHz, $C_6D_6$): δ=7.75 (dd, 4H), 7.49 (d, 2H), 7.27 (d, 2H) 7.23 (t, 4H), 7.12 (t, 2H), 7.03 (s, 2H), 6.85 (dd, 2H), 2.00 (s, 6H), 0.80 (s, 6H), −0.83 (s, 6H).

Synthesis of Metallocene Compound Q (Comparative Example): dimethylsilylenebis(2-isopropyl-4-phenyl-1-indenyl)dimethyl hafnium

[Chem. 21]

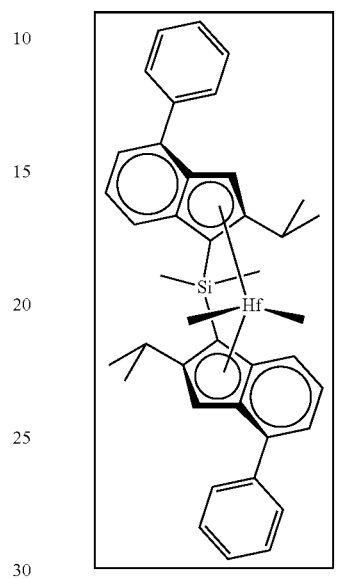
(Metallocene Compound Q)

(1) Synthesis of dimethylbis(2-isopropyl-4-phenylinden-1-yl)silane 2.00 g (8.52 mmol) of 2-isopropyl-4-phenylindene and 30 ml of THF were put in a 200-mL glass reactor, and cooled to −78° C. in a dry ice-methanol bath. 4.10 mL (10.2 mmol) of n-butyllithium/hexane solution (2.5 mol/L) was dropwise added thereto, and stirred at room temperature for 4 hours. This was cooled to −78° C., and 0.34 mg (0.42 mmol) of 1-methylimidazole and 0.50 mL (4.26 mmol) of dimethyldichlorosilane were added thereto in that order, and stirred at room temperature for 1 hour. The solvent was evaporated away under reduced pressure, 30 mL of hexane was added, the suspension was filtered, and the solvent was evaporated away from the filtrate under reduced pressure. The resultant crude product was purified through silica gel column chromatography (developing solvent, petroleum ether) to give 1.00 g (yield 45%) of dimethylbis(2-isopropyl-4-phenylinden-1-yl)silane as a pale yellow solid.

(2) Synthesis of racemic-dimethylsilylenebis(2-isopropyl-4-phenyl-1-indenyl)hafnium dichloride 3.34 g (6.36 mmol) of dimethylbis(2-isopropyl-4-phenylinden-1-yl)silane and 50 ml of diethyl ether were put in a 200-mL glass reactor, and cooled to −70° C. in a dry ice-heptane bath. 8.0 mL (12.8 mmol) of n-butyl lithium/n-hexane solution (1.62 mol/L) was dropwise added thereto, and stirred for 2.5 hours. The solvent was evaporated away under reduced pressure from the reaction liquid, 65 mL of toluene was added, and cooled to −70° C. in a dry ice/heptane bath. 2.04 g (6.37 mmol) of hafnium tetrachloride was added thereto. Subsequently, while gradually restored to room temperature, this was stirred for 17 hours.

The reaction solution was filtered through Celite, and the filtrate was repeatedly crystallized for recrystallization to give 1.20 g of dimethylsilylenebis(2-isopropyl-4-phenyl-1-indenyl)hafnium dichloride, as a mixture of racemic form/meso form=77/23.

60 mg of anhydrous lithium chloride and 6 mL of DME were added to the mixture, and stirred at 60° C. for 5 hours. The reaction liquid was cooled to room temperature, then filtered through glass frit, and the solid was washed twice with 5 mL of DME to give 464 mg (yield 10%) of a racemic form of dimethylsilylenebis(2-isopropyl-4-phenyl-1-indenyl)hafnium dichloride as an orange solid.

$^1$H-NMR (400 MHz, CDCl$_3$): δ=7.74-7.70 (m, 6H), 7.44 (t, 4H), 7.40-7.28 (m, 4H), 7.07 (dd, 2H), 6.89 (s, 2H), 3.31 (sep, 2H), 1.36 (s, 6H), 1.14 (d, 6H), 1.11 (d, 6H).

(3) Synthesis of racemic-dimethylsilylenebis(2-isopropyl-4-phenyl-1-indenyl)dimethylhafnium 444 mg (0.575 mmol) of dimethylsilylenebis(2-isopropyl-4-phenyl-1-indenyl)hafnium dichloride and 20 mL of toluene were put in a 100-mL glass reactor. 4.3 mL (4.6 mmol) of methyllithium-diethyl ether solution (1.06 mol/L) was dropwise added thereto at room temperature, and stirred at 80° C. for 5 hours. The reaction liquid was filtered through Celite, and the filtrate was concentrated under reduced pressure, and statically left at −20° C. for recrystallization to give 203 mg (yield 48%) of a racemic form of dimethylsilylenebis(2-isopropyl-4-phenyl-1-indenyl)dimethylhafnium as a yellow crystal.

$^1$H-NMR (400 MHz, C$_6$D$_6$): δ=7.80 (dd, 4H), 7.50 (d, 2H), 7.36-7.16 (m, 8H) 7.11 (t, 2H), 6.85 (t, 2H), 3.06 (sep, 2H), 1.15 (d, 6H), 0.95 (d, 6H), −0.83 (s, 6H).

Synthesis of Metallocene Compound R (Comparative Example): dimethylsilylenebis(2,4-dimethyl-1-indenyl)dimethylhafnium

[Chem. 22]

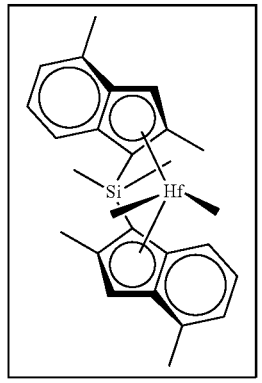

(Metallocene Compound R)

(1) Synthesis of dimethylbis(2,4-dimethyl-inden-1-yl)silane

This was synthesized according to the method described in Japanese Patent 3389265.

(2) Synthesis of racemic-dimethylsilylenebis(2,4-dimethyl-1-indenyl)hafnium dichloride 5.50 g (16.0 mmol) of dimethylbis(2-methyl-4-methyl-inden-1-yl)silane and 60 ml of diethyl ether were put in a 200-mL glass reactor, and cooled to −70° C. in a dry ice-heptane bath. 14.0 mL (35.2 mmol) of n-butyllithium/n-hexane solution (2.5 mol/L) was dropwise added thereto, and stirred at room temperature for 2 hours and at 50° C. for 2 hours. The solvent was evaporated away under reduced pressure from the reaction liquid, 60 mL of diethyl ether was added, and cooled to −70° C. in a dry ice/heptane bath. 5.60 g (17.6 mmol) of hafnium tetrachloride was added thereto. Subsequently, while gradually restored to room temperature, this was stirred for 4 hours.

150 mL of dichloromethane was added, filtered through Celite, and the filtrate was concentrated for recrystallization to give 0.30 g of a racemic form of dimethylsilylenebis(2,4-dimethyl-indenyl)hafnium dichloride as a yellow solid.

$^1$H-NMR (400 MHz, CDCl$_3$): δ=7.56 (d, 2H), 7.10 (d, 2H), 6.93 (dd, 2H), 6.70 (s, 2H), 2.37 (s, 6H), 2.33 (s, 6H), 1.31 (s, 6H).

(3) Synthesis of racemic-dimethylsilylenebis(2,4-dimethyl-1-indenyl)dimethylhafnium 0.592 g (1.00 mmol) of dimethylsilylenebis(2,4-dimethyl-indenyl)hafnium dichloride and 30 mL of toluene were put in a 100-mL glass reactor. 6.8 mL (6.7 mmol) of methyl-magnesium bromide-tetrahydrofuran solution (0.99 mol/L) was dropwise added thereto at room temperature, and stirred at 80° C. for 7.5 hours. The reaction liquid was cooled to 0° C. in an ice bath, then 0.60 mL (4.7 mmol) of chlorotrimethylsilane was added thereto, stirred at room temperature for 30 minutes, and subsequently, 1.3 mL (15 mmol) of 1,4-dioxane was added, and further stirred at room temperature for 30 minutes. The suspension was filtered through Celite, the solvent was evaporated away under reduced pressure, the resultant yellow solid was suspended in 10 mL of hexane, filtered through glass frit, and the solid was further washed twice with 3 mL of hexane to give 310 mg (yield 56%) of a racemic form of dimethylsilylenebis(2,4-dimethyl-indenyl)dimethylhafnium as a white solid.

$^1$H-NMR (400 MHz, C$_6$D$_6$): δ=7.39 (d, 2H), 6.96 (d, 2H), 6.79 (dd, 2H), 6.57 (s, 2H), 2.28 (s, 6H), 2.03 (s, 6H), 0.80 (s, 6H), −1.08 (s, 6H).

Synthesis of Metallocene Compound S (Comparative Example): dimethylsilylenebis(2-methyl-4-isopropyl-1-indenyl)dimethylhafnium

[Chem. 23]

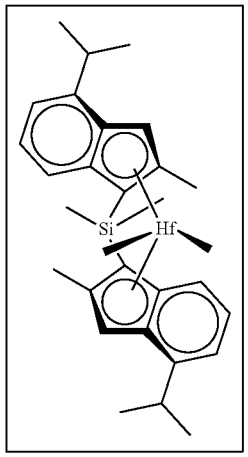

(Metallocene Compound S)

(1) Synthesis of dimethylbis(2-methyl-4-isopropylinden-1-yl)silane

This was synthesized according to the method described in Japanese Patent 3482412.

(2) Synthesis of racemic-dimethylsilylenebis(2-methyl-4-isopropyl-1-indenyl)hafnium dichloride 3.15 g (7.86 mmol) of dimethylbis(2-methyl-4-isopropylinden-1-yl)silane and 45 ml of diethyl ether were put in a 200-mL glass reactor, and cooled to −70° C. in a dry ice-heptane bath. 6.6 mL (16.5 mmol) of n-butyllithium/n-hexane solution (2.5 mol/L) was dropwise added thereto, and stirred at room temperature for 2 hours and at 50° C. for 2 hours. The solvent was evaporated away under reduced pressure from the reaction liquid, 45 mL of diethyl ether was added, and cooled to −70° C. in a dry ice/heptane bath. 2.64 g (8.26 mmol) of hafnium tetrachloride was added thereto. Subsequently, while gradually restored to room temperature, this was stirred for 16 hours.

The reaction liquid was filtered, the resultant solid was extracted with 20 mL of dichloromethane, again filtered, and the solvent was evaporated away from the filtrate under reduced pressure to give 0.50 g of a racemic form of dimethylsilylenebis(2-methyl-4-isopropyl-1-indenyl)hafnium dichloride as a yellow solid.

$^1$H-NMR (400 MHz, CDCl$_3$): δ=7.54 (d, 2H), 7.16 (d, 2H), 6.98 (dd, 2H), 6.76 (s, 2H), 3.06 (sep, 2H), 2.34 (s, 6H), 1.34 (d, 6H), 1.28 (s, 6H), 1.25 (d, 6H).

(3) Synthesis of racemic-dimethylsilylenebis(2-methyl-4-isopropyl-1-indenyl)dimethylhafnium 0.573 g (0.884 mmol) of dimethylsilylenebis(2-methyl-4-isopropyl-1-indenyl)hafnium dichloride and 27 mL of toluene were put in a 100-mL glass reactor. 6.2 mL (6.1 mmol) of methylmagnesium bromide-tetrahydrofuran solution (0.99 mol/L) was dropwise added thereto at room temperature, and stirred at 80° C. for 5 hours. The reaction liquid was cooled to 0° C. in an ice bath, then 0.45 mL (3.6 mmol) of chlorotrimethylsilane was added thereto, stirred at room temperature for 30 minutes, and subsequently, 0.90 mL (11 mmol) of 1,4-dioxane was added, and further stirred at room temperature for 30 minutes. The suspension was filtered through Celite, the solvent was evaporated away under reduced pressure, the resultant yellow solid was suspended in 10 mL of hexane, filtered through glass frit, and the solid was further washed twice with 3 mL of hexane to give 382 mg (yield 71%) of a racemic form of dimethylsilylenebis(2-methyl-4-isopropyl-1-indenyl)dimethylhafnium as a white solid.

$^1$H-NMR (400 MHz, C$_6$D$_6$): δ=7.41 (d, 2H), 7.10 (d, 2H), 6.82 (t, 2H), 6.73 (s, 2H), 3.11 (sep, 2H), 2.07 (s, 6H), 1.36 (d, 2H), 1.27 (d, 6H), 0.83 (s, 6H), −1.06 (s, 6H).

Synthesis of Metallocene Compound T (Comparative Example): cyclobutylidenebis(1-indenyl)dimethylhafnium

[Chem. 24]

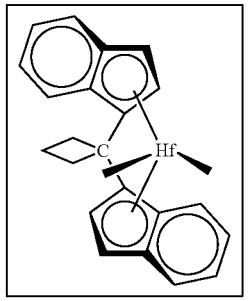

(Metallocene Compound T)

(1) Synthesis of 1,1-bis(1-indenyl)cyclobutane 25.0 g (215 mmol) of indene, 250 mL of DME and 27.0 g (480 mmol) of potassium hydroxide were put in a 200-mL glass reactor, and heated under reflux at 90° C. for 1 hour. The reaction liquid was cooled to 0° C., and 8.40 g (120 mmol) of cyclobutanone was added, and then heated under reflux at 90° C. for 6 hours. The reaction liquid was cooled to room temperature, 200 mL of distilled water was added, then transferred into a separatory funnel, extracted twice with ethyl acetate, and the resultant ethyl acetate solution was washed with saturated saline water and then with distilled water, and dried with sodium sulfate. Sodium sulfate was filtered away, the solvent was evaporated away under reduced pressure, and the resultant crude product was purified through silica gel column chromatography (developing solvent, petroleum ether) to give 12.0 g (yield 39%) of 1,1-bis(1-indenyl)cyclobutane as a white solid.

¹H-NMR (400 MHz, CDCl₃); δ7.39 (t, 4H), 7.11 (quint, 4H), 6.62 (s, 2H), 3.40 (s, 4H), 2.73 (t, 4H), 2.09 (quint, 2H).

(2) Synthesis of racemic-cyclobutylidenebis(1-indenyl)hafnium dichloride 2.84 g (10.0 mmol) of 1,1-bis(1-indenyl)cyclobutane and 100 ml of diethyl ether were put in a 200-mL glass reactor, and cooled to −70° C. in a dry ice-heptane bath. 12.4 mL (20.5 mmol) of n-butyl lithium/n-hexane solution (1.64 mol/L) was dropwise added thereto, and stirred at room temperature for 4 hours. The solvent was evaporated away under reduced pressure from the reaction liquid, 115 mL of toluene was added, and cooled to −70° C. in a dry ice/heptane bath. 3.20 g (10.0 mmol) of hafnium tetrachloride was added thereto. Subsequently, while gradually restored to room temperature, this was stirred for 17 hours.

The solvent was evaporated away from the reaction liquid under reduced pressure, 26 mL of DME was added thereto, and stirred at 60° C. for 5 hours. The reaction liquid was cooled to room temperature, filtered through glass frit, and the resultant solid was extracted with 130 mL of dichloromethane, and filtered through Celite. The filtrate was dried under reduced pressure to give 3.76 g (yield 71%) of a racemic form of cyclobutylidenebis(1-indenyl)hafnium dichloride as a yellow solid.

¹H-NMR (400 MHz, CDCl₃): δ=7.51 (d, 2H), 7.48 (d, 2H), 7.27 (dd, 2H), 6.98 (dd, 2H), 6.53 (d, 2H), 5.97 (d, 2H), 3.54 (quart, 2H), 3.12 (quart, 2H), 2.46 (quint, 2H).

(3) Synthesis of cyclobutylidenebis(1-indenyl)dimethylhafnium 1.50 g (2.82 mmol) of cyclobutylidenebis(1-indenyl)hafnium dichloride and 70 mL of toluene were put in a 200-mL glass reactor. 6.6 mL (19.8 mmol) of methylmagnesium bromide-diethyl ether solution (3.0 mol/L) was dropwise added thereto at room temperature, and stirred at 80° C. for 7 hours. The reaction liquid was cooled to 0° C. in an ice bath, then 1.75 mL (13.9 mmol) of chlorotrimethylsilane was added, stirred at room temperature for 30 minutes, and subsequently 3.50 mL (40.9 mmol) of 1,4-dioxane was added, and further stirred at room temperature for 1 hour. The suspension was filtered through Celite, and the solvent was evaporated away under reduced pressure. The resultant yellow solid was suspended in 10 mL of hexane, filtered through glass frit, and the solid was further washed twice with 5 mL of hexane to give 810 mg (yield 59%) of a racemic form of cyclobutylidenebis(indenyl)dimethylhafnium as a yellow solid.

¹H-NMR (400 MHz, C₆D₆): δ=7.37 (d, 2H), 7.11 (dd, 2H), 7.05 (dd, 2H), 7.23 (dd, 2H), 6.33 (d, 2H), 5.42 (d, 2H), 2.98 (quart, 2H), 2.54 (quart, 2H), 2.02 (quint, 2H), −1.16 (s, 6H).

Synthesis of Metallocene Compound U: cyclobutylidenebis[4-(3,5-di-t-butylphenyl)-1-indenyl]dimethiumhafnium

[Chem. 25]

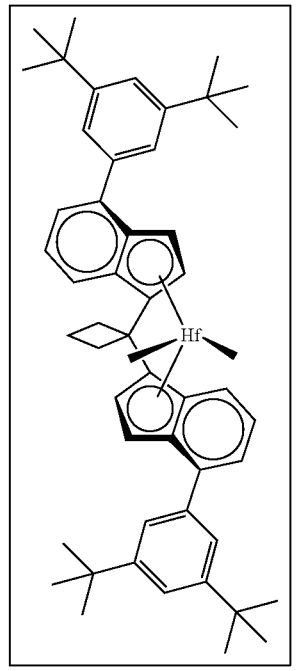

(Metallocene Compound U)

(1) Synthesis of 4-(3,5-di-t-butylphenyl)indene

This was synthesized according to the method described in JP-A 2008-101034.

(2) Synthesis of 1,1-bis[4-(3,5-di-t-butylphenyl)-inden-1-yl]cyclobutane 15.7 g (51.6 mmol) of 4-(3,5-di-t-butylphenyl)indene, 85 mL of DME and 3.18 g (56.7 mmol) of potassium hydroxide were put in a 500-mL glass reactor, and heated under reflux at 90° C. for 2 hours. The reaction liquid was cooled to 0° C., and 1.95 mL (21.9 mmol) of cyclobutanone was added, and then heated under reflux at 90° C. for 6 hours. The reaction liquid was cooled to room temperature, 6 mL of concentrated hydrochloric acid and 200 mL of distilled water were added, then transferred into a separatory funnel, extracted three times with diisopropyl ether, and the resultant diisopropyl ether solution was washed three times with distilled water, and dried with sodium sulfate. Sodium sulfate was filtered away, the solvent was evaporated away under reduced pressure, and the resultant crude product was purified through silica gel column chromatography (developing solvent, hexane) to give 13.6 g (yield 80%) of 1,1-bis[4-(3,5-di-t-butylphenyl)-inden-1-yl]cyclobutane as an orange solid.

¹H-NMR (400 MHz, CDCl₃): δ7.41 (d, 2H), 7.40 (s, 2H), 7.34 (s, 4H), 7.24 (t, 2H), 7.16 (d, 2H), 6.68 (s, 2H), 3.48 (s, 4H), 2.78 (t, 4H), 2.09 (quint, 2H), 1.35 (s, 36H).

(3) Synthesis of racemic-cyclobutylidenebis[4-(3,5-di-t-butylphenyl)-indenyl]hafnium dichloride 3.31 g (5.00 mmol) of 1,1-bis[4-(3,5-di-t-butylphenyl)-inden-1-yl]cyclobutane and 50 ml of diethyl ether were put in a 200-mL glass reactor, and cooled to 0° C. in an ice bath. 6.5 mL (10.3 mmol) of n-butyl lithium/n-hexane solution (1.58 mol/L) was dropwise added thereto, and stirred at room temperature for 4 hours. The solvent was evaporated away under reduced pressure from the reaction liquid, 60 mL of toluene was added, and cooled to −70° C. in a dry ice/heptane bath. 1.60 g (5.00 mmol) of hafnium tetrachloride was added thereto. Subsequently, while gradually restored to room temperature, this was stirred for 17 hours. The ratio of the racemic form to the meso form formed in this stage was 18/82.

The solvent was evaporated away from the reaction liquid under reduced pressure, 5 mL of DME and 7 mL of n-hexane were added thereto, and stirred at 45° C. for 4 hours. The reaction liquid was cooled to room temperature, and filtered through glass frit to give 887 mg of a racemic form of cyclobutylidenebis[4-(3,5-di-t-butylphenyl)-indenyl]hafnium dichloride containing lithium chloride, as an orange solid.

$^1$H-NMR (400 MHz, CDCl$_3$): δ=7.52 (d, 2H), 7.48 (s, 4H), 7.40 (s, 2H), 7.31 (d, 2H), 7.10 (dd, 2H), 6.72 (d, 2H), 6.08 (d, 2H), 3.60 (quartet, 2H), 3.18 (quartet, 2H), 2.48 (quintet, 2H), 1.30 (s, 36H).

(4) Synthesis of racemic-cyclobutylidenebis[4-(3,5-di-t-butylphenyl)-1-indenyl]dimethylhafnium 855 mg of the above-mentioned, lithium chloride-containing cyclobutylidenebis[4-(3,5-di-t-butylphenyl)-indenyl]hafnium dichloride (the content is 0.941 mmol or less) and 50 mL of toluene were put in a 100-mL glass reactor. 3.15 mL (9.45 mmol) of methylmagnesium bromide/diethyl ether solution (3.0 mol/L) was dropwise added thereto at room temperature, and stirred at 90° C. for 5 hours. The reaction liquid was cooled to 0° C. in an ice bath, then 0.95 mL (7.5 mmol) of chlorotrimethylsilane was added thereto, stirred at room temperature for 30 minutes, and subsequently 1.95 mL (22.8 mmol) of 1,4-dioxane was added, and further stirred at room temperature for 30 minutes. The suspension was filtered through Celite, and the solvent was evaporated away under reduced pressure. The resultant yellow solid was suspended in 5 mL of hexane and filtered through glass frit to give 615 mg of a racemic form of cyclobutylidenebis[4-(3,5-di-t-butylphenyl)-1-indenyl]dimethylhafnium as a yellow solid. The yield based on the ligand was 15% (presumed that all the dichloro form was used).

$^1$H-NMR (400 MHz, C$_6$D$_6$): δ=7.80 (d, 4H), 7.59 (t, 2H), 7.33 (d, 2H), 7.16 (d, 2H), 6.92 (d, 2H), 6.87 (dd, 2H), 5.53 (d, 2H), 3.08 (quartet, 2H), 2.60 (quartet, 2H), 2.07 (quintet, 2H), 1.35 (s, 36H), −0.87 (s, 6H).

<2> Batch Solution Polymerization:
Ethylene/1-Hexene Copolymerization

Example 1

1000 mL of toluene and 58 mL of 1-hexene were put in a 2.3-L stainless autoclave (equipped with a stirrer and a temperature control unit) that had been fully dried and purged with nitrogen, and heated at 150° C. After the temperature inside the reactor became stable, the reactor was pressurized up to 0.7 MPaG with nitrogen, and further up to 2.7 MPaG with ethylene. Subsequently, 0.1 mmol of tri(n-octyl)aluminium was introduced as pressurized with nitrogen. A solution of metallocene compound A 0.24 μmol-toluene 1 mL, and a solution of cocatalyst [Me$_2$N(H)C$_6$H$_5$][B(C$_6$F$_5$)$_4$] 0.12 μmol-toluene 1 mL were brought into contact with each other in nitrogen at room temperature, and then stirred at room temperature for 10 minutes, and the resultant solution was introduced into the reactor, as pressurized with nitrogen, and the polymerization was started. Subsequently, while the inner pressure was controlled to be at 2.7 MPa, this was kept stirred for 13 minutes, and then ethanol was introduced as pressurized with nitrogen to stop the reaction. After cooled, this was dried to give a polymer. The polymer yield was 10.0 g.

The polymer indices were: density=0.8804 g/cm$^3$, MFR=1.22 g/10 min, weight-average molecular weight Mw=98,900, number-average molecular weight Mn=51,500, Mw/Mn=1.92, T$_m$=61.2° C., 1-hexene content 11.1 mol %.

Example 2

The same polymerization operation as in Example 1 was carried out, except that 0.07 μmol of the metallocene compound A was used, 0.14 μmol of the cocatalyst was used, and the polymerization time was 14 minutes. The polymer yield was 6.7 g.

The polymer indices were: density=0.8800 g/cm$^3$, MFR=0.79 g/10 min, Mw=108,100, Mn=51,700, Mw/Mn=2.09, T$_m$=59.6° C.

Example 3

The same polymerization operation as in Example 1 was carried out, except that 0.28 μmol of the metallocene compound B was used in place of the metallocene compound A, 0.14 μmol of the cocatalyst was used, and the polymerization time was 12 minutes. The polymer yield was 7.3 g.

The polymer indices were: density=0.8793 g/cm$^3$, MFR=0.87 g/10 min, Mw=104,100, Mn=52,100, Mw/Mn=2.00, T$_m$=60.0° C.

Example 4

The same polymerization operation as in Example 1 was carried out, except that 0.30 μmol of the metallocene compound C was used in place of the metallocene compound A, 0.15 μmol of the cocatalyst was used, and the polymerization time was 12 minutes. The polymer yield was 4.3 g.

The polymer indices were: density=0.8770 g/cm$^3$, MFR=0.18 g/10 min, Mw=171,300, Mn=84,800, Mw/Mn=2.02, T$_m$=59.4° C., 1-hexene content 11.4 mol %.

Example 5

The same polymerization operation as in Example 1 was carried out, except that 0.28 μmol of the metallocene compound D was used in place of the metallocene compound A, 0.14 μmol of the cocatalyst was used, and the polymerization time was 12 minutes. The polymer yield was 7.8 g.

The polymer indices were: density=0.8821 g/cm$^3$, MFR=0.40 g/10 min, Mw=120,600, Mn=53,800, Mw/Mn=2.24, T$_m$=62.3° C.

Example 6

The same polymerization operation as in Example 1 was carried out, except that 0.14 μmol of the metallocene compound E was used in place of the metallocene compound A, 0.07 μmol of the cocatalyst was used, and the polymerization time was 5 minutes. The polymer yield was 4.6 g.

The polymer indices were: density=0.8793 g/cm$^3$, MFR=0.87 g/10 min, Mw=100,200, Mn=48,200, Mw/Mn=2.08, $T_m$=60.1° C.

Example 7

The same polymerization operation as in Example 1 was carried out, except that 0.14 μmol of the metallocene compound F was used in place of the metallocene compound A, 0.7 μmol of the cocatalyst was used, and the polymerization time was 5 minutes. The polymer yield was 7.6 g.

The polymer indices were: density=0.8790 g/cm$^3$, MFR=0.80 g/10 min, Mw=118,000, Mn=60,800, Mw/Mn=1.94, $T_m$=61.4° C., 1-hexene content 11.2 mol %.

Example 8

The same polymerization operation as in Example 1 was carried out, except that 0.28 μmol of the metallocene compound G was used in place of the metallocene compound A, 0.14 μmol of the cocatalyst was used, and the polymerization time was 12 minutes. The polymer yield was 4.7 g.

The polymer indices were: density=0.8775 g/cm$^3$, MFR=0.52 g/10 min, Mw=110,600, Mn=53,700, Mw/Mn=2.06, $T_m$=59.0° C., 1-hexene content 11.5 mol %.

Example 9

The same polymerization operation as in Example 1 was carried out, except that 0.14 μmol of the metallocene compound H was used in place of the metallocene compound A, 0.07 μmol of the cocatalyst was used, and the polymerization time was 5 minutes. The polymer yield was 6.5 g.

The polymer indices were: density=0.8685 g/cm$^3$, MFR=1.80 g/10 min, Mw=96,700, Mn=44,400, Mw/Mn=2.18, $T_m$=50.6° C., 1-hexene content 14.1 mol %.

Example 10

The same polymerization operation as in Example 1 was carried out, except that 0.20 μmol of the metallocene compound I was used in place of the metallocene compound A, 0.10 μmol of the cocatalyst was used, and the polymerization time was 5 minutes. The polymer yield was 7.7 g.

The polymer indices were: density=0.8740 g/cm$^3$, MFR=1.56 g/10 min, Mw=101,100, Mn=52,900, Mw/Mn=1.91, $T_m$=56.0° C., 1-hexene content 12.5 mol %.

Example 11

The same polymerization operation as in Example 1 was carried out, except that 0.20 μmol of the metallocene compound J was used in place of the metallocene compound A, 0.10 μmol of the cocatalyst was used, and the polymerization time was 5 minutes. The polymer yield was 5.4 g.

The polymer indices were: density=0.8760 g/cm$^3$, MFR=1.30 g/10 min, Mw=96,700, Mn=48,400, Mw/Mn=2.00, $T_m$=57.5° C., 1-hexene content 12.6 mol %.

Example 12

The same polymerization operation as in Example 1 was carried out, except that 0.20 μmol of the metallocene compound K was used in place of the metallocene compound A, 0.10 μmol of the cocatalyst was used, and the polymerization time was 5 minutes. The polymer yield was 6.9 g.

The polymer indices were: density=0.8806 g/cm$^3$, MFR=1.65 g/10 min, Mw=93,500, Mn=47,900, Mw/Mn=1.95, $T_m$=61.7° C.

Example 13

The same polymerization operation as in Example 1 was carried out, except that 0.20 μmol of the metallocene compound L was used in place of the metallocene compound A, 0.10 μmol of the cocatalyst was used, and the polymerization time was 13 minutes. The polymer yield was 7.0 g.

The polymer indices were: density=0.8831 g/cm$^3$, MFR=0.71 g/10 min, Mw=111,000, Mn=55,800, Mw/Mn=1.99, $T_m$=62.7° C.

Example 14

The same polymerization operation as in Example 1 was carried out, except that 0.20 μmol of the metallocene compound M was used in place of the metallocene compound A, 0.10 μmol of the cocatalyst was used, and the polymerization time was 5 minutes. The polymer yield was 3.3 g.

The polymer indices were: density=0.8842 g/cm$^3$, MFR=0.83 g/10 min, Mw=115,500, Mn=60,800, Mw/Mn=1.90, $T_m$=63.4° C.

Example 15

The same polymerization operation as in Example 1 was carried out, except that 0.14 μmol of the metallocene compound N was used in place of the metallocene compound A, 0.07 μmol of the cocatalyst was used, and the polymerization time was 5 minutes. The polymer yield was 7.3 g.

The polymer indices were: density=0,8767 g/cm$^3$, MFR=0.31 g/10 min, Mw=140,200, Mn=66,800, Mw/Mn=2.10, $T_m$=59.0° C., 1-hexene content 11.5 mol %.

Example 16

The same polymerization operation as in Example 1 was carried out, except that 0.20 μmol of the metallocene compound 0 was used in place of the metallocene compound A, 0.10 μmol of the cocatalyst was used, and the polymerization time was 13 minutes. The polymer yield was 9.0 g.

The polymer indices were: density=0.8756 g/cm$^3$, MFR=0.47 g/10 min, Mw=150,800, Mn=74,300, Mw/Mn=2.03, $T_m$=58.1° C.

Comparative Example 1

The same polymerization operation as in Example 1 was carried out, except that 0.48 μmol of the metallocene compound P was used in place of the metallocene compound A, 0.24 μmol of the cocatalyst was used, and the polymerization time was 5 minutes. The polymer yield was 13.6 g.

The polymer indices were: density=0.8764 g/cm$^3$, MFR=51 g/10 min, Mw=41,800, Mn=10,300, Mw/Mn=4.04, $T_m$=67.0° C., 1-hexene content 12.3 mol %.

Comparative Example 2

The same polymerization operation as in Example 1 was carried out, except that 0.70 μmol of the metallocene compound Q was used in place of the metallocene compound A, 0.35 μmol of the cocatalyst was used, and the polymerization time was 18 minutes. The polymer yield was 6.0 g.

The polymer indices were: Mw=6,800, Mn=3,100, Mw/Mn=2.17, $T_m$=62.0° C.

Comparative Example 3

The same polymerization operation as in Example 1 was carried out, except that 0.10 μmol of the metallocene compound R was used in place of the metallocene compound A, 0.05 μmol of the cocatalyst was used, and the polymerization time was 5 minutes. The polymer yield was 6.0 g.

The polymer indices were: density=0.9053 g/cm³, MFR=0.47 g/10 min, Mw=131,900, Mn=32,500, Mw/Mn=4.06, $T_m$=88.3° C.

Comparative Example 4

The same polymerization operation as in Example 1 was carried out, except that 0.20 μmol of the metallocene compound S was used in place of the metallocene compound A, 0.10 μmol of the cocatalyst was used, and the polymerization time was 12 minutes. The polymer yield was 6.8 g.

The polymer indices were: density=0.9073 g/cm³, MFR=0.35 g/10 min, Mw=144,100, Mn=12,800, Mw/Mn=11.29, $T_m$=95.8° C.

Comparative Example 5

The same polymerization operation as in Example 1 was carried out, except that 0.10 mol of the metallocene compound T was used in place of the metallocene compound A, 0.05 μmol of the cocatalyst was used, and the polymerization time was 5 minutes. The polymer yield was 7.0 g.

The polymer indices were: density=0.8962 g/cm³, MFR=0.51 g/10 min, Mw=120,900, Mn=63,600, Mw/Mn=1.90, $T_m$=83.7° C.

Example 17

The same polymerization operation as in Example 1 was carried out, except that 0.14 μmol of the metallocene compound U was used in place of the metallocene compound A, 0.07 μmol of the cocatalyst was used, and the polymerization time was 5 minutes. The polymer yield was 4.3 g.

The polymer indices were: density=0.8673 g/cm³, MFR=0.65 g/10 min, Mw=129,600, Mn=67,500, Mw/Mn=1.92, $T_m$=50.5° C., 1-hexene content 13.4 mol %.

Example 18

The same polymerization operation as in Example 1 was carried out, except that 0.14 μmol of the metallocene compound A was used, 0.28 μmol of the cocatalyst was used, 33 mL of 1-hexene was used, and the polymerization time was 12 minutes. The polymer yield was 5.4 g.

The polymer indices were: density=0.8965 g/cm³, MFR=0.19 g/10 min, Mw=169,100, Mn=90,900, Mw/Mn=1.86, $T_m$=80.2° C., 1-hexene content 6.6 mol %.

Example 19

The same polymerization operation as in Example 1 was carried out, except that 0.13 μmol of the metallocene compound C was used in place of the metallocene compound A, 0.26 μmol of the cocatalyst was used, 33 mL of 1-hexene was used, and the polymerization time was 13 minutes. The polymer yield was 7.0 g.

The polymer indices were: density=0.8948 g/cm³, MFR=0.24 g/10 min, Mw=212,800, Mn=101,300, Mw/Mn=2.10, $T_m$=79.9° C.

Example 20

The same polymerization operation as in Example 1 was carried out, except that 0.15 μmol of the metallocene compound C was used in place of the metallocene compound A, 0.30 μmol of the cocatalyst was used, 96 mL of 1-hexene was used, and the polymerization time was 12 minutes. The polymer yield was 14.3 g.

The polymer indices were: density=0.8593 g/cm³, MFR=3.7 g/10 min, Mw=81,500, Mn=40,800, Mw/Mn=2.00, $T_m$=40.4° C., 1-hexene content 17.5 mol %.

Comparative Example 6

The same polymerization operation as in Example 1 was carried out, except that 0.30 μmol of the metallocene compound P was used in place of the metallocene compound A, 0.15 μmol of the cocatalyst was used, 33 mL of 1-hexene was used, and the polymerization time was 5 minutes. The polymer yield was 19.1 g.

The polymer indices were: density=0.8981 g/cm³, MFR=5.3 g/10 min, Mw=84,400, Mn=19,200, Mw/Mn=4.40, $T_m$=77.8° C.

Comparative Example 7

The same polymerization operation as in Example 1 was carried out, except that 0.80 μmol of the metallocene compound Q was used in place of the metallocene compound A, 0.40 μmol of the cocatalyst was used, 33 mL of 1-hexene was used, and the polymerization time was 12 minutes. The polymer yield was 15.1 g.

The polymer indices were: MFR=3600 g/10 min, Mw=8,200, Mn=3,600, Mw/Mn=2.25, $T_m$=75.7° C.

Example 21

The same polymerization operation as in Example 1 was carried out, except that 0.10 μmol of the metallocene compound C was used in place of the metallocene compound A, 0.20 μmol of the cocatalyst was used, 62 mL of 1-hexene was used, the polymerization temperature was 125° C., and the polymerization time was 12 minutes. The polymer yield was 8.0 g.

The polymer indices were: density=0.8745 g/cm³, MFR=0.04 g/10 min, Mw=287,600, Mn=126,700, Mw/Mn=2.27, $T_m$=56.0° C., 1-hexene content 12.3 mol %.

Comparative Example 8

The same polymerization operation as in Example 1 was carried out, except that 0.10 μmol of the metallocene compound P was used in place of the metallocene compound A, 0.05 μmol of the cocatalyst was used, 62 mL of 1-hexene was used, the polymerization temperature was 125° C., and the polymerization time was 4 minutes. The polymer yield was 10.9 g.

The polymer indices were: density=0.8750 g/cm³, MFR=0.44 g/10 min, Mw=147,200, Mn=68,100, Mw/Mn=2.16, $T_m$=58.6° C.

The properties of Examples 1 to 17 and Comparative Examples 1 to 5 are collectively shown in Table 1, and the properties of Examples 1, 4, 18 to 21 and Comparative Examples 1, 2, 6 to 8 are in Table 2.

TABLE 1

Performance Comparison between Metallocene Compounds at the same polymerization temperature (150° C.) and under the same 1-hexene concentration (58 mL)

| Example | Metallocene Compound | Mn | Mw/Mn | MFR [g/10 min] | Density [g/cm³] | Tm [° C.] | C6 Content [mol %] |
|---|---|---|---|---|---|---|---|
| Example 1 | A | 51,500 | 1.92 | 1.22 | 0.8804 | 61.2 | 11.1 |
| Example 2 | A | 51,700 | 2.09 | 0.79 | 0.8800 | 59.6 | — |
| Example 3 | B | 52,100 | 2.00 | 0.87 | 0.8793 | 60.0 | — |
| Example 4 | C | 84,800 | 2.02 | 0.18 | 0.8770 | 59.4 | 11.4 |
| Example 5 | D | 53,800 | 2.24 | 0.40 | 0.8821 | 62.3 | — |
| Example 6 | E | 48,200 | 2.08 | 0.87 | 0.8793 | 60.1 | — |
| Example 7 | F | 60,800 | 1.94 | 0.80 | 0.8790 | 61.4 | 11.2 |
| Example 8 | G | 53,700 | 2.06 | 0.52 | 0.8775 | 59.0 | 11.5 |
| Example 9 | H | 44,400 | 2.18 | 1.80 | 0.8685 | 50.6 | 14.1 |
| Example 10 | I | 52,900 | 1.91 | 1.56 | 0.8740 | 56.0 | 12.5 |
| Example 11 | J | 48,400 | 2.00 | 1.30 | 0.8760 | 57.5 | 12.6 |
| Example 12 | K | 47,900 | 1.95 | 1.65 | 0.8806 | 61.7 | — |
| Example 13 | L | 55,800 | 1.99 | 0.71 | 0.8831 | 62.7 | — |
| Example 14 | M | 60,800 | 1.90 | 0.83 | 0.8842 | 63.4 | — |
| Example 15 | N | 66,800 | 2.10 | 0.31 | 0.8767 | 59.0 | 11.5 |
| Example 16 | O | 74,300 | 2.03 | 0.47 | 0.8756 | 58.1 | — |
| Example 17 | U | 67,500 | 1.92 | 0.65 | 0.8673 | 50.5 | 13.4 |
| Comparative Example 1 | P | 10,300 | 4.04 | 51 | 0.8764 | 67.0 | 12.3 |
| Comparative Example 2 | Q | 3,100 | 2.17 | — | unmeasurable* | 62.0 | — |
| Comparative Example 3 | R | 32,500 | 4.06 | 0.47 | 0.9053 | 88.3 | — |
| Comparative Example 4 | S | 12,800 | 11.29 | 0.35 | 0.9073 | 95.8 | — |
| Comparative Example 5 | T | 63,600 | 1.90 | 0.51 | 0.8962 | 83.7 | — |

*Unmeasurable as the molecular weight is too low.
—: Not measured.

TABLE 2

Performance Comparison between Metallocene Compounds at a different polymerization temperature and under a different 1-hexene concentration

| Example | Metallocene Compound | C6 Amount [mL] | Polymerization Temperature [° C.] | Mn | Mw/Mn | MFR [g/ 10 min] | Density [g/cm³] | Tm [° C.] | C6 Content [mol %] |
|---|---|---|---|---|---|---|---|---|---|
| Example 18 | A | 33 | 150 | 90,900 | 1.86 | 0.19 | 0.8965 | 80.2 | 6.6 |
| Example 1 | A | 58 | 150 | 51,500 | 1.92 | 1.22 | 0.8804 | 61.2 | 11.1 |
| Example 19 | C | 33 | 150 | 101,300 | 2.10 | 0.24 | 0.8948 | 79.9 | — |
| Example 4 | C | 58 | 150 | 84,800 | 2.02 | 0.18 | 0.8770 | 59.4 | 11.4 |
| Example 20 | C | 96 | 150 | 40,800 | 2.00 | 3.7 | 0.8593 | 40.4 | 17.5 |
| Comparative Example 6 | P | 33 | 150 | 19,200 | 4.40 | 5.3 | 0.8981 | 77.8 | — |
| Comparative Example 1 | P | 58 | 150 | 10,300 | 4.04 | 51 | 0.8764 | 67.0 | 12.3 |
| Comparative Example 7 | Q | 33 | 150 | 3,600 | 2.25 | 3600 | * | 75.7 | — |
| Comparative Example 2 | Q | 58 | 150 | 3,100 | 2.17 | — | * | 62.0 | — |
| Example 21 | C | 62 | 125 | 126,700 | 2.27 | 0.04 | 0.8745 | 56.0 | 12.3 |
| Comparative Example 8 | P | 62 | 125 | 68,100 | 2.16 | 0.44 | 0.8750 | 58.6 | — |

* Unmeasurable as the molecular weight is too low.
—: Not measured.

<3> Continuous High-Pressure Ion Polymerization: Ethylene/Propylene/1-Hexene Copolymerization As in Table 3, polymerization was carried out continuously in a 5.0-L stainless autoclave reactor (equipped with a stirrer) that had been fully dried and purged with nitrogen, under a polymerization pressure of about 80 MPa and at a temperature falling within a range of from 200 to 260° C. Ethylene, propylene and hexene were continuously supplied in the polymerization system to be in a predetermined monomer ratio, and the polymerization pressure was controlled by a pressure control valve. As a scavenger, a tri(n-octyl)aluminium/heptane solution controlled to be 30 mg/L was continuously supplied. The metallocene compound and the cocatalyst [Me$_2$N(H)C$_6$H$_5$][B(C$_6$F$_5$)$_4$] were separately prepared as toluene solutions (each having a concentration of from 20 to 50 mg/L, or from 37 to 120 mg/L, respectively), and while mixed in the pipe line, the two were continuously supplied to the polymerization system. The supply speed of the metallocene compound and the cocatalyst was so controlled that the polymerization system could be at a predetermined temperature. During the polymerization, any additional solvent was not used except the solvent that would be carried in the system as the solvent for the catalyst/cocatalyst solution and the solvent for the scavenger solution. The retention time was controlled to be within a range of from 210 to 230 seconds.

The details of the polymerization conditions in Examples I to VII and Comparative Examples I and II, including the supply rate of the metallocene compound (M), the cocatalyst (B) and the organic Al, the molar ratio of B/M and the molar ratio of Al/M of the supplied catalyst components, the monomer supply rate, the molar ratio of the supplied monomers and the polymerization temperature, and also the details of the polymerization results therein including the production rate and the catalyst activity as well as the density of the polymer obtained, the molecular weight, the molecular weight distribution and MFR of the polymer calculated from the data in GPC, the melting point thereof determined through DSC, and the propylene/hexene content in the polymer determined through $^{13}$C-NMR are shown in Table 3.

polymerization temperature verify that the superiority of the catalyst of the present invention extends a broad ethylene/comonomer ratio range and a broad polymerization temperature range. In addition, as obvious from comparison between Examples and Comparative Examples in Table 3, the effect can exhibit even under high-temperature/high-pressure conditions, and in particular, the superiority of the catalyst of the present invention to already-existing catalysts is more remarkable in point of the molecular weight of the produced polymers.

TABLE 3

High-Pressure Ion Polymerization Results

| | Example I | Example II | Example III | Example IV | Example V | Example VI | Example VII | Comparative Example I | Comparative Example II |
|---|---|---|---|---|---|---|---|---|---|
| Metallocene Compound | C | C | A | A | H | H | U | P | P |
| Complex Supply Rate [mg/h] | 62 | 38 | 42 | 21 | 47 | 46 | 34 | 54 | 29 |
| cocatalyst Supply Rate [mg/h] | 107 | 64 | 79 | 48 | 70.2 | 67.4 | 93 | 82 | 82 |
| Organic Al Supply Rate [g/h] | 2.6 | 2.6 | 2.1 | 2.2 | 2.2 | 2.2 | 3.1 | 4.9 | 4.9 |
| B/M [mol/mol] | 1.4 | 1.4 | 1.5 | 1.8 | 1.7 | 1.6 | 3.1 | 1.3 | 2.4 |
| Al/M [mol/mol] | 415 | 415 | 329 | 344 | 489 | 489 | 698 | 820 | 820 |
| Ethylene Supply Rate [kg/h] | 20.5 | 20.8 | 21 | 20.6 | 20.8 | 20.7 | 20.8 | 22.1 | 22.1 |
| Propylene Supply Rate [kg/h] | 6.7 | 6.7 | 6.9 | 6.7 | 6.7 | 6.7 | 6.7 | 6.7 | 6.7 |
| Hexene Supply Rate [kg/h] | 13.3 | 13.2 | 13.5 | 13.5 | 13.3 | 13.3 | 13.3 | 13.5 | 13.5 |
| Molar Ratio of Supplied C2/C3/C6 | 70/15/15 | 70/15/15 | 70/15/15 | 70/15/15 | 70/15/15 | 70/15/15 | 70/15/15 | 71/14.5/14.5 | 71/14.5/14.5 |
| Polymerization Temperature [° C.] | 250 | 230 | 250 | 230 | 250 | 230 | 230 | 240 | 210 |
| Production Rate [kg/h] | 6.2 | 6.2 | 6.8 | 6.8 | 8.0 | 8.0 | 6.5 | 6.4 | 6.4 |
| Catalyst Activity [kg-PE/g-complex] | 100 | 163 | 163 | 324 | 171 | 175 | 192 | 119 | 222 |
| Mn | 24600 | 34500 | 17000 | 21300 | 19500 | 25900 | 30800 | 4800 | 83 |
| Mw/Mn | 1.98 | 1.92 | 2.44 | 2.55 | 1.94 | 1.86 | 1.88 | 4.97 | 4.59 |
| MFR [g/10 min] | 29.2 | 9 | 56 | 19 | 96 | 36 | 18 | 630 | 103 |
| Density [g/cm3] | 0.8909 | 0.8864 | 0.8923 | 0.8875 | 0.8775 | 0.8718 | 0.8719 | 0.8944 | 0.8834 |
| Tm [° C.] | 79.2 | 72 | 81 | 74 | 59 | 55 | no | 78 (104, 119) | 69 (93) |
| C3 Content [mol %] | 5.4 | 5.8 | — | 5.8 | 8 | 8.7 | 8.2 | — | 6.6 |
| C6 Content [mol %] | 4.8 | 5.2 | — | 5.3 | 5.4 | 6.4 | 6.5 | — | 5.8 |

—: Not measured.

Discussion on Comparison Results Between Examples and Comparative Examples

As obvious from Table 1, comparison between Examples 1 to 17 and Comparative Examples 1 to 5 that are the polymerization results at the same polymerization temperature and in the same monomer ratio verifies that the catalyst of the present invention can give a high-molecular-weight ethylene copolymer while exhibiting excellent copolymerizability. Also as obvious from Table 2, comparison between Examples 1, 4, 18 to 20 and Comparative Examples 1, 2, 6 and 7 that are the polymerization results in a monomer ratio differing from the above-mentioned polymerization condition, and comparison between Example 21 and Comparative Example 8 that are the polymerization results at a different While the present invention has been described in detail and with reference to specific embodiments thereof, it will be apparent to one skilled in the art that various changes and modifications can be made therein without departing from the spirit and scope thereof. The present application is based on a Japanese patent application (Patent Application 2013-036535) filed Feb. 27, 2013, the contents thereof being hereby incorporated by reference.

INDUSTRIAL APPLICABILITY

As obvious from the above, use of the metallocene compound of the present invention as a polymerization catalyst provides a high-molecular-weight olefin copolymer while maintaining the excellent olefin copolymerizability as compared with already-existing complex catalyst systems in olefin copolymerization. In particular, the catalyst enables production of an ethylenic copolymer having a low density and a high molecular weight.

Accordingly, the olefin polymerization catalyst of the present invention and the production method for an olefin polymer using the olefin polymerization catalyst make it possible to carry out the polymerization under industrially-advantageous polymerization temperature and condition, and the industrial value of the present invention is extremely great.

In addition, the olefin copolymer produced through polymerization using the metallocene compound of the present invention has excellent mechanical properties, and are widely used covering from industrial-use materials and life materials, for example, as films, sheets, fibers, nonwoven fabrics, various containers, molded articles, modifiers, etc.

The invention claimed is:

1. A method for producing an olefin polymer, which comprises carrying out an ethylene homopolymerization or ethylene/α-olefin copolymerization in the presence of an olefin polymerization catalyst comprising the following components (A) and (B), and optionally comprising the following component (C):

Component (A): a metallocene compound of formula [I]:

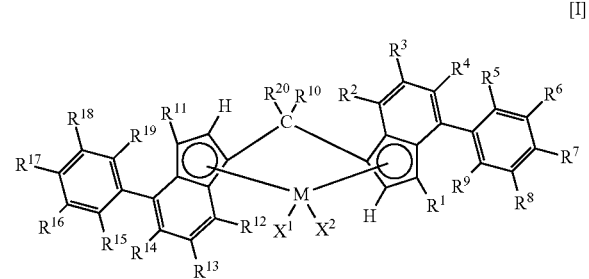

in which:

M represents Ti, Zr, or Hf;

$X^1$ and $X^2$ are the same or different, each representing a hydrogen atom, an alkyl group having from 1 to 10 carbon atoms, an alkoxy group having from 1 to 10 carbon atoms, an aryl group having from 6 to 20 carbon atoms, an aryloxy group having from 6 to 10 carbon atoms, an alkenyl group having from 2 to 10 carbon atoms, an arylalkyl group having from 7 to 40 carbon atoms, an alkylaryl group having from 7 to 40 carbon atoms, an arylalkenyl group having from 8 to 40 carbon atoms, an alkyl group having from 1 to 20 carbon atoms and substituted with a silyl group having a hydrocarbon group having from 1 to 6 carbon atoms, a substituted amino group having from 1 to 10 carbon atoms, a group OH, or a halogen atom;

$R^1$ to $R^9$ and $R^{11}$ to $R^{19}$ are the same or different, each representing a hydrogen atom, a halogen atom, an alkyl group having from 1 to 10 carbon atoms, a halogenoalkyl group having from 1 to 10 carbon atoms, an aryl group having from 6 to 20 carbon atoms, an alkoxy group having from 1 to 10 carbon atoms, a silyl group having a hydrocarbon group having from 1 to 6 carbon atoms, an alkyl group having from 1 to 20 carbon atoms and substituted with a silyl group having a hydrocarbon group having from 1 to 6 carbon atoms, a group —$NR^{21}_2$, a group —$SR^{21}$, a group —$OSiR^{21}_3$, or a group —$PR^{21}_2$, in which $R^{21}$'s are the same or different, each representing a halogen atom, an alkyl group having from 1 to 10 carbon atom or an aryl group having from 6 to 20 carbon atoms, the neighboring groups of $R^1$ to $R^9$ and $R^{11}$ to $R^{19}$ optionally form one or more aromatic rings or aliphatic rings along with the atom bonding them, or $R^4$ and $R^5$, or $R^4$ and $R^9$, or $R^{14}$ and $R^{15}$, or $R^{14}$ and $R^{19}$ optionally form one aromatic ring or aliphatic ring along with the atom bonding them;

$R^{10}$ and $R^{20}$ are the same or different, each representing a hydrogen atom, a halogen atom, an alkyl group having from 1 to 10 carbon atoms, a fluoroalkyl group having from 1 to 10 carbon atoms, an alkoxy group having from 1 to 10 carbon atoms, an aryl group having from 6 to 20 carbon atoms, a fluoroaryl group having from 6 to 10 carbon atoms, an aryloxy group having from 6 to 10 carbon atoms, an alkenyl group having from 2 to 10 carbon atoms, an arylalkyl group having from 7 to 40 carbon atoms, an alkylaryl group having from 7 to 40 carbon atoms, or an arylalkenyl group having from 8 to 40 carbon atoms, provided that $R^{10}$ and $R^{20}$ are not hydrogen atoms at the same time, and $R^{10}$ and $R^{20}$ optionally form one or more rings along with the atom bonding them;

Component (B): a compound or an ion-exchanging layered silicate, which reacts with Component (A) to form an ion pair; and Component (C): an organoaluminium compound;

wherein the polymerization temperature is 120° C. or more.

2. The method according to claim 1, wherein $R^5$ to $R^9$ and $R^{15}$ to $R^{19}$ are the same or different, each representing a hydrogen atom, a halogen atom, an alkyl group having from 1 to 10 carbon atoms, a halogenoalkyl group having from 1 to 10 carbon atoms, an aryl group having from 6 to 10 carbon atoms, a group —$NR^{21}_2$, a group —$SR^{21}$, a group —$OSiR^{21}_3$, or a group —$PR^{21}_2$, in which $R^{21}$'s are the same or different, each representing a halogen atom, an alkyl group having from 1 to 10 carbon atom or an aryl group having from 6 to 10 carbon atoms, and all of $R^5$ to $R^9$ and $R^{15}$ to $R^{19}$ are not hydrogen atoms at the same time.

3. The method according to claim 1, wherein $R^{10}$ and $R^{20}$ are the same or different, each representing a halogen atom, an alkyl group having from 1 to 10 carbon atoms, a fluoroalkyl group having from 1 to 10 carbon atoms, an aryl group having from 7 to 10 carbon atoms, a fluoroaryl group having from 6 to 10 carbon atoms, an alkenyl group having from 2 to 10 carbon atoms, an arylalkyl group having from 7 to 40 carbon atoms, an alkylaryl group having from 7 to 40 carbon atoms or an arylalkenyl group having from 8 to 40 carbon atoms, provided that the total of the carbon atoms that $R^{10}$ and $R^{20}$ contain is 2 or more, and $R^{10}$ and $R^{20}$ optionally form one or more rings along with the atom bonding them.

4. The method according to claim 1, wherein $R^{10}$ and $R^{20}$ form one or more rings along with the atom bonding them.

5. The method according to claim 4, wherein the ring formed by $R^{10}$ and $R^{20}$ is a 4-membered ring or a 5-membered ring.

6. The method according to claim 1, wherein M is Hf.

7. The method according to claim 1, wherein the component (B) is a boron compound.

8. The method according to claim 1, wherein the polymerization catalyst comprises components (A), (B), and (C).

* * * * *